(12) United States Patent
de los Pinos et al.

(10) Patent No.: US 10,300,150 B2
(45) Date of Patent: *May 28, 2019

(54) VIRION-DERIVED NANOSPHERES FOR SELECTIVE DELIVERY OF THERAPEUTIC AND DIAGNOSTIC AGENTS TO CANCER CELLS

(71) Applicant: Aura Biosciences, Inc., Cambridge, MA (US)

(72) Inventors: Elisabet de los Pinos, Brookline, MA (US); Rhonda C. Kines, Washington, DC (US)

(73) Assignee: Aura Biosciences, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/824,685

(22) Filed: Nov. 28, 2017

(65) Prior Publication Data

US 2018/0110883 A1    Apr. 26, 2018

Related U.S. Application Data

(63) Continuation of application No. 15/615,485, filed on Jun. 6, 2017, now Pat. No. 98,553,478, which is a continuation of application No. 14/376,408, filed as application No. PCT/US2013/025230 on Feb. 7, 2013, now Pat. No. 9,700,639.

(60) Provisional application No. 61/596,042, filed on Feb. 7, 2012.

(51) Int. Cl.
| | |
|---|---|
| A61K 9/16 | (2006.01) |
| A61K 45/06 | (2006.01) |
| A61K 49/00 | (2006.01) |
| A61K 38/16 | (2006.01) |
| A61K 9/51 | (2006.01) |
| A61K 51/08 | (2006.01) |
| A61K 47/69 | (2017.01) |
| B82Y 5/00 | (2011.01) |
| A61K 9/00 | (2006.01) |

(52) U.S. Cl.
CPC ............ *A61K 49/0056* (2013.01); *A61K 9/16* (2013.01); *A61K 9/5184* (2013.01); *A61K 38/162* (2013.01); *A61K 45/06* (2013.01); *A61K 47/6901* (2017.08); *A61K 47/6929* (2017.08); *A61K 51/088* (2013.01); *A61K 9/0019* (2013.01); *B82Y 5/00* (2013.01)

(58) Field of Classification Search
None
See application file for complete search history.

(56) References Cited

U.S. PATENT DOCUMENTS

| | | |
|---|---|---|
| 4,625,014 A | 11/1986 | Senter et al. |
| 4,659,839 A | 4/1987 | Nicolotti |
| 5,334,711 A | 8/1994 | Sproat |
| 5,667,764 A | 9/1997 | Kopia et al. |
| 5,716,824 A | 2/1998 | Beigelman |
| 6,022,522 A | 2/2000 | Sweet et al. |
| 6,180,389 B1 | 1/2001 | Douglas et al. |
| 6,416,945 B1 | 7/2002 | McCarthy et al. |
| 6,599,739 B1 | 7/2003 | Lowy et al. |
| 6,719,958 B1 | 4/2004 | Gozzini et al. |
| 6,984,386 B2 | 1/2006 | Douglas et al. |
| 6,991,795 B1 | 1/2006 | Lowe et al. |
| 7,205,126 B2 | 4/2007 | Qiao et al. |
| 7,351,533 B2 | 4/2008 | McCarthy et al. |
| 7,951,379 B2 | 5/2011 | Kuroda et al. |
| 8,394,411 B2 | 3/2013 | Roberts et al. |
| 9,700,639 B2 | 7/2017 | de los Pinos et al. |
| 9,724,404 B2 | 8/2017 | Coursaget et al. |
| 9,855,347 B2 | 1/2018 | de los Pinos et al. |
| 10,117,947 B2 | 11/2018 | de los Pinos et al. |
| 2003/0129583 A1 | 7/2003 | Martin et al. |
| 2003/0206887 A1 | 11/2003 | Morrissey et al. |
| 2004/0005338 A1 | 1/2004 | Bachmann et al. |
| 2004/0028694 A1 | 2/2004 | Young et al. |
| 2004/0115132 A1 | 6/2004 | Young et al. |
| 2004/0121465 A1 | 6/2004 | Robinson |
| 2004/0146531 A1 | 7/2004 | Antonsson et al. |
| 2004/0152181 A1 | 8/2004 | McCarthy et al. |
| 2005/0112141 A1 | 5/2005 | Terman |
| 2005/0118191 A1 | 6/2005 | Robinson et al. |
| 2005/0181064 A1 | 8/2005 | Kuroda |
| 2006/0088536 A1 | 4/2006 | Kuroda |
| 2006/0141042 A1 | 6/2006 | Kuroda |
| 2006/0166913 A1 | 7/2006 | Suzuki |
| 2006/0204444 A1 | 9/2006 | Young et al. |
| 2006/0216238 A1 | 9/2006 | Manchester et al. |
| 2006/0269954 A1 | 11/2006 | Lowy et al. |
| 2007/0059245 A1 | 3/2007 | Young et al. |
| 2007/0059746 A1 | 3/2007 | Kuroda |

(Continued)

FOREIGN PATENT DOCUMENTS

| | | |
|---|---|---|
| CN | 1904012 A | 1/2007 |
| EP | 1491210 A1 | 12/2004 |

(Continued)

OTHER PUBLICATIONS

Culp et al., Papillomavirus Particles Assembled in 293TT Cells Are Infectious In Vivo, 2006, Journal of Virology, vol. 80, No. 22, pp. 11381-11384.*

(Continued)

*Primary Examiner* — Benjamin P Blumel
(74) *Attorney, Agent, or Firm* — Wolf, Greenfield & Sacks, P.C.

(57) ABSTRACT

The invention relates to methods for producing papilloma-derived nanosphere particles that contain therapeutic, diagnostic, or other agents. The invention also provides nanosphere particle preparations that are useful for selectively delivering therapeutic, diagnostic, and/or other agents to cancer cells of subjects without eliciting a serotype-specific immunogenic response in the subjects.

31 Claims, 21 Drawing Sheets

Figure 1:
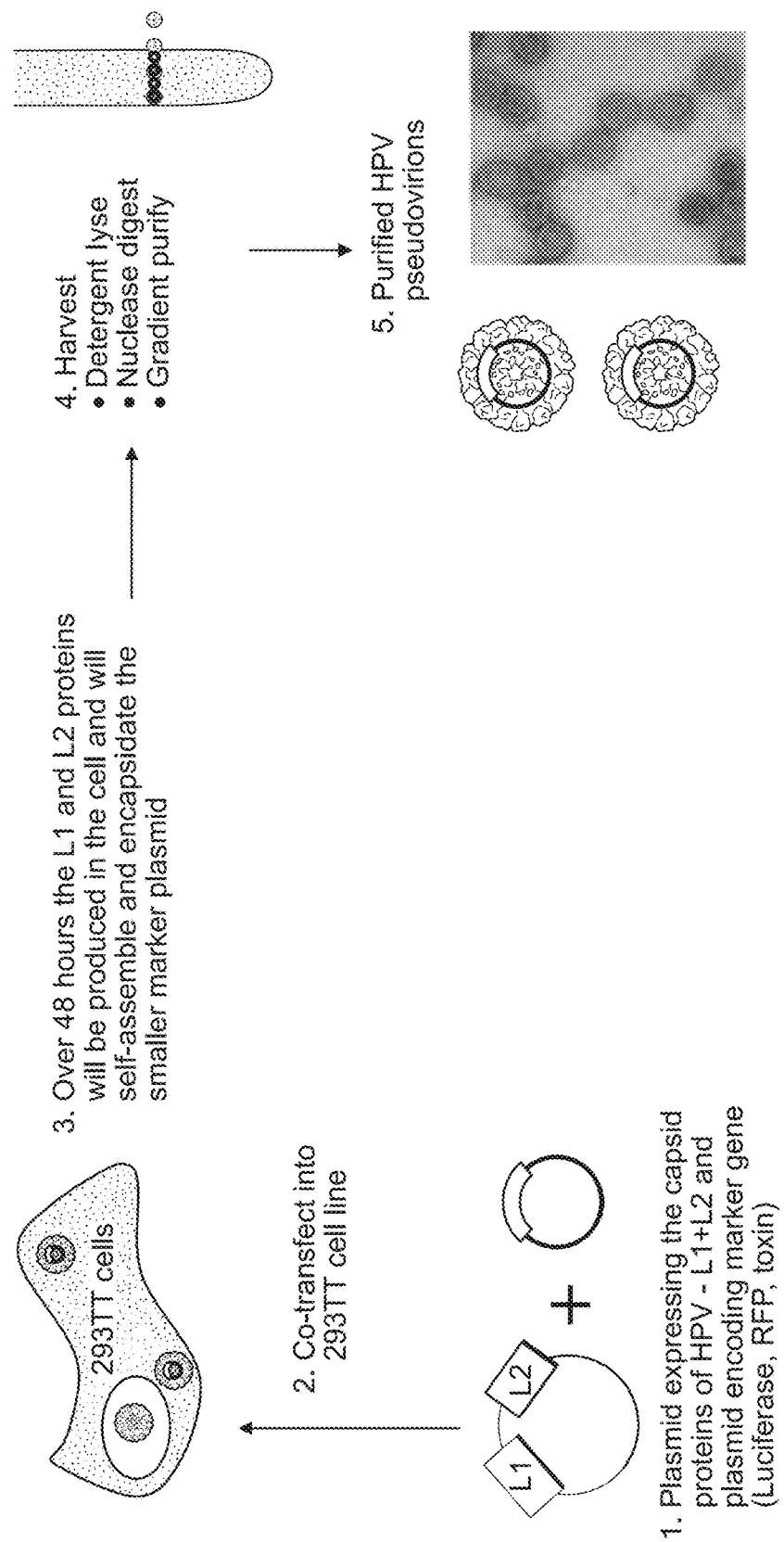

Specification includes a Sequence Listing.

(56) References Cited

U.S. PATENT DOCUMENTS

| | | |
|---|---|---|
| 2007/0243157 A1 | 10/2007 | Tanaka et al. |
| 2007/0258889 A1 | 11/2007 | Douglas et al. |
| 2009/0012022 A1 | 1/2009 | Milner et al. |
| 2009/0041671 A1 | 2/2009 | Young et al. |
| 2010/0135902 A1 | 6/2010 | Roberts et al. |
| 2011/0052496 A1 | 3/2011 | Cid-Arregui |
| 2011/0065173 A1 | 3/2011 | Kingsman et al. |
| 2011/0104051 A1 | 5/2011 | Francis et al. |
| 2012/0015899 A1 | 1/2012 | Lomonossoff et al. |
| 2012/0171290 A1 | 7/2012 | Coursaget et al. |
| 2012/0207840 A1 | 8/2012 | de los Pinos |
| 2013/0071414 A1 | 3/2013 | Dotti et al. |
| 2013/0115247 A1 | 5/2013 | de los Pinos et al. |
| 2013/0116408 A1 | 5/2013 | de los Pinos |
| 2013/0136689 A1 | 5/2013 | Rohlff et al. |
| 2014/0377170 A1 | 12/2014 | de los Pinos et al. |
| 2016/0228568 A1 | 8/2016 | de los Pinos et al. |
| 2017/0274099 A1 | 9/2017 | de los Pinos et al. |
| 2017/0368162 A1 | 12/2017 | Coursaget et al. |

FOREIGN PATENT DOCUMENTS

| | | |
|---|---|---|
| JP | 2005-527493 A | 9/2005 |
| JP | 2007-065646 A | 3/2007 |
| JP | 2009-532564 | 9/2009 |
| JP | 2012-523455 A | 10/2012 |
| WO | WO 91/03162 A1 | 3/1991 |
| WO | WO 92/07065 A1 | 4/1992 |
| WO | WO 93/15187 A1 | 8/1993 |
| WO | WO 97/26270 A2 | 7/1997 |
| WO | WO 99/15630 A1 | 4/1999 |
| WO | WO 00/09673 A1 | 2/2000 |
| WO | WO 03/008573 A2 | 1/2003 |
| WO | WO 03/061696 A2 | 7/2003 |
| WO | WO 05/051431 A1 | 6/2005 |
| WO | WO 05/086667 A2 | 9/2005 |
| WO | WO 06/125997 A1 | 11/2006 |
| WO | WO 08/048288 A2 | 4/2008 |
| WO | WO 08/054184 A1 | 5/2008 |
| WO | WO 08/103920 A2 | 8/2008 |
| WO | WO 2008/140961 A2 | 11/2008 |
| WO | WO 2010/120266 A1 | 10/2010 |
| WO | WO 2011/039646 A2 | 4/2011 |
| WO | WO 2013/080187 A1 | 6/2013 |
| WO | WO 2013/119877 A1 | 8/2013 |
| WO | WO 2014/039523 A1 | 3/2014 |
| WO | WO 2015/042325 A1 | 3/2015 |
| WO | WO 2016/139362 A1 | 9/2016 |

OTHER PUBLICATIONS

U.S. Appl. No. 13/264,213, filed Mar. 2, 2012.
U.S. Appl. No. 15/636,112, filed Jun. 28, 2017.
U.S. Appl. No. 14/376,408, filed Aug. 1, 2014.
U.S. Appl. No. 15/615,485, filed Jun. 6, 2017.
U.S. Appl. No. 15/023,169, filed Mar. 18, 2016.
PCT/US2009/005808, dated Mar. 5, 2010, International Search Report and Written Opinion.
PCT/US2009/005808, dated May 5, 2011, International Preliminary Report on Patentability.
PCT/US2009/004299, dated Sep. 24, 2010, International Search Report and Written Opinion.
PCT/US2009/004299, dated Oct. 27, 2011, International Preliminary Report on Patentability.
PCT/IB2010/002654, dated Apr. 8, 2011, Invitation to Pay Additional Fees.
PCT/IB2010/002654, dated Aug. 18, 2011, International Search Report and Written Opinion.
PCT/IB2010/002654, dated Apr. 12, 2012, International Preliminary Report on Patentability.
PCT/US2013/025230, dated Jun. 5, 2013, International Search Report and Written Opinion.
PCT/US2013/025230, dated Aug. 21, 2014, International Preliminary Report on Patentability.
PCT/US2012/063603, dated Feb. 22, 2013, International Search Report and Written Opinion.
PCT/US2012/063603, dated May 14, 2015, International Preliminary Report on Patentability.
EP 14845738.5, dated Apr. 4, 2017, Supplementary European Search Report.
PCT/US2014/056412, dated Dec. 29, 2014, International Search Report and Written Opinion.
PCT/US2014/056412, dated Mar. 31, 2016, International Preliminary Report on Patentability.
[No Author Listed] Bac-to-Bac Baculovirus Expression System. An efficient site-specific transposition system to generate baculovirus for high-level expression of recombinant proteins. Sep. 4, 2010. Retrieved from the Internet on Sep. 23, 2013. 80 pages.
Alvarez, Insertion de sequences peptidiques dans la proteine majeure de capside du papillomavirus de type 16: application au ciblage pulmonaire de vecteurs derives et a la production d'un vaccine chimerique. Thesis. Universite Francois Rabelais. Jun. 20, 2006. 203 pages.
Bergsdorf et al., Highly efficient transport of carboxyfluorescein diacetate succinimidyl ester into COS7 cells using human papillomavirus-like particles. FEBS Lett. Feb. 11, 2003;536(1-3):120-4.
Bousarghin et al., Inhibition of cervical cancer cell growth by human papillomavirus viruslike particles packaged with human papillomavirus oncoprotein short hairpin RNAs. Mol Cancer Ther. Feb. 2009;8(2):357-65. Epub Jan. 27, 2009.
Brumfield et al., Heterologous expression of the modified coat protein of Cowpea chlorotic mottle bromovirus results in the assembly of protein cages with altered architectures and function. J Gen Virol. Apr. 2004;85(Pt 4):1049-53.
Buck et al., Efficient intracellular assembly of papillomaviral vectors. J Virol. Jan. 2004;78(2):751-7.
Buck et al., Production of papillomavirus-based gene transfer vectors. Current Protocols in Cell Biology. 26.1.1-26.1.19, Dec. 2007.
Butz et al., siRNA targeting of the viral E6 oncogene efficiently kills human papillomavirus-positive cancer cells. Oncogene. Sep. 4, 2003;22(38):5938-45.
Carpentier et al. Mutations on the FG surface loop of human papillomavirus type 16 major capsid protein affect recognition by both type-specific neutralizing antibodies and cross-reactive antibodies. J Med Virol. Dec. 2005;77(4):558-65. Abstract only.
Carpentier et al., Cell targeting for CF gene therapy: Identification of a new specific cell ligand and selection of infectious papillomavirus mutants. J Cystic Fibro. Jun. 1, 2009;8:S31.
Carpentier, Retargeting human papillomavirus-mediated gene transfer to human airway epithelial cells. J Cystic Fibro. Jun. 1, 2010;9:S17.
Carter et al., Identification of a human papillomavirus type 16-specific epitope on the C-terminal arm of the major capsid protein L1. J Virol. Nov. 2003;77(21):11625-32.
Carter et al., Identification of human papillomavirus type 16 L1 surface loops required for neutralization by human sera. J Virol. May 2006;80(10):4664-72.
Christensen et al. Surface conformational and linear epitopes on HPV-16 and HPV-18 L1 virus-like particles as defined by monoclonal antibodies. Virology. Sep. 1, 1996;223(1):174-84.
Cohen et al., Targeted in vitro photodynamic therapy via aptamer-labeled, porphyrin-loaded virus capsids. J Photochem Photobiol B. Apr. 5, 2013;121:67-74. doi: 10.1016/j.jphotobiol.2013.02.013. Epub Feb. 28, 2013.
Combita et al., Gene transfer using human papillomavirus pseudovirions varies according to virus genotype and requires cell surface heparan sulfate. FEMS Microbiol Lett. Oct. 16, 2001;204(1):183-8.
Cook et al., Purification of virus-like particles of recombinant human papillomavirus type 11 major capsid protein L1 from *Saccharomyces cerevisiae*. Protein Expr Purif. Dec. 1999;17(3):477-84.
Douglas et al., Protein engineering of a viral cage for constrained nanomaterials synthesis. Adv Mater. Mar. 12, 2002;14(6):415-8.
Elbashir et al., Analysis of gene function in somatic mammalian cells using small interfering RNAs. Methods. Feb. 2002;26(2):199-213.

(56) References Cited

OTHER PUBLICATIONS

Ewers et al., GM1 structure determines SV40-induced membrane invagination and infection. Nat Cell Biol. Jan. 2010;12(1):11-20; sup pp. 1-12. doi: 10.1038/ncb1999. Epub Dec. 20, 2009.
Finnen et al., Interactions between papillomavirus L1 and L2 capsid proteins. J Virol. Apr. 2003;77(8):4818-26.
Fleury et al., Identification of neutralizing conformational epitopes on the human papillomavirus type 31 major capsid protein and functional implications. Protein Sci. Jul. 2009;18(7):1425-38.
Gaden et al., Gene transduction and cell entry pathway of fiber-modified adenovirus type 5 vectors carrying novel endocytic peptide ligands selected on human tracheal glandular cells. J Virol. Jul. 2004;78(13):7227-47.
GenBank Accession No. P03101, Major Capsid Protein L1, Jan. 11, 2011.
Gillitzer et al., Controlled ligand display on a symmetrical protein-cage architecture through mixed assembly. Small. Aug. 2006;2(8-9):962-6.
Hagensee et al. Self-assembly of human papillomavirus type 1 capsids by expression of the L1 protein alone or by coexpression of the L1 and L2 capsid proteins. Journal of virology. Jan. 1, 1993;67(1):315-22.
Jiang et al., Gel-based application of siRNA to human epithelial cancer cells induces RNAi-dependent apoptosis. Oligonucleotides. 2004 Winter;14(4):239-48.
Jiang et al., Selective silencing of viral gene E6 and E7 expression in HPV-positive human cervical carcinoma cells using small interfering RNAs. Methods Mol Biol. 2005;292:401-20.
Jiang et al., Selective silencing of viral gene expression in HPV-positive human cervical carcinoma cells treated with siRNA, a primer of RNA interference. Oncogene. Sep. 5, 2002;21(39):6041-8.
Jost et al., A novel peptide, THALWHT, for the targeting of human airway epithelia. FEBS Lett. Feb. 2, 2001;489(2-3):263-9.
Kawana et al., In vitro construction of pseudovirions of human papillomavirus type 16: incorporation of plasmid DNA into reassembled L1/L2 capsids. J Virol. Dec. 1998;72(12):10298-300.
Kines et al., Human papillomavirus capsids preferentially bind and infect tumor cells. Int J Cancer. Feb. 15, 2016;138(4):901-11. doi: 10.1002/ijc.29823. Epub Oct. 27, 2015.
Kirnbauer et al. Efficient self-assembly of human papillomavirus type 16 L1 and L1-L2 into virus-like particles. Journal of virology. Dec. 1, 1993;67(12):6929-36.
Kirnbauer et al. Papillomavirus L1 major capsid protein self-assembles into virus-like particles that are highly immunogenic. Proceedings of the National Academy of Sciences. Dec. 15, 1992;89(24):12180-4.
Lavelle et al., the disassembly, reassembly and stability of CCMV protein capsids. J Virol Methods. Dec. 2007;146(1-2):311-6. Epub Sep. 4, 2007.
Lee et al., Adaptations of nanoscale viruses and other protein cages for medical applications. Nanomedicine. Sep. 2006;2(3):137-49.
Leong et al., Intravital imaging of embryonic and tumor neovasculature using viral nanoparticles. Nat Protoc. Aug. 2010;5(8):1406-17. doi: 10.1038/nprot.2010.103. Epub Jul. 8, 2010.
Li et al, Expression of the human papillomavirus type 11 L1 capsid protein in *Escherichia coli*: characterization of protein domains involved in DNA binding and capsid assembly. J Virol. Apr. 1997;71(4):2988-95.
Li et al, Trackable and Targeted Phage as Positron Emission Tomography (PET) Agent for Cancer Imaging. Theranostics. 2011;1:371-80. Epub Nov. 18, 2011.
Mitsunaga et al., In vivo longitudinal imaging of experimental human papillomavirus infection in mice with a multicolor fluorescence mini-endoscopy system. Cancer Prev Res (Phila). May 2011;4(5):767-73. doi: 10.1158/1940-6207.CAPR-10-0334. Epub Mar. 23, 2011.
Oh et al., Enhanced mucosal and systemic immunogenicity of human papillomavirus-like particles encapsidating interleukin-2 gene adjuvant. Virology. Oct. 25, 2004;328(2):266-73.
Pedersen et al. Immunization of early adolescent females with human papillomavirus type 16 and 18 L1 virus-like particle vaccine containing AS04 adjuvant. Journal of Adolescent Health. Jun. 30, 2007;40(6):564-71.
Pinto et al. Cellular immune responses to human papillomavirus (HPV)-16 L1 in healthy volunteers immunized with recombinant HPV-16 L1 virus-like particles. Journal of Infectious Diseases. Jul. 15, 2003;188(2):327-38.
Pyeon et al., Production of infectious human papillomavirus independently of viral replication and epithelial cell differentiation. Proc Natl Acad Sci U S A. Jun. 28, 2005;102(26):9311-6. Epub Jun. 15, 2005.
Raja et al., Hybrid virus-polymer materials. 1. Synthesis and properties of PEG-decorated cowpea mosaic virus. Biomacromolecules. May-Jun. 2003;4(3):472-6.
Rose et al. Expression of human papillomavirus type 11 L1 protein in insect cells: in vivo and in vitro assembly of viruslike particles. Journal of Virology. Apr. 1, 1993;67(4):1936-44.
Ryding et al., Deletion of a major neutralizing epitope of human papillomavirus type 16 virus-like particles. J Gen Virol. Mar. 2007;88(Pt 3):792-802.
Sadeyen et al., Insertion of a foreign sequence on capsid surface loops of human papillomavirus type 16 virus-like particles reduces their capacity to induce neutralizing antibodies and delineates a conformational neutralizing epitope. Virology. Apr. 25, 2003;309(1):32-40.
Schädlich et al., Refining HPV 16 L1 purification from *E. coli*: reducing endotoxin contaminations and their impact on immunogenicity. Vaccine. Mar. 4, 2009;27(10):1511-22. Epub Jan. 25, 2009.
Singh, Tumor targeting using canine parvovirus nanoparticles. Curr Top Microbiol Immunol. 2009;327:123-41.
Speir et al., Structures of the native and swollen forms of cowpea chlorotic mottle virus determined by X-ray crystallography and cryo-electron microscopy. Structure. Jan. 15, 1995;3(1):63-78.
Stephanopoulos et al., Dual-surface modified virus capsids for targeted delivery of photodynamic agents to cancer cells. ACS Nano. Oct. 26, 2010;4(10):6014-20. doi: 10.1021/nn1014769.
Touze et al., In vitro gene transfer using human papillomavirus-like particles. Nucleic Acids Res. Mar. 1, 1998;26(5):1317-23.
Touze et al., The L1 major capsid protein of human papillomavirus type 16 variants affects yield of virus-like particles produced in an insect cell expression system. J Clin Microbiol. Jul. 1998;36(7):2046-51.
Touze et al., The nine C-terminal amino acids of the major capsid protein of the human papillomavirus type 16 are essential for DNA binding and gene transfer capacity. FEMS Microbiol Lett. Aug. 1, 2000;189(1):121-7.
Uchida et al., Biological Containers: Protein Cages as Multifunctional Nanoplatforms. Adv Mater. 2007;19:1025-42.
Varsani et al., Chimeric human papillomavirus type 16 (HPV-16) L1 particles presenting the common neutralizing epitope for the L2 minor capsid protein of HPV-6 and HPV-16. J Virol. Aug. 2003;77(15):8386-93.
Vaysse et al., Improved transfection using epithelial cell line-selected ligands and fusogenic peptides. Biochim Biophys Acta. Jul. 26, 2000;1475(3):369-76.
Wang et al., Insertion of a targeting peptide on capsid surface loops of human papillomavirus type-16 virus-like particles mediate elimination of anti-dsDNA Abs-producing B cells with high efficiency. J Immunother. Jan. 2009;32(1):36-41.
Wang et al., Expression of Human Papillomavirus Type 6 L1 and L2 Isolated in China and Self Assembly of Virus-like Particles by the Products. Acta Biochimica et Biophysica Sinica. 2003; 35(1):27-34. 10 pages.
Wang et al., Human papillomavirus type 6 virus-like particles present overlapping yet distinct conformational epitopes. J Gen Virol. Jun. 2003;84(Pt 6):1493-7.
White et al., Genetic modification of adeno-associated viral vector type 2 capsid enhances gene transfer efficiency in polarized human airway epithelial cells. Hum Gene Ther. Dec. 2008;19(12):1407-14.
Willits et al., Effects of the cowpea chlorotic mottle bromovirus beta-hexamer structure on virion assembly. Virology. Feb. 15, 2003;306(2):280-8.

(56) References Cited

OTHER PUBLICATIONS

Xu et al., Papillomavirus virus-like particles as vehicles for the delivery of epitopes or genes. Arch Virol. Nov. 2006;151(11):2133-48. Epub Jun. 22, 2006.
Yoshinouchi et al., In vitro and in vivo growth suppression of human papillomavirus 16-positive cervical cancer cells by E6 siRNA. Mol Ther. Nov. 2003;8(5):762-8.
Zhang et al. Expression of Human Papillomavirus Type 16 L1 Protein in *Escherichia coli*: Denaturation, Renaturation, and Self-Assembly of Virus-like Particlesin Vitro. Virology. Apr. 10, 1998;243(2):423-31.
Zhou et al. Expression of vaccinia recombinant HPV 16 L1 and L2 ORF proteins in epithelial cells is sufficient for assembly of HPV virion-like particles. Virology. Nov. 1, 1991;185(1):251-7.
Peng et al., Construction and production of fluorescent papillomavirus-like particles. J Tongji Med Univ. 1999;19(3):170-4, 180.
Rhee et al., Glycan-targeted virus-like nanoparticles for photodynamic therapy. Biomacromolecules. Aug. 13, 2012;13(8):2333-8. doi: 10.1021/bm300578p. Epub Jul. 24, 2012. Author manuscript.
Rudolf et al., Human dendritic cells are activated by chimeric human papillomavirus type-16 virus-like particles and induce epitope-specific human T cell responses in vitro. J Immunol. May 15, 2001;166(10):5917-24.

* cited by examiner

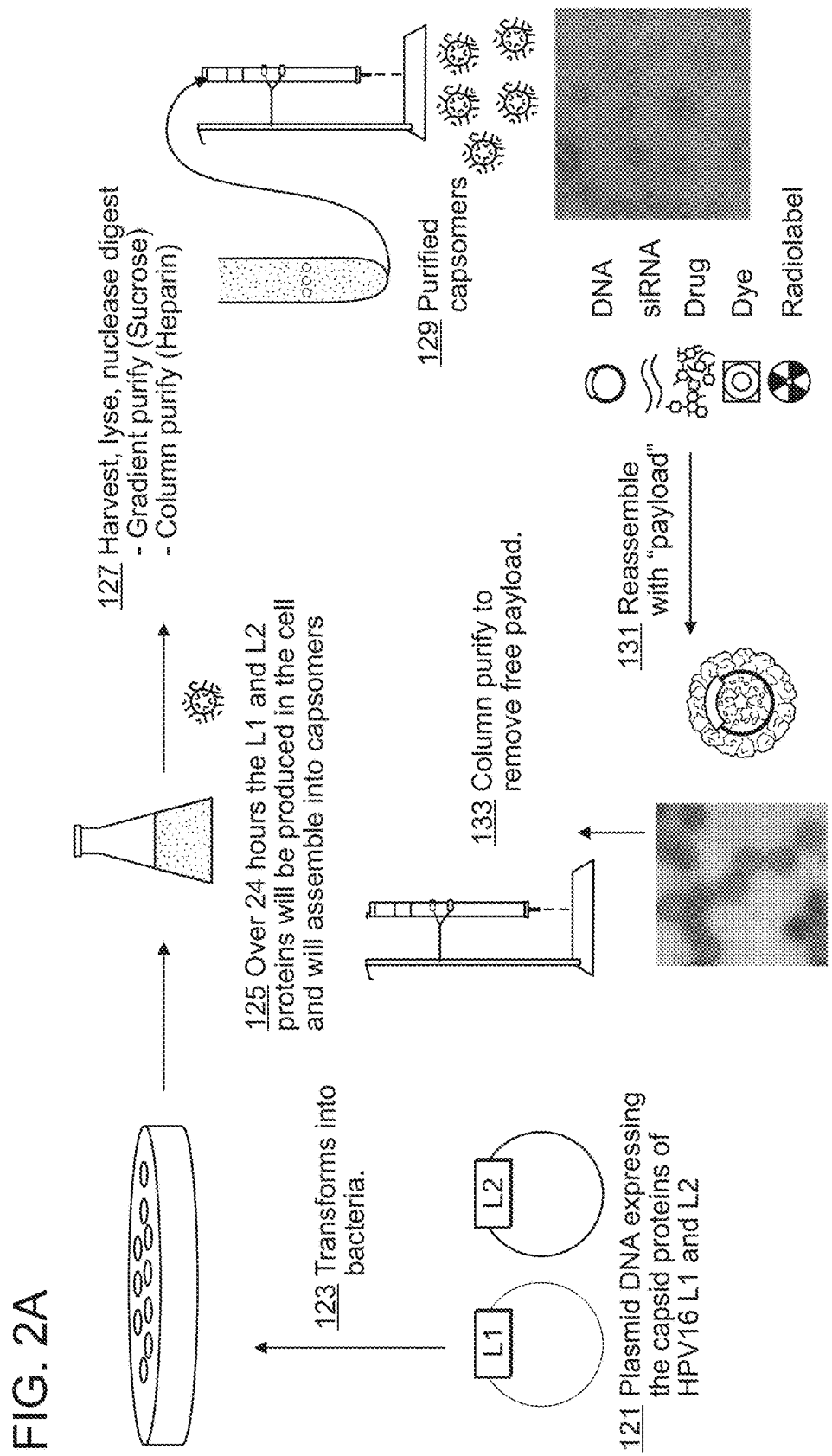

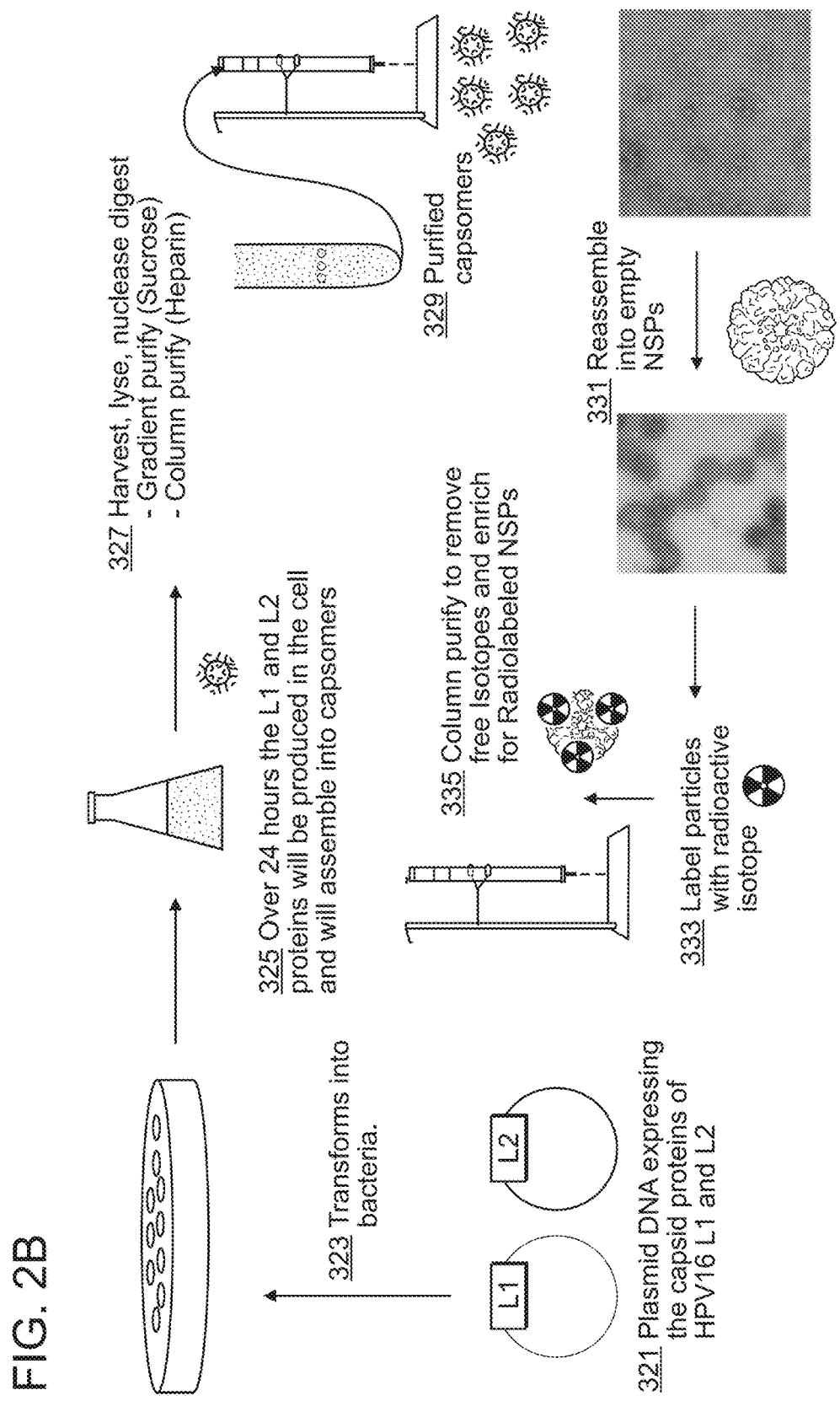

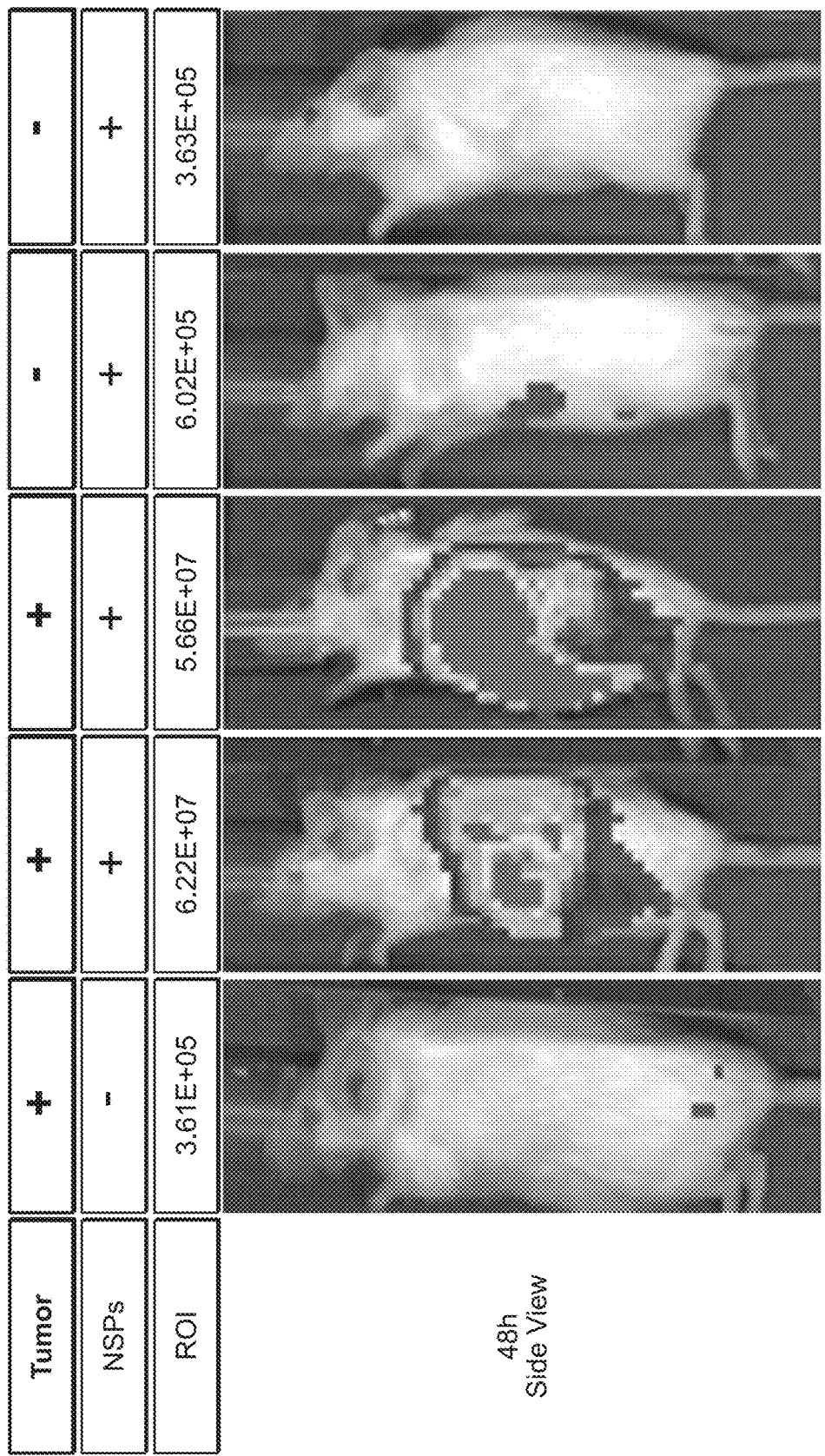

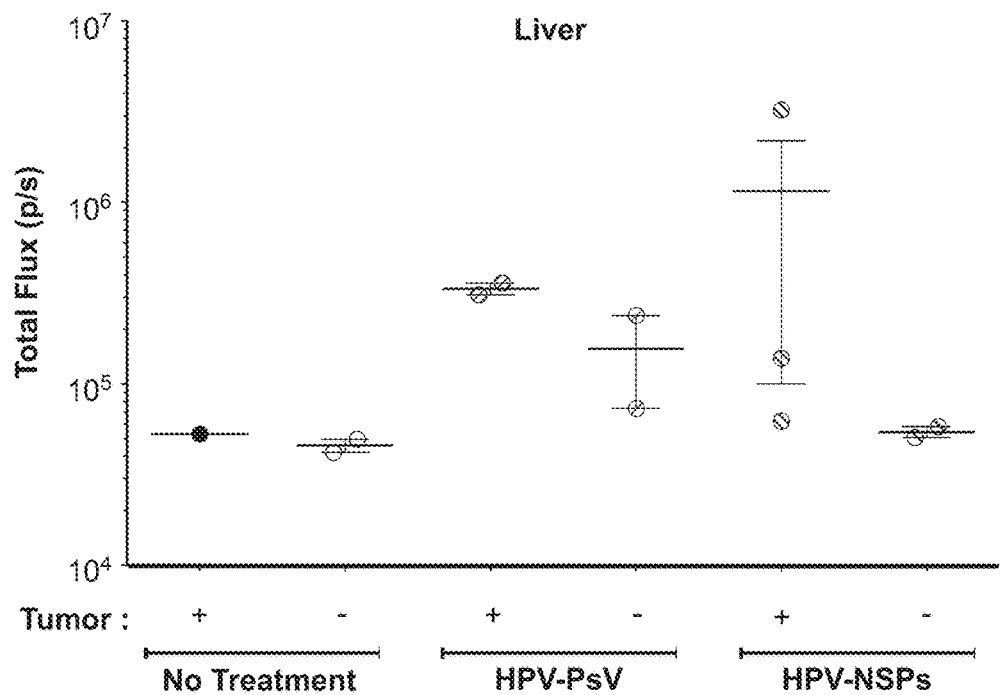
FIG. 6E Ovarian orthotopic SKOV-3 model
Particle Biodistribution as determined by delivery of a luminescent reporter gene

FIG. 7

SEQ ID NO: 1

Plasmid p16L1*L2 encoding mutant L1 (L1*) and L2 human codon optimized

```
   1 CTAGAGCCAC CATGAGCCTG TGGCTGCCCA GCGAGGCCAC CGTGTACCTG CCCCCCGTGC
  61 CCGTGAGCAA GGTGGTGAGC ACCGACGAGT ACGTGGCCAG GACCAACATC TACTACCACG
 121 CCGGCACCAG CAGGCTGCTG GCCGTGGGCC ACCCCTACTT CCCCATCAAG AAGCCCAACA
 181 ACAACAAGAT CCTGGTGCCC AAGGTGAGCG GCCTGCAGTA CAGGGTGTTC AGGATCCACC
 241 TGCCCGACCC CAACAAGTTC GGCTTCCCCG ACACCAGCTT CTACAACCCC GACACCCAGA
 301 GGCTGGTGTG GGCCTGCGTG GGCGTGGAGG TGGGCAGGGG CCAGCCCCTG GGCGTGGGCA
 361 TCAGCGGCCA CCCCCTGCTG AACAAGCTGG ACGACACCGA GAACGCCAGC GCCTACGCCG
 421 CCAACGCCGG CGTGGACAAC AGGGAGTGCA TCAGCATGGA CTACAAGCAG ACCCAGCTGT
 481 GCCTGATCGG CTGCAAGCCC CCCATCGGCG AGCACTGGGG CAAGGGCAGC CCCTGCACCA
 541 ACGTGGCCGT GAACCCCGGC GACTGCCCCC CCTGGAGCT GATCAACACC GTGATCCAGG
 601 ACGGCGACAT GGTGGACACC GGCTTCGGCG CCATGGACTT CACCACCCTG CAGGCCAACA
 661 AGAGCGAGGT GCCCCTGGAC ATCTGCACCA GCATCTGCAA GTACCCCGAC TACATCAAGA
 721 TGGTGAGCGA GCCCTACGGC GACAGCCTGT TCTTCTACCT GAGGAGGGAG CAGATGTTCG
 781 TGAGGCACCT GTTCAACAGG GCCGGCGCCG TGGGCGAGAA CGTGCCCACC GACCTGTACA
 841 TCAAGGGCAG CGGCAGCACC GCCACCCTGG CCAACAGCAA CTACTTCCCC ACCCCCAGCG
 901 GCAGCATGGT GACCAGCGAC GCCCAGATCT TCAACAAGCC CTACTGGCTG CAGAGGGCCC
 961 AGGGCCACAA CAACGGCATC TGCTGGGGCA ACCAGCTGTT CGTGACCGTG GTGGACACCA
1021 CCAGGAGCAC CAACATGAGC CTGTGCGCCG CCATCACCAC CAGCGAGACC ACCTACAAGA
1081 ACACCAACTT CAAGGAGTAC CTGAGGCACG GCGAGGAGTA CGACCTGCAG TTCATCTTCC
1141 AGCTGTGCAA GATCACCCTG ACCGCCGACG TGATGACCTA CATCCACAGC ATGAACAGCA
1201 CCATCCTGGA GGACTGGAAC TTCGGCCTGC AGCCCCCCCC CGGCGGCACC CTGGAGGACA
1261 CCTACAGGTT CGTGACCAGC CAGGCCATCG CCTGCCAGAA GCACACCCCC CCGCCCCA
1321 AGGAGGACCC CCTGAAGAAG TACACCTTCT GGGAGGTGAA CCTGAAGGAG AAGTTCAGCG
1381 CCGACCTGGA CCAGTTCCCC CTGGGCAGGA AGTTCCTGCT GCAGGCCGGC CTGAAGGCCA
1441 AGCCCAAGTT CACCCTGGGC AAGAGGAAGG CCACCCCCAC CACCAGCAGC ACCAGCACCA
1501 CCGCCAAGAG GAAGAAGAGG AAGCTGTGAA AGCTTATCGA TACCGTCGAC CTCGACCTGC
1561 AGAAGCTTAA AACAGCTCTG GGGTTGTACC CACCCCAGAG GCCCACGTGG CGGCTAGTAC
1621 TCCGGTATTG CGGTACCCTT GTACGCCTGT TTTATACTCC CTTCCCGTAA CTTAGACGCA
1681 CAAAACCAAG TTCAATAGAA GGGGGTACAA ACCAGTACCA CCACGAACAA GCACTTCTGT
1741 TTCCCCGGTG ATGTCGTATA GACTGCTTGC GTGGTTGAAA GCGACGGATC CGTTATCCGC
1801 TTATGTACTT CGAGAAGCCC AGTACCACCT CGGAATCTTC GATGCGTTGC GCTCAGCACT
1861 CAACCCCAGA GTGTAGCTTA GGCTGATGAG TCTGGACATC CCTCACCGGT GACGGTGGTC
1921 CAGGCTGCGT TGGCGGCCTA CCTATGGCTA ACGCCATGGG ACGCTAGTTG TGAACAAGGT
1981 GTGAAGAGCC TATTGAGCTA CATAAGAATC CTCCGGCCCC TGAATGCGGC TAATCCCAAC
2041 CTCGGAGCAG GTGGTCACAA ACCAGTGATT GGCCTGTCGT AACGGCCAAG TCCGTGGCGG
2101 AACCGACTAC TTTGGGTGTC CGTGTTTCCT TTTATTTTAT TGTGGCTGCT TATGGTGACA
2161 ATCACAGATT GTTATCATAA AGCGAATTGG ATTGCGGCCG CTCTAGAGCC ACCATGAGGC
2221 ACAAGAGGAG CGCCAAGAGG ACCAAGAGGG CCAGCGCCAC CCAGCTGTAC AAGACCTGCA
2281 AGCAGGCCGG CACCTGCCCC CCGACATCA TCCCCAAGGT GGAGGGCAAG ACCATCGCCG
2341 ACCAGATCCT GCAGTACGGC AGCATGGGCG TGTTCTTCGG CGGCCTGGGC ATCGGCACCG
2401 GCAGCGGCAC CGGCGGCAGG ACCGGCTACA TCCCCCTGGG CACCAGGCCC CCCACCGCCA
2461 CCGACACCCT GGCCCCCGTG AGGCCCCCC TGACCGTGGA CCCCGTGGGC CCCAGCGACC
2521 CCAGCATCGT GAGCCTGGTG GAGGAGACCA GCTTCATCGA CGCCGGCGCC CCCACCAGCG
2581 TGCCCAGCAT CCCCCCCGAC GTGAGCGGCT TCAGCATCAC CACCAGCACC GACACCACCC
2641 CCGCCATCCT GGACATCAAC AACACCGTGA CCACCGTGAC CACCCACAAC AACCCCACCT
2701 TCACCGACCC CAGCGTGCTG CAGCCCCCCA CCCCGCCGA GACCGGCGGC CACTTCACCC
2761 TGAGCAGCAG CACCATCAGC ACCCACAACT ACGAGGAGAT CCCCATGGAC ACCTTCATCG
2821 TGAGCACCAA CCCCAACACC GTGACCAGCA GCACCCCCAT CCCCGGCAGC AGGCCCGTGG
2881 CCAGGCTGGG CCTGTACAGC AGGACCACCC AGCAGGTGAA GGTGGTGGAC CCCGCCTTCG
2941 TGACCACCCC CACCAAGCTG ATCACCTACG ACAACCCCGC CTACGAGGGC ATCGACGTGG
3001 ACAACACCCT GTACTTCAGC AGCAACGACA ACAGCATCAA CATCGCCCCC GACCCCGACT
3061 TCCTGGACAT CGTGGCCCTG CACAGGAGCG CAGGAGCC GGCATCAGGT
3121 ACAGCAGGAT CGGCAACAAG CAGACCCTGA GGACCAGGAG CGGCAAGAGC ATCGGCGCCA
3181 AGGTGCACTA CTACTACGAC CTGAGCACCA TCGACCCCGC CGAGGAGATC GAGCTGCAGA
3241 CCATCACCCC CAGCACCTAC ACCACCACCA GCCACGCCGC CAGCCCCACC AGCATCAACA
3301 ACGGCCTGTA CGACATCTAC GCCGACGACT TCATCACCGA CACCAGCACC ACCCCCGTGC
3361 CCAGCGTGCC CAGCACCAGC CTGAGCGGCT ACATCCCCGC CAACACCACC ATCCCCTTCG
3421 GTGGCGCCTA CAACATCCCC CTGGTGAGCG GCCCCGACAT CCCCATCAAC ATCACCGACC
3481 AGGCCCCCAG CCTGATCCCC ATCGTGCCCG GCAGCCCCCA GTACACCATC ATCGCCGACG
3541 CCGGCGACTT CTACCTGCAC CCCAGCTACT ACATGCTGAG GAAGAGGAGG AAGAGGCTGC
3601 CCTACTTCTT CAGCGACGTG AGCCTGGCCG CCTGAAAGCT TTTTGAATTC TTTGGATCCA
3661 CTAGTGGATC CCCCGGGCTG CAGGAATTCG ATATCAAGCT TATCGATAAT CAACCTCTGG
3721 ATTACAAAAT TTGTGAAAGA TTGACTGGTA TTCTTAACTA TGTTGCTCCT TTTACGCTAT
3781 GTGGATACGC TGCTTTAATG CCTTTGTATC ATGCTATTGC TTCCCGTATG GCTTTCATTT
3841 TCTCCTCCTT GTATAAATCC TGGTTGCTGT CTCTTTATGA GGAGTTGTGG CCCGTTGTCA
3901 GGCAACGTGG CGTGGTGTGC ACTGTGTTTG CTGACGCAAC CCCCACTGGT TGGGGCATTG
3961 CCACCACCTG TCAGCTCCTT TCCGGGACTT TCGCTTTCCC CCTCCCTATT GCCACGGCGG
4021 AACTCATCGC CGCCTGCCTT GCCCGCTGCT GGACAGGGGC TCGGCTGTTG GGCACTGACA
4081 ATTCCGTGGT GTTGTCGGGG AAATCATCGT CCTTTCCTTG GCTGCTCGCC TGTGTTGCCA
```

FIG. 7 (continued)

```
4141 CCTGGATTCT GCGCGGGACG TCCTTCTGCT ACGTCCCTTC GGCCCTCAAT CCAGCGGACC
4201 TTCCTTCCCG CGGCCTGCTG CCGGCTCTGC GGGCTCTTCC GCGTCTTCGC CTTCGCCCTC
4261 AGACGAGTCG GATCTCCCTT TGGGCCGCCT CCCCGCATCG ATACCGTCGG CCCGTTTAAA
4321 CCCGCTGATC AGCCTCGACT GTGCCTTCTA GTTGCCAGCC ATCTGTTGTT TGCCCCTCCC
4381 CCGTGCCTTC CTTGACCCTG GAAGGTGCCA CTCCCACTGT CCTTTCCTAA TAAAATGAGG
4441 AAATTGCATC GCATTGTCTG AGTAGGTGTC ATTCTATTCT GGGGGGTGGG GTGGGGCAGG
4501 ACAGCAAGGG GGAGGATTGG GAAGACAATA GCAGGCATGC TGGGGATGCG GTGGGCTCTA
4561 TGGCTTCTGA GGCGGAAAGA ACCAGCTGGG GCTCTAGGGG GTATCCCCAC GCCGCCTGTA
4621 GCGGCGCATT AAGCGCGGCG GGTGTGGTGG TTACGCGCAG CGTGACCGCT ACACTTGCCA
4681 GCGCGCTAGC GCCCGCTCCT TTCGCTTTCT TCCCTTCCTT TCTCGCCACG TTCGCCGGCT
4741 TTCCCCGTCA AGCTCTAAAT CGGGGGCTCC CTTTAGGGTT CCGATTTAGT GCTTTACGGC
4801 ACCTCGACCC CAAAAAACTT GATTAGGGTG ATGGTTCACG TAGTGGGCCA TCGCCCTGAT
4861 AGACGGTTTT TCGCCCTTTG ACGTTGGAGT CCACGTTCTT TAATAGTGGA CTCTTGTTCC
4921 AAACTGGAAC AACACTCAAC CCTATCTCGG TCTATTCTTT TGATTTATAA GGGATTTTGC
4981 CGATTTCGGC CTATTGGTTA AAAAATGAGC TGATTTAACA AAAATTTAAC GCGAATTAAT
5041 TCTGTGGAAT GTGTGTCAGT TAGGGTGTGG AAAGTCCCCA GGCTCCCCAG CAGGCAGAAG
5101 TATGCAAAGC ATGCAGAATT CTATCAAATA TTTAAAGAAA AAAAAATTGT ATCAACTTTC
5161 TACAATCTCT TTCAGAAGAC AGAAGCAGAG GGAATACTTC CTAAATCATT CAACTAGGGC
5221 AGCATTACCT TAATACCGGA ACTAGAAAAT GACATTACAA GAAAAGAAAA CAACAGACCA
5281 ATATCTCTCA TGAACAAAGA TACAAACATT TTCAACAAAA TATTAGCAAA AAGAATCCAA
5341 GAATGTATCA AAAAATATAC ACCACAACCA AGTAGAATTT ATTCCAGATA TGTAAGGGTG
5401 GTTCAACGTT TGAAAATCAA TTAACGTAAT TTGTCCCATC AACAGGTTAA AGAAGAAAAT
5461 CACATGGTCA TATTGATAGA CACAGAAAAA GCATTTGACA AAATTTAACA CCCATTCATG
5521 ATGCAATCTC TCAGTAAACT AGGAATAGAG GAAAACTTCC TCAGCTTGAA TGTACCTTCC
5581 TCTCAATTTT GCTATGAACC TGAAACTCCT CTTAAAAAAT AAAGTTTTTC ATTTAAAAAG
5641 AAAACAAAAA ACATGGAGGA GCGTTGATGT ATCTCATTTT AGACCAATCA GCTATGGATA
5701 GTTAGGCGAC AGCACAGATA GCTGCTGTAC TTCTGTTTCT GGCAATGTTC CAGACTACAT
5761 TTAAAAAATT TTTAATTATA GACTTGTACT TAATGTTCAA GAAAAATATG AAAATGGCTT
5821 TGCCGTGTTA ATGCTACTCT TTTTTAAAAA AAACTAAAGT TCAAACTTTA TTTATATTTC
5881 ATTAGTTTTT TAGCTACTGT TCTTTTTCTG TTCTGGGATC TCATTCAGAA TGCCACATTA
5941 CATATAATTC TCATGTCTCC TTGGGTTCCT CTTAGTTTTG ACAGTTCCTC AGACTTTTCT
6001 TATTTTTGAT GACCTTGACA GTTTTGAGGA GTACTGGTTA GATATAGGGT AATGGTTTTT
6061 AAAGTATATT TGTCATGATT TATACTGGGG TAAGGGTTTG GGGAGGAAGC CCATGGGGTA
6121 AAGTACTGTT CTCATCACAT CATATCAAGG TTATATACCA TCAATATTGC CACAGATGTT
6181 ACTTAGCCTT TTAATATTTC TCTAATTTAG TGTATATGCA ATGATAGTTC TCTGATTTCT
6241 GAGATTGAGT TTCTCATGTG TAATGATTAT TTAGAGTTTC TCTTTCATCT GTTCAAATTT
6301 TTGTCTAGTT TTATTTTTTA CTGATTTGTA AGACTTCTTT TTATAATCTG CATATTACAA
6361 TTCTCTTTAC TGGGGTGTTG CAAATATTTT CTGTCATTCT ATGGCCTGAC TTTTCTTAAT
6421 GGTTTTTTAA TTTTAAAAAT AAGTCTTAAT ATTCATGCAA TCTAATTAAC AATCTTTTCT
6481 TTGTGGTTAC GACTTTGAGT CATAAGAAAT TTTTCTCTAC ACTGAAGTCA TGATGGCATG
6541 CTTCTATATT ATTTTCTAAA AGATTTAAAG TTCCATTAGA CTCATTAAGA CTTATAATTC
6601 ACTGGAATTT TTTTGTGTGT ATGGTATGAC ATATGGGTTC CCTTTTATTT TTTACATATA
6661 AATATATTTC CCTGTTTTTC TAAAAAAGAA AAAGATCATC ATTTTCCCAT TGTAAAATGC
6721 CATATTTTTT TCATAGGTCA CTTACATATA TCAATGGGTC TGTTTCTGAG CTCTACTCTA
6781 TTTTATCGCT CTCACTGTCT ATCCCCACAC ATCTCATGCT TTGCTCTAAA TCTTTGATATT
6841 TAGTGGAACA TTCTTTCCCA TTTTGTTCTA CAAGAATATT TTTGTTATTG TCTTTTGGGC
6901 TTCTATATAC ATTTTAGAAT GAGGTTGGCA AGTTAACAAA CAGCTTTTTT GGGGTGAACA
6961 TATTGACTAC AAATTTATGT GGAAAGAAAG TACCAAGTTG ACCAGTGCCG TTCCGGTGCT
7021 CACCGCGCGC GACGTCGCCG GAGCGGTCGA GTTCTGGACC GACCGGCTCG GGTTCTCCCG
7081 GGACTTCGTG GAGGACGACT TCGCCGGTGT GGTCGGGGAC GACGTGACCC TGTTCATCAG
7141 CGCGGTCCAG GACCAGGTGG TGCCGGACAA CACCCTGGCC TGGGTGTGGG TGCGCGGCCT
7201 GGACGAGCTG TACGCCGAGT GGTCGGAGGT CGTGTCCACG AACTTCCGGG ACGCCTCCGG
7261 GCCGGCCATG ACCGAGATCG GCGAGCAGCC GTGGGGGCGG GAGTTCGCCC TGCGCGACCC
7321 GGCCGGCAAC TGCGTGCACT TCGTGGCCGA GGAGCAGGAC TGACACGTGC TACGAGATTT
7381 CGATTCCACC GCCGCCTTCT ATGAAAGGTT GGGCTTCGGA ATCGTTTTCC GGGACGCCGG
7441 CTGGATGATC CTCCAGCGCG GGGATCTCAT GCTGGAGTTC TTCGCCCACC CCAACTTGTT
7501 TATTGCAGCT TATAATGGTT ACAAATAAAG CACAAATTTC ACAAATAAAGC
7561 ATTTTTTTCA CTGCATTCTA GTTGTGGTTT GTCCAAACTC ATCAATGTAT CTTATCATGT
7621 CTGTATACCG TCGACCTCTA GCTAGAGCTT GGCGTAATCA TGGTCATAGC TGTTTCCTGT
7681 GTGAAATTGT TATCCGCTCA CAATTCCACA CAACATACGA GCCGGAAGCA TAAAGTGTAA
7741 AGCCTGGGGT GCCTAATGAG TGAGCTAACT CACATTAATT GCGTTGCGCT CACTGCCCGC
7801 TTTCCAGTCG GGAAACCTGT CGTGCCAGCT GCATTAATGA ATCGGCCAAC GCGCGGGGAG
7861 AGGCGGTTTG CGTATTGGGC GCTCTTCCGC TTCCTCGCTC ACTGACTCGC TGCGCTCGGT
7921 CGTTCGGCTG CGGCGAGCGG TATCAGCTCA CTCAAAGGCG GTAATACGGT TATCCACAGA
7981 ATCAGGGGAT AACGCAGGAA AGAACATGTG AGCAAAAGGC CAGCAAAAGC CCAGGAACCG
8041 TAAAAAGGCC GCGTTGCTGG CGTTTTTCCA TAGGCTCCGC CCCCCTGACG AGCATCACAA
8101 AAATCGACGC TCAAGTCAGA GGTGGCGAAA CCCGACAGGA CTATAAAGAT ACCAGGCGTT
8161 TCCCCCTGGA AGCTCCCTCG TGCGCTCTCC TGTTCCGACC CTGCCGCTTA CCGGATACCT
8221 GTCCGCCTTT CTCCCTTCGG GAAGCGTGGC GCTTTCTCAT AGCTCACGCT GTAGGTATCT
8281 CAGTTCGGTG TAGGTCGTTC GCTCCAAGCT GGGCTGTGTG CACGAACCCC CCGTTCAGCC
8341 CGACCGCTGC GCCTTATCCG GTAACTATCG TCTTGAGTCC AACCCGGTAA GACACGACTT
8401 ATCGCCACTG GCAGCAGCCA CTGGTAACAG GATTAGCAGA GCGAGGTATG TAGGCGGTGC
8461 TACAGAGTTC TTGAAGTGGT GGCCTAACTA CGGCTACACT AGAAGAACAG TATTTGGTAT
8521 CTGCGCTCTG CTGAAGCCAG TTACCTTCGG AAAAAGAGTT GGTAGCTCTT GATCCGGCAA
8581 ACAAACCACC GCTGGTAGCG GTTTTTTTGT TTGCAAGCAG CAGATTACGC GCAGAAAAAA
8641 AGGATCTCAA GAAGATCCTT TGATCTTTTC TACGGGGTCT GACGCTCAGT GGAACGAAAA
8701 CTCACGTTAA GGGATTTTGG TCATGAGATT ATCAAAAAGG ATCTTCACCT AGATCCTTTT
```

FIG. 7 (continued)

```
 8761 AAATTAAAAA TGAAGTTTTA AATCAATCTA AAGTATATAT GAGTAAACTT GGTCTGACAG
 8821 TTACCAATGC TTAATCAGTG AGGCACCTAT CTCAGCGATC TGTCTATTTC GTTCATCCAT
 8881 AGTTGCCTGA CTCCCCGTCG TGTAGATAAC TACGATACGG GAGGGCTTAC CATCTGGCCC
 8941 CAGTGCTGCA ATGATACCGC GAGACCCACG CTCACCGGCT CCAGATTTAT CAGCAATAAA
 9001 CCAGCCAGCC GGAAGGGCCG AGCGCAGAAG TGGTCCTGCA ACTTTATCCG CCTCCATCCA
 9061 GTCTATTAAT TGTTGCCGGG AAGCTAGAGT AAGTAGTTCG CCAGTTAATA GTTTGCGCAA
 9121 CGTTGTTGCC ATTGCTACAG GCATCGTGGT GTCACGCTCG TCGTTTGGTA TGGCTTCATT
 9181 CAGCTCCGGT TCCCAACGAT CAAGGCGAGT TACATGATCC CCCATGTTGT GCAAAAAAGC
 9241 GGTTAGCTCC TTCGTCCTC CGATCGTTGT CAGAAGTAAG TTGGCCGCAG TGTTATCACT
 9301 CATGGTTATG GCAGCACTGC ATAATTCTCT TACTGTCATG CCATCCGTAA GATGCTTTTC
 9361 TGTGACTGGT GAGTACTCAA CCAAGTCATT CTGAGAATAG TGTATGCGGC GACCGAGTTG
 9421 CTCTTGCCCG GCGTCAATAC GGGATAATAC CGCGCCACAT AGCAGAACTT TAAAAGTGCT
 9481 CATCATTGGA AAACGTTCTT CGGGGCGAAA ACTCTCAAGG ATCTTACCGC TGTTGAGATC
 9541 CAGTTCGATG TAACCCACTC GTGCACCCAA CTGATCTTCA GCATCTTTTA CTTTCACCAG
 9601 CGTTTCTGGG TGAGCAAAAA CAGGAAGGCA AAATGCCGCA AAAAAGGGAA TAAGGGCGAC
 9661 ACGGAAATGT TGAATACTCA TACTCTTCCT TTTTCAATAT TATTGAAGCA TTTATCAGGG
 9721 TTATTGTCTC ATGAGCGGAT ACATATTTGA ATGTATTTAG AAAAATAAAC AAATAGGGGT
 9781 TCCGCGCACA TTTCCCCGAA AAGTGCCACC TGACGTCGAC GGATCGGGAG ATCTCCCGAT
 9841 CCCCTATGGT GCACTCTCAG TACAATCTGC TCTGATGCCG CATAGTTAAG CCAGTATCTG
 9901 CTCCCTGCTT GTGTGTTGGA GGTCGCTGAG TAGTGCGCGA GCAAAATTTA AGCTACAACA
 9961 AGGCAAGGCT TGACCGACAA TTGCATGAAG AATCTGCTTA GGGTTAGGCG TTTTGCGCTG
10021 CTTCGCGATG TACGGGCCAG ATATACGCGT TGACATTGAT TATTGACTAG TTATTAATAG
10081 TAATCAATTA CGGGGTCATT AGTTCATAGC CCATATATGG AGTTCCGCGT TACATAACTT
10141 ACGGTAAATG GCCCGCCTGG CTGACCGCCC AACGACCCCC GCCCATTGAC GTCAATAATG
10201 ACGTATGTTC CCATAGTAAC GCCAATAGGG ACTTTCCATT GACGTCAATG GGTGGAGTAT
10261 TTACGGTAAA CTGCCCACTT GGCAGTACAT CAAGTGTATC ATATGCCAAG TACGCCCCCT
10321 ATTGACGTCA ATGACGGTAA ATGGCCCGCC TGGCATTATG CCCAGTACAT GACCTTATGG
10381 GACTTTCCTA CTTGGCAGTA CATCTACGTA TTAGTCATCG CTATTACCAT GGTGATGCGG
10441 TTTTGGCAGT ACATCAATGG GCGTGGATAG CGGTTTGACT CACGGGGATT TCCAAGTCTC
10501 CACCCCATTG ACGTCAATGG GAGTTTGTTT TGGAACCAAA ATCAACGGGA CTTTCCAAAA
10561 TGTCGTAACA ACTCCGCCCC ATTGACGCAA ATGGGCGGTA GGCGTGTACG GTGGGAGGTC
10621 TATATAAGCA GAGCTCTCCC TATCAGTGAT AGAGATCTCC CTATCAGTGA TAGAGATCGT
10681 CGACGAGCTC GTTTAGTGAA CCGTCAGATC GCCTGGAGAC GCCATCCACG CTGTTTTGAC
10741 CTCCATAGAA GACACCGGGA CCGATCCAGC CTCCGGACTC TAGCGTTTAA ACTTAAGGCT
10801 AGAGTACTTA ATACGACTCA CTATAGG
```

FIG. 8A

SEQ ID NO: 2

HPVL1-mutant DNA sequence (human codon optimized)

```
atgagcctgtggctgccaagcgagggccaccgtgtacctgccccccgtgagcaag
gtggtgagcaccgacgagtacgtgcagcgaaccatctactaccacgccgaccagc
agactgctggccgtgggccaccccctactttcccatcaagaagccaacaacaagatc
ctggtgcccaaggtgagcggcctgcagtacagagttcagatccaactgcccgaccc
aacaagttcggcttccccgacaccagcttctacaacccagacacccagcggctgtgg
gctgcgtgggcgtggaggtgggcagaggccagcccctgggcgtgggcatcagcggccac
cccctgctgaacaagctggacgacaccgagaacgccagcgcctacgccgccaacgccggc
```

FIG. 8B gtggacaacagagagtgcatcagcatggactagcatcagccagctgtgcctgatcggc
tgcagcccccatcggcgagcactcgggcagcaaggcagcactgcaccaacgtggcgtg
aacccggcgactgcgccccccgactgatcaaccgtgcagccaggcccctgcaccgacatg
gtggacaccggcttcggccatggactctgctgagctgcagccaacaagacggcgaggtg
ccctggacatctgcacagcctgccaccatcaagatggtgagcgag
cctacggcgacagccggcgcgtgcctgttctttctactgagagagaccgtgcctgtacatcaaggcagc
ttcaacagccgccaccgccagatcttcaacaagcctgttcgtgccaccactcccacctggtgacctg
ggcagccggccaccgccagtctgctgccgtcagagacgtgctgatccgaacgtcagc
accgcatctgctgtgtgctgaccgagacggagttccagtctgcaccgagaccttc
aacatgagctgagactaccggagagagctgagccctcacagaacagcaccaacttc
aaggagtaccgccgacgtgactgaccatccaggagcatcgaacagcagccaggcacc
atcacctgaccgcgcctgcagccctgccccgcgcaccccccaggagacacctggag
gactggaacttcggcctgccatcgcctggaggtgaactttcagcgccagagccgaccc
gtgaagaagtacacctttctggagaaagtgtcctgcagggtgaagccgacctggac
ctgaaagaagtacacccttctggagaaagtggcctgcaggttcagcgccgaagccaagttc
cagttcccctgggcagaaaaggccaccccccaccaggcgccagcaccgccaagttc
acctgggcaagaggaaagccaccccccaccaggacaccagcagccgccaagccaagaga
aagaaagaaagctga

FIG. 9

(SEQ ID NO:3)

pET24a(+):69415 – L1X_optEc3 (*E. coli* optimized)

..............................

```
   1 ATCCGGATAT AGTTCCTCCT TTCAGCAAAA AACCCCTCAA GACCCGTTTA GAGGCCCCAA GGGGTTATGC
  71 TAGTTATTGC TCAGCGGTGG CAGCAGCCAA CTCAGCTTCC TTTCGGGCTT TGTTAGCAGC CGGATCTCAG
 141 TGGTGGTGGT GGTGGTGCTC GAGTCATTAC AGTTTACGCT TCTTACGCTT CGCGGTGGTG CTAGTGCTGC
 211 TGGTGGTCGG CGTGGCCTTG CGCTTGCCCA GGGTAAACTT CGGTTTTGCC TTCAGACCCG CTTGCAGCAG
 281 GAATTTGCGG CCCAGCGGAA ACTGGTCCAA ATCAGCCGAG AATTTCTCTT TCAGATTGAC CTCCCAAAAG
 351 GTGTATTTCT TCAGCGGATC TTCTTTCGGT GCCGGTGGGG TATGCTTCTG ACACGCGATT GCCTGGGAGG
 421 TAACAAACG GTACGTATCC TCCAGCGTGC CGCCAGGCGG AGGTTGCAGA CCGAAGTTCC AATCCTCCAG
 491 AATCGTGCTG TTCATGCTAT GAATGTAGCT CATCACGTCC GCCGTCAGGG TGATTTACA CAGCTGAAAA
 561 ATGAATTGCA GATCATATTC TTCGCCGTGA CGCAGATATT CTTTAAAGTT GGTATTCTTA TAGGTCGGCT
 631 CGCTGGTCGA GATCGCTGCA CACAGGCTCA TATTCGTGCT GCGCGTAGTG TCAACCACGG TAACAAACAG
 701 TTGATTACCC CAGCAAATAC CATTATTGTG ACCCGTGCCA CGTTGCAGCC AGTAAGGCTT ATTGAAAATC
 771 TGAGCATCGC TAGTAACCAT GCTGCCGCTT GGCGTCGGAA AGTAATTGCT GTTCGCCAAC GTCGCGGTGC
 841 TACCGCTACC TTTGATGTAC AGGTCAGTCG GCACGTTCTC ACCCACGGCA CCTGCGCGAT TGAACAGGTG
 911 ACGGACGAAC ATTTGCTCGC GACGCAGGTA AAGAACAGG CTGTCACCAT ACGGTTCGCT GACCATTTTG
 981 ATATAGTCCG GGTACTTGCA GATAGAGGTG CAAATGTCCA ACGGAACCTC GCTCTTGTTG GCCTGCAAGG
1051 TGGTAAAGTC CATCGCACCA AGCCCGTAT CCACCATATC ACCATCTTGA ATCACCGTAT TGATCAGTTC
1121 CAGCGGTGGG CAATCACCCG GATTCACCGC CACGTTATTG CACGGGCTAC CTTTACCCCA GTGCTCACCG
1191 ATCGGCGGTT TACAACCGAT CAGGCACAGC TGGGTTTGCT TATAGTCCAT CGAAATGCAT TCACGATTAT
1261 CCACGCCTGC GTTCGCGGCG TAGGCAGAAG CGTTCTCGGT ATCGTCCAGT TTGTTCAGCA GCGGATGGCC
1331 GGAGATGCCG ACGCCCAGGG GCTGACCACG ACCAACCTCA ACGCCGACAC ACGCCCAAAC CAGACGCTGC
1401 GTGTCCGGGT TATAGAAGCT GGTGTCCGGG AAACCGAATT TGTTCGGGTC ACGCAGATGA ATGCGGAACA
1471 CACGATATTG CAAGCCGCTG ACCTTCGGTA CCAGAATTTT GTTGTTGTTC GGTTCTTAA TCGGGAAATA
1541 CGGGTGACCC ACGGCCAACA GGCGGGACGT ACCCGCGTGG TAGTAGATAT TGGTGCGCGC GACGTATTCG
1611 TCGGTAGAGA CAACCTTGCT AACTGGGACA GGCGGTAAGT ACACGGTCGC TTCGCTCGGG AGCCACAGGG
1681 ACATTTTTTT TATCTCCTTT AAAGTTAAAC AAAATTATTT CTAGAGGGGA ATTGTATCC GCTCACAATT
1751 CCCCTATAGT GAGTCGTATT AATTTCGCGG GATCGAGATC TCGATCCTCT ACGCCGGACG CATCGTGGCC
1821 GGCATCACCG GCGCCACAGG TGCGGTTGCT GGCGCCTATA TCGCCGACAT CACCGATGGG GAAGATCGGG
1891 CTCGCCACTT CGGGCTCATG AGCGCTTGTT TCGGCGTGGG TATGGTGGCA GGCCCCGTGG CCGGGGGACT
1961 GTTGGGCGCC ATCTCCTGC ATGCACCATT CCTTGCGGCG GCGGTGCTCA ACGGCCTCAA CCTACTACTG
2031 GGCTGCTTCC TAATGCAGGA GTCGCATAAG GGAGAGCGTC GAGATCCCGG ACACCATCGA ATGGCGCAAA
2101 ACCTTTCGCG GTATGGCATG ATAGCGCCCG GAAGAGAGTC AATTCAGGGT GGTGAATGTG AAACCAGTAA
2171 CGTTATACGA TGTCGCAGAG TATGCCGGTG TCTCTTATCA GACCGTTTCC CGCGTGGTGA ACCAGGCCAG
2241 CCACGTTTCT GCGAAAACGC GGGAAAAAGT GGAAGCGGCG ATGGCGGAGC TGAATTACAT TCCCAACCGC
2311 GTGGCACAAC AACTGGCGGG CAAACAGTCG TTGCTGATTG GCGTTGCCAC CTCCAGTCTG GCCCTGCACG
2381 CGCCGTCGCA AATTGTCGCG GCGATTAAAT CTCGCGCCGA TCAACTGGGT GCCAGCGTGG TGGTGTCGAT
2451 GGTAGAACGA AGCGGCGTCG AAGCCTGTAA AGCGGCGGTG CACAATCTTC TCGCGCAACG CGTCAGTGGG
2521 CTGATCATTA ACTATCCGCT GGATGACCAG GATGCCATTG CTGTGGAAGC TGCCTGCACT AATGTTCCGG
2591 CGTTATTTCT TGATGTCTCT GACCAGACAC CCATCAACAG TATTATTTTC TCCCATGAAG ACGGTACGCG
2661 ACTGGGCGTG GAGCATCTGG TCGCATTGGG TCACCAGCAA ATCGCGCTGT AGCGGGCCC ATTAAGTTCT
2731 GTCTCGGCGC GTCTGCGTCT GGCTGGCTGG CATAAATATC TCACTCGCAA TCAAATTCAG CCGATAGCGG
2801 AACGGGAAGG CGACTGGAGT GCCATGTCCG GTTTTCAACA AACCATGCAA ATGCTGAATG AGGGCATCGT
2871 TCCCACTGCG ATGCTGGTTG CCAACGATGA GATGGCGTCG GGCGCAATGC GCGCCATTAC CGAGTCCGGG
2941 CTGCGCGTTG GTGCGGATAT CTCGGTAGTG GGATACGACG ATACCGAAGA CAGCTCATGT TATATCCCGC
3011 CGTTAACCAC CATCAAACAG GATTTTCGCC TGCTGGGGCA AACCAGCGTG GACCGCTTGC TGCAACTCTC
3081 TCAGGGCCAG GCGGTGAAGG GCAATCAGCT GTTGCCCGTC TCACTGGTGA AAGAAAAAC CACCCTGGCG
3151 CCCAATACGC AAACCGCCTC TCCCCGCGCG TTGGCCGATT CATTAATGCA GCTGGCACGA CAGGTTTCCC
3221 GACTGGAAAG CGGGCAGTGA GCGCAACGCA ATTAATGTAA GTTAGCTCAC TCATTAGGCA CCGGGATCTC
3291 GACCGATGCC CTTGAGAGCC TTCAACCCAG TCAGCTCCTT CCGGTGGGCG CGGGGCATGA CTATCGTCGC
3361 CGCACTTATG ACTGTCTTCT TTATCATGCA ACTCGTAGGA CAGGTGCCGG CAGCGCTCTG GGTCATTTTC
3431 GGCGAGGACC GCTTTCGCTG GAGCGCGACG ATGATCGGCC TGTCGCTTGC GGTATTCGGA ATCTTGCACG
3501 CCCTCGCTCA AGCCTTCGTC ACTGGTCCCG CCACCAAACG TTTCGGCGAG AAGCAGGCCA TTATCGCCGG
3571 CATGGCGGCC CCACGGGTGC GCATGATCGT GCTCCTGTCG TTGAGGACCC GGCTAGGCTG GCGGGGTTGC
3641 CTTACTGGTT AGCAGAATGA ATCACCGATA CGCGAGCGAA CGTGAAGCGA CTGCTGCTGC AAAACGTCTG
3711 CGACCTGAGC AACAACATGA ATGGTCTTCG GTTTCCGTGT TTCGTAAAGT CTGGAAACGC GGAAGTCAGC
3781 GCCCTGCACC ATTATGTTCC GGATCTGCAT CGCAGGATGC TGCTGGCTAC CCTGTGGAAC ACCTACATCT
3851 GTATTAACGA AGCGCTGGCA TTGACCCTGA GTGATTTTTC TCTGGTCCCG CCGCATCCAT ACCGCCAGTT
3921 GTTTACCCTC ACACGTTCCA AGTAACCGGC CATGTTCATC ATCAGTAACC CGTATCGTGA GCATCCTCTC
3991 TCGTTTCATC GGTATCATTA CCCCCATGAA CAGAAATCCC CCTTACACGG AGGCATCAGT GACCAAACAG
4061 GAAAAAACCG CCCTTAACAT GGCCCGCTTT ATCAGAAGCC AGACATTAAC GCTTCTGGAG AAACTCAACG
```

FIG. 9 (continued)

```
4131 AGCTGGACGC GGATGAACAG GCAGACATCT GTGAATCGCT TCACGACCAC GCTGATGAGC TTTACCGCAG
4201 CTGCCTCGCG CGTTTCGGTG ATGACGGTGA AAACCTCTGA CACATGCAGC TCCCGGAGAC GGTCACAGCT
4271 TGTCTGTAAG CGGATGCCGG GAGCAGACAA GCCCGTCAGG GCGCGTCAGC GGGTGTTGGC GGGTGTCGGG
4341 GCGCAGCCAT GACCCAGTCA CGTAGCGATA GCGGAGTGTA TACTGGCTTA ACTATGCGGC ATCAGAGCAG
4411 ATTGTACTGA GAGTGCACCA TATATGCGGT GTGAAATACC GCACAGATGC GTAAGGAGAA AATACCGCAT
4481 CAGGCGCTCT TCCGCTTCCT CGCTCACTGA CTCGCTGCGC TCGGTCGTTC GGCTGCGGCG AGCGGTATCA
4551 GCTCACTCAA AGGCGGTAAT ACGGTTATCC ACAGAATCAG GGGATAACGC AGGAAAGAAC ATGTGAGCAA
4621 AAGGCCAGCA AAAGGCCAGG AACCGTAAAA AGGCCGCGTT GCTGGCGTTT TTCCATAGGC TCCGCCCCC
4691 TGACGAGCAT CACAAAAATC GACGCTCAAG TCAGAGGTGG CGAAACCCGA CAGGACTATA AAGATACCAG
4761 GCGTTTCCCC CTGGAAGCTC CCTCGTGCGC TCTCCTGTTC CGACCCTGCC GCTTACCGGA TACCTGTCCG
4831 CCTTTCTCCC TTCGGAAGC GTGGCGCTTT CTCATAGCTC ACGCTGTAGG TATCTCAGTT CGGTGTAGGT
4901 CGTTCGCTCC AAGCTGGGCT GTGTGCACGA ACCCCCCGTT CAGCCCGACC GCTGCGCCTT ATCCGGTAAC
4971 TATCGTCTTG AGTCCAACCC GGTAAGACAC GACTTATCGC CACTGGCAGC AGCCACTGGT AACAGGATTA
5041 GCAGAGCGAG GTATGTAGGC GGTGCTACAG AGTTCTTGAA GTGGTGGCCT AACTACGGCT ACACTAGAAG
5111 GACAGTATTT GGTATCTGCG CTCTGCTGAA GCCAGTTACC TTCGGAAAAA GAGTTGGTAG CTCTTGATCC
5181 GGCAAACAAA CCACCGCTGG TAGCGGTGGT TTTTTTGTTT GCAAGCAGCA GATTACGCGC AGAAAAAAAG
5251 GATCTCAAGA AGATCCTTTG ATCTTTTCTA CGGGGTCTGA CGCTCAGTGG AACGAAAACT CACGTTAAGG
5321 GATTTTGGTC ATGAACAATA AAACTGTCTG CTTACATAAA CAGTAATACA AGGGGTGTTA TGAGCCATAT
5391 TCAACGGGAA ACGTCTTGCT CTAGGCGCG ATTAAATTCC AACATGGATG CTGATTTATA TGGGTATAAA
5461 TGGGCTCGCG ATAATGTCGG GCAATCAGGT GCGACAATCT ATCGATTGTA TGGGAAGCCC GATGCGCCAG
5531 AGTTGTTTCT GAAACATGGC AAAGGTAGCG TTGCCAATGA TGTTACAGAT GAGATGGTCA GACTAAACTG
5601 GCTGACGGAA TTTATGCCTC TTCCGACCAT CAAGCATTTT ATCCGTACTC CTGATGATGC ATGGTTACTC
5671 ACCACTGCGA TCCCCGGGAA AACAGCATTC CAGGTATTAG AAGAATATCC TGATTCAGGT GAAAATATTG
5741 TTGATGCGCT GGCAGTGTTC CTGCGCCGGT TGCATTCGAT TCCTGTTTGT AATTGTCCTT TTAACAGCGA
5811 TCGCGTATTT CGTCTCGCTC AGGCGCAATC ACGAATGAAT AACGGTTTGG TTGATGCGAG TGATTTTGAT
5881 GACGAGCGTA ATGGCTGGCC TGTTGAACAA GTCTGGAAAG AAATGCATAA ACTTTTGCCA TTCTCACCGG
5951 ATTCAGTCGT CACTCATGGT GATTTCTCAC TTGATAACCT TATTTTTGAC GAGGGGAAAT TAATAGGTTG
6021 TATTGATGTT GGACGAGTCG GAATCGCAGA CCGATACCAG GATCTTGCCA TCCTATGGAA CTGCCTCGGT
6091 GAGTTTTCTC CTTCATTACA GAAACGGCTT TTTCAAAAAT ATGGTATTGA TAATCCTGAT ATGAATAAAT
6161 TGCAGTTTCA TTTGATGCTC GATGAGTTTT TCTAAGAATT AATTCATGAG CGGATACATA TTTGAATGTA
6231 TTTAGAAAAA TAAACAAATA GGGGTTCCGC GCACATTTCC CCGAAAAGTG CCACCTGAAA TTGTAAACGT
6301 TAATATTTTG TTAAAATTCG CGTTAAATTT TTGTTAAATC AGCTCATTTT TTAACCAATA GGCCGAAATC
6371 GGCAAAATCC CTTATAAATC AAAAGAATAG ACCGAGATAG GGTTGAGTGT TGTTCCAGTT TGGAACAAGA
6441 GTCCACTATT AAAGAACGTG GACTCCAACG TCAAAGGGCG AAAACCGTC TATCAGGGCG ATGGCCCACT
6511 ACGTGAACCA TCACCCTAAT CAAGTTTTTT GGGGTCGAGG TGCCGTAAAG CACTAAATCG GAACCCTAAA
6581 GGGAGCCCCC GATTTAGAGC TTGACGGGGA AAGCCGGCGA ACGTGGCGAG AAAGGAAGGG AAGAAAGCGA
6651 AAGGAGCGGG CGCTAGGGCG CTGGCAAGTG TAGCGGTCAC GCTGCGCGTA ACCACCACAC CCGCCGCGCT
6721 TAATGCGCCG CTACAGGGCG CGTCCCATTC GCCA
```

FIG. 10

(SEQ ID NO:4)

pBAD-HisA:69414 – wtL2_optEc1 (*E. coli* optimized)

```
   1 AAGAAACCAA TTGTCCATAT TGCATCAGAC ATTGCCGTCA CTGCGTCTTT TACTGGCTCT TCTCGCTAAC
  71 CAAACCGGTA ACCCCGCTTA TTAAAAGCAT TCTGTAACAA AGCGGGACCA AAGCCATGAC AAAAACGCGT
 141 AACAAAAGTG TCTATAATCA CGGCAGAAAA GTCCACATTG ATTATTTGCA CGGCGTCACA CTTTGCTATG
 211 CCATAGCATT TTTATCCATA AGATTAGCGG ATCCTACCTG ACGCTTTTTA TCGCAACTCT CTACTGTTTC
 281 TCCATACCCG TTTTTTGGGC TAACAGGAGG AATTAACCAT GAGACACAAA AGATCAGCCA AACGTACGAA
 351 GAGAGCAAGC GCGAGCCAAC TGTATAAGAC CTGCAAACGA GCGGGTACTT GTCCGCCTGA CATCATCCCT
 421 AAGGTTGAGG GTAAGACCAT CGCGGATCAA ATTCTGCAAT ACGGCAGCAT GGGCGTTTTC TTTGGTGGCC
 491 TGGGTATTGG TACGGGTAGC GGCACCGGCG GTCGTACCGG CTACATCCCG CTGGGCACCC GCCCACCGAC
 561 CGCCACCGAT ACGCTGGCCC CAGTGCGTCC GCCGCTGACC GTCGATCCGG TTGGCCCGTC CGACCCGAGC
 631 ATTGTTAGCC TGGTGGAAGA AACCAGCTTC ATTGATGCGG GTGCTCCTAC GAGCGTTCCG TCTATCCCGC
 701 CAGACGTGAG CGGTTTTAGC ATTACGACGA GCACCGATAC CACCCCGGCT ATTTTGGACA TTAACAACAC
 771 GGTGACTACC GTGACCACCC ACAACAATCC TACCTTTACT GACCCAAGCG TGTTGCAACC GCCGACCCCG
 841 GCAGAAACGG GTGGCCACTT CACCCTGAGC AGCTCCACCA TCAGCACGCA CAATTATGAA GAGATTCCGA
 911 TGGACACCTT TATCGTATCT ACGAATCCGA ATACGGTCAC GAGCAGCACC CCGATCCCGG GCTCCCGTCC
 981 GGTCGCGCGT CTGGGTCTGT ACTCCCGTAC CACCCAGCAG GTTAAAGTCG TTGACCGGGC GTTTGTTACG
1051 ACCCCGACGA AGCTGATTAC CTATGACAAT CCGGCCTACG AGGGCATTGA CGTTGATAAC ACCCTGTACT
1121 TCAGCAGCAA CGATAATAGC ATCAATATTG CACCGGACCC TGATTTTCTG GACATCGTCG CACTGCACCG
1191 TCCGGCGCTG ACGAGCCGTC GCACGGGTAT TCGTTATTCC CGCATCGGCA CAAACAAAC CCTGCGCACC
1261 CGTTCGGGTA AGTCTATCGG CGCAAAAGTC CATTACTATT ACGACCTGTC TACCATCGAT CCGGCGGAAG
1331 AGATTGAGTT GCAGACGATT ACTCCGAGCA CCTACACCAC TACGTCCCAT GCAGCGAGCC CGACCAGCAT
1401 CAACAATGGT CTGTACGACA TCTATGCGGA TGACTTTATC ACTGATACGA GCACCACGCC GGTCCCGAGC
1471 GTGCCGAGCA CCAGCCGTCC GGGCTATATC CCGGCCAACA CCACGATTCC GTTCGGTGGT GCGTATAACA
1541 TCCCGTTGGT GAGCGGTCCA GACATCCCGA TCAACATTAC GGATCAGGCA CCGAGCCTGA TTCCGATCGT
1611 CCCGGGTAGC CCACAGTACA CCATCATTGC TGATGCAGGT GACTTCTACC TGCATCCGTC TTACTATATG
1681 TTGCGTAAAC GCCGCAAGCG TCTGCCGTAC TTCTTCTCGG ATGTGAGCCT GGCGGCGTAA TGAATTCGAA
1751 GCTTGGCTGT TTTGGCGGAT GAGAGAAGAT TTTCAGCCTG ATACAGATTA AATCAGAACG CAGAAGCGGT
1821 CTGATAAAAC AGAATTTGCC TGGCGGCAGT AGCGCGGTGG TCCCACCTGA CCCCATGCCG AACTCAGAAG
1891 TGAAACGCCG TAGCGCCGAT GGTAGTGTGG GGTCTCCCCA TGCGAGAGTA GGGAACTGCC AGGCATCAAA
1961 TAAAACGAAA GGCTCAGTCG AAAGACTGGG CCTTTCGTTT TATCTGTTGT TTGTCGGTGA ACGCTCTCCT
2031 GAGTAGGACA AATCCGCCGG GAGCGGATTT GAACGTTGCG AAGCAACGGC CCGGAGGGTG GCGGGCAGGA
2101 CGCCCGCCAT AAACTGCCAG GCATCAAATT AAGCAGAAGG CCATCCTGAC GGATGGCCTT TTTGCGTTTC
2171 TACAAACTCT TTTGTTTATT TTTCTAAATA CATTCAAATA TGTATCCGCT CATGAGACAA TAACCCTGAT
2241 AAATGCTTCA ATAATATTGA AAAAGGAAGA GTATGAGTAT TCAACATTTC CGTGTCGCCC TTATTCCCTT
2311 TTTTGCGGCA TTTTGCCTTC CTGTTTTTGC TCACCCAGAA ACGCTGGTGA AGTAAAAGA TGCTGAAGAT
2381 CAGTTGGGTG CACGAGTGGG TTACATCGAA CTGGATCTCA ACAGCGGTAA GATCCTTGAG AGTTTTCGCC
2451 CCGAAGAACG TTTTCCAATG ATGAGCACTT TTAAAGTTCT GCTATGTGGC GCGGTATTAT CCCGTGTTGA
2521 CGCCGGGCAA GAGCAACTCG GTCGCCGCAT ACACTATTCT CAGAATGACT TGGTTGAGTA CTCACCAGTC
2591 ACAGAAAAGC ATCTTACGGA TGGCATGACA GTAAGAGAAT TATGCAGTGC TGCCATAACC ATGAGTGATA
2661 ACACTGCGGC CAACTTACTT CTGACAACGA TCGGAGGACC GAAGGAGCTA ACCGCTTTTT TGCACAACAT
2731 GGGGGATCAT GTAACTCGCC TTGATCGTTG GGAACCGGAG CTGAATGAAG CCATACCAAA CGACGAGCGT
2801 GACACCACGA TGCCTGTAGC AATGGCAACA ACGTTGCGCA AACTATTAAC TGGCGAACTA CTTACTCTAG
2871 CTTCCCGGCA ACAATTAATA GACTGGATGG AGGCGGATAA AGTTGCAGGA CCACTTCTGC GCTCGGCCCT
2941 TCCGGCTGGC TGGTTTATTG CTGATAAATC TGGAGCCGGT GAGCGTGGGT CTCGCGGTAT CATTGCAGCA
3011 CTGGGGCCAG ATGGTAAGCC CTCCCGTATC GTAGTTATCT ACACGACGGG GAGTCAGGCA ACTATGGATG
3081 AACGAAATAG ACAGATCGCT GAGATAGGTG CCTCACTGAT TAAGCATTGG TAACTGTCAG ACCAAGTTTA
3151 CTCATATATA CTTTAGATTG ATTTAAAACT TCATTTTTAA TTTAAAAGGA TCTAGGTGAA GATCCTTTTT
3221 GATAATCTCA TGACCAAAAT CCCTTAACGT GAGTTTTCGT TCCACTGAGC GTCAGACCCC GTAGAAAAGA
3291 TCAAAGGATC TTCTTGAGAT CCTTTTTTTC TGCGCGTAAT CTGCTGCTTG CAAACAAAAA AACCACCGCT
3361 ACCAGCGGTG GTTTGTTTGC CGGATCAAGA GCTACCAACT CTTTTTCCGA AGGTAACTGG CTTCAGCAGA
3431 GCGCAGATAC CAAATACTGT CCTTCTAGTG TAGCCGTAGT TAGGCCACCA CTTCAAGAAC TCTGTAGCAC
3501 CGCCTACATA CCTCGCTCTG CTAATCCTGT TACCAGTGGC TGCTGCCAGT GGCGATAAGT CGTGTCTTAC
3571 CGGGTTGGAC TCAAGACGAT AGTTACCGGA TAAGGCGCAG CGGTCGGGCT GAACGGGGGG TTCGTGCACA
3641 CAGCCCAGCT TGGAGCGAAC GACCTACACC GAACTGAGAT ACCTACAGCG TGAGCTATGA GAAAGCGCCA
3711 CGCTTCCCGA AGGGAGAAAG GCGGACAGGT ATCCGGTAAG CGGCAGGGTC GGAACAGGAG AGCGCACGAG
3781 GGAGCTTCCA GGGGGAAACG CCTGGTATCT TTATAGTCCT GTCGGGTTTC GCCACCTCTG ACTTGAGCGT
3851 CGATTTTTGT GATGCTCGTC AGGGGGGCGG AGCCTATGGA AAAACGCCAG CAACGCGGCC TTTTTACGGT
3921 TCCTGGCCTT TTGCTGGCCT TTTGCTCACA TGTTCTTTCC TGCGTTATCC CCTGATTCTG TGGATAACCG
3991 TATTACCGCC TTTGAGTGAG CTGATACCGC TCGCCGCAGC CGAACGACCG AGCGCAGCGA GTCAGTGAGC
4061 GAGGAAGCGG AAGAGCGCCT GATGCGGTAT TTTCTCCTTA CGCATCTGTG CGGTATTTCA CACCGCATAT
4131 GGTGCACTCT CAGTACAATC TGCTCTGATG CCGCATAGTT AAGCCAGTAT ACACTCCGCT ATCGCTACGT
```

FIG. 10 (continued)

```
4201 GACTGGGTCA TGGCTGCGCC CCGACACCCG CCAACACCCG CTGACGCGCC CTGACGGGCT TGTCTGCTCC
4271 CGGCATCCGC TTACAGACAA GCTGTGACCG TCTCCGGGAG CTGCATGTGT CAGAGGTTTT CACCGTCATC
4341 ACCGAAACGC GCGAGGCAGC AGATCAATTC GCGCGCGAAG GCGAAGCGGC ATGCATAATG TGCCTGTCAA
4411 ATGGACGAAG CAGGGATTCT GCAAACCCTA TGCTACTCCG TCAAGCCGTC AATTGTCTGA TTCGTTACCA
4481 ATTATGACAA CTTGACGGCT ACATCATTCA CTTTTCTTC ACAACGGCA CGGAACTCGC TCGGGCTGGC
4551 CCCGGTGCAT TTTTTAAATA CCCGCGAGAA ATAGAGTTGA TCGTCAAAAC CAACATTGCG ACCGACGGTG
4621 GCGATAGGCA TCCGGGTGGT GCTCAAAAGC AGCTTCGCCT GGCTGATACG TTGGTCCTCG CGCCAGCTTA
4691 AGACGCTAAT CCCTAACTGC TGGCGGAAAA GATGTGACAG ACGCGACGGC GACAAGCAAA CATGCTGTGC
4761 GACGCTGGCG ATATCAAAAT TGCTGTCTGC CAGGTGATCG CTGATGTACT GACAAGCCTC GCGTACCCGA
4831 TTATCCATCG GTGGATGGAG CGACTCGTTA ATCGCTTCCA TGCGCCGCAG TAACAATTGC TCAAGCAGAT
4901 TTATCGCCAG CAGCTCCGAA TAGCGCCCTT CCCCTTGCCC GGCGTTAATG ATTTGCCCAA ACAGGTCGCT
4971 GAAATGCGGC TGGTGCGCTT CATCCGGGCG AAAGAACCCC GTATTGGCAA ATATTGACGG CCAGTTAAGC
5041 CATTCATGCC AGTAGGCGCG CGGACGAAAG TAAACCCACT GGTGATACCA TTCGCGAGCC TCCGGATGAC
5111 GACCGTAGTG ATGAATCTCT CCTGGCGGGA ACAGCAAAAT ATCACCCGGT CGGCAAACAA ATTCTCGTCC
5181 CTGATTTTTC ACCACCCCCT GACCGCGAAT GGTGAGATTG AGAATATAAC CTTTCATTCC CAGCGGTCGG
5251 TCGATAAAAA AATCGAGATA ACCGTTGGCC TCAATCGGCG TTAAACCCGC CACCAGATGG GCATTAAACG
5321 AGTATCCCGG CAGCAGGGGA TCATTTTGCG CTTCAGCCAT ACTTTTCATA CTCCCGCCAT TCAGAG
```

SEQUENCE LISTING

```
<160> NUMBER OF SEQ ID NOS: 4

<210> SEQ ID NO 1
<211> LENGTH: 10827
<212> TYPE: DNA
<213> ORGANISM: Artificial Sequence
<220> FEATURE:
<223> OTHER INFORMATION: Synthetic Oligonucleotide

<400> SEQUENCE: 1
ctagagccac catgagcctg tggctgccca gcgaggccac cgtgtacctg cccccgtgc      60 ccgtgagcaa ggtggtgagc accgacgagt acgtggccag gaccaacatc tactaccacg    120
ccggcaccag caggctgctg gccgtgggcc acccctactt ccccatcaag aagcccaaca    180
```

```
acaacaagat cctggtgccc aaggtgagcg gcctgcagta cagggtgttc aggatccacc      240
tgcccgaccc caacaagttc ggcttccccg acaccagctt ctacaacccc gacacccaga      300
ggctggtgtg ggcctgcgtg ggcgtggagg tgggcagggg ccagcccctg ggcgtgggca      360
tcagcggcca ccccctgctg aacaagctgg acgacaccga gaacgccagc gcctacgccg      420
ccaacgccgg cgtggacaac agggagtgca tcagcatgga ctacaagcag acccagctgt      480
gcctgatcgg ctgcaagccc ccatcggcg agcactgggg caaggcagc ccctgcacca       540 acgtggccgt gaaccccggc gactgccccc cctggagct gatcaacacc gtgatccagg       600
acggcgacat ggtggacacc ggcttcggcg ccatggactt caccaccctg caggccaaca      660
agagcgaggt gcccctggac atctgcacca gcatctgcaa gtaccccgac tacatcaaga      720
tggtgagcga gccctacggc gacagcctgt cttctacct gaggagggag cagatgttcg       780
tgaggcacct gttcaacagg gccggcgccg tgggcgagaa cgtgcccacc gacctgtaca      840
tcaagggcag cggcagcacc gccacccctgg ccaacagcaa ctacttcccc accccccagcg    900 gcagcatggt gaccagcgac gcccagatct tcaacaagcc ctactggctg cagagggccc      960
agggccacaa caacggcatc tgctggggca ccagctgtt cgtgaccgtg gtggacacca      1020
ccaggagcac caacatgagc ctgtgcgccg ccatcagcac cagcgagacc acctacaaga     1080
acaccaactt caaggagtac ctgaggcacg gcgaggagta cgacctgcag ttcatcttcc     1140
agctgtgcaa gatcaccctg accgccgacg tgatgaccta catccacagc atgaacagca     1200
ccatcctgga ggactggaac ttcggcctgc agccccccc cggcggcacc ctggaggaca     1260
cctacaggtt cgtgaccagc caggccatcg cctgccagaa gcacaccccc cccgccccca     1320
aggaggaccc cctgaagaag tacaccttct gggaggtgaa cctgaaggag aagttcagcg     1380
ccgacctgga ccagttcccc ctgggcagga agttcctgct gcaggccggc ctgaaggcca     1440
agcccaagtt caccctgggc aagaggaagg ccacccccac caccagcagc accagcacca     1500
ccgccaagag gaagaagagg aagctgtgaa agcttatcga taccgtcgac ctcgacctgc     1560
agaagcttaa aacagctctg ggttgtacc caccccagag gcccacgtgg cggctagtac     1620
tccggtattg cggtacccct gtacgcctgt tttatactcc cttcccgtaa cttagacgca     1680
caaaaccaag ttcaatagaa ggggggtacaa accagtacca ccacgaacaa gcacttctgt     1740 ttcccccggtg atgtcgtata gactgcttgc gtggttgaaa gcgacggatc cgttatccgc     1800
ttatgtactt cgagaagccc agtaccacct cggaatcttc gatgcgttgc gctcagcact     1860
caaccccaga gtgtagctta ggctgatgag tctggacatc cctcaccggt gacggtggtc     1920
caggctgcgt tggcggccta cctatggcta acgccatggg acgctagttg tgaacaaggt     1980
gtgaagagcc tattgagcta cataagaatc ctccggcccc tgaatgcggc taatcccaac     2040
ctcggagcag gtggtcacaa accagtgatt ggcctgtcgt aacgcgcaag tccgtggcgg     2100
aaccgactac tttgggtgtc cgtgtttcct tttattttat tgtggctgct tatggtgaca     2160
atcacagatt gttatcataa agcgaattgg attgcggccg ctctagagcc accatgaggc     2220
acaagaggag cgccaagagg accaagaggg ccagcgccac ccagctgtac aagacctgca     2280
agcaggccgg cacctgcccc cccgacatca tccccaaggt ggagggcaag accatcgccg     2340
accagatcct gcagtacggc agcatgggcg tgttcttcgg cggcctgggc atcggcaccg     2400
gcagcggcac cggcggcagg accggctaca tccccctggg caccaggccc ccaccgcca     2460 ccgacaccct ggccccgtg aggccccccc tgaccgtgga cccgtgggc cccagcgacc     2520
```

```
ccagcatcgt gagcctggtg gaggagacca gcttcatcga cgccggcgcc cccaccagcg    2580
tgcccagcat ccccccgac gtgagcggct cagcatcac caccagcacc gacaccaccc      2640
ccgccatcct ggacatcaac aacaccgtga ccaccgtgac cacccacaac aaccccacct    2700
tcaccgaccc cagcgtgctg cagcccccca ccccgccga gaccggcggc cacttcacccc   2760 tgagcagcag caccatcagc acccacaact acgaggagat ccccatggac accttcatcg    2820
tgagcaccaa ccccaacacc gtgaccagca gcacccccat ccccggcagc aggcccgtgg    2880
ccaggctggg cctgtacagc aggaccaccc agcaggtgaa ggtggtggac cccgccttcg    2940
tgaccacccc caccaagctg atcacctacg acaaccccgc ctacgagggc atcgacgtgg    3000
acaacacccc tgtacttcagc agcaacgaca acagcatcaa catcgccccc gaccccgact   3060
tcctggacat cgtggccctg cacaggcccg ccctgaccag caggaggacc ggcatcaggt    3120
acagcaggat cggcaacaag cagaccctga ggaccaggag cggcaagagc atcggcgcca    3180
aggtgcacta ctactacgac ctgagcacca tcgaccccgc cgaggagatc gagctgcaga    3240
ccatcacccc cagcacctac accaccacca gccacgccgc cagccccacc agcatcaaca    3300
acggcctgta cgacatctac gccgacgact tcatcaccga caccagcacc accccgtgc    3360 ccagcgtgcc cagcaccagc ctgagcggct acatccccgc caacaccacc atccccttcg    3420
gtggcgccta caacatcccc ctggtgagcg gccccgacat ccccatcaac atcaccgacc    3480
aggcccccag cctgatcccc atcgtgcccg gcagccccca gtacaccatc atcgccgacg    3540
ccggcgactt ctacctgcac cccagctact acatgctgag gaagaggagg aagaggctgc    3600
cctacttctt cagcgacgtg agcctggccg cctgaaagct tttgaattc tttggatcca    3660 ctagtggatc cccgggctg caggaattcg atatcaagct tatcgataat caacctctgg    3720
attacaaaat ttgtgaaaga ttgactggta ttcttaacta tgttgctcct tttacgctat    3780
gtggatacgc tgctttaatg cctttgtatc atgctattgc ttcccgtatg gctttcattt    3840
tctcctcctt gtataaatcc tggttgctgt ctctttatga ggagttgtgg cccgttgtca    3900
ggcaacgtgg cgtggtgtgc actgtgtttg ctgacgcaac ccccactggt tggggcattg    3960
ccaccacctg tcagctcctt tccgggactt tcgctttccc cctccctatt gccacggcgg    4020
aactcatcgc cgcctgcctt gcccgctgct ggacaggggc tcggctgttg ggcactgaca    4080
attccgtggt gttgtcgggg aaatcatcgt ccttcttg ctgctcgcc tgtgttgcca      4140 cctggattct gcgcgggacg tccttctgct acgtcccttc ggccctcaat ccagcggacc    4200
ttccttcccg cggcctgctg ccggctctgc ggcctcttcc gcgtcttcgc cttcgccctc    4260
agacgagtcg atctcccctt tgggccgcct ccccgcatcg ataccgtcgg cccgtttaaa    4320
cccgctgatc agcctcgact gtgccttcta gttgccagcc atctgttgtt tgcccctccc    4380
ccgtgccttc cttgaccctg gaaggtgcca ctcccactgt cctttcctaa taaaatgagg    4440
aaattgcatc gcattgtctg agtaggtgtc attctattct ggggggtggg gtggggcagg    4500
acagcaaggg ggaggattgg gaagacaata gcaggcatgc tggggatgcg gtgggctcta    4560
tggcttctga ggcggaaaga accagctggg gctctagggg gtatccccac gcgccctgta    4620
gcggcgcatt aagcgcggcg ggtgtggtgg ttacgcgcag cgtgaccgct acacttgcca    4680
gcgccctagc gcccgctcct ttcgctttct tcccttcctt tctcgccacg ttcgccggct    4740
ttccccgtca agctctaaat cggggggctcc ctttagggtt ccgatttagt gctttacggc    4800
acctcgaccc caaaaaactt gattagggtg atggttcacg tagtgggcca tcgccctgat    4860
agacggtttt tcgccctttg acgttggagt ccacgttctt taatagtgga ctcttgttcc    4920
```

```
aaactggaac aacactcaac cctatctcgg tctattcttt tgatttataa gggattttgc      4980
cgatttcggc ctattggtta aaaaatgagc tgatttaaca aaaatttaac gcgaattaat      5040
tctgtggaat gtgtgtcagt tagggtgtgg aaagtcccca ggctcccag caggcagaag       5100 tatgcaaagc atgcagaatt ctatcaaata tttaaagaaa aaaaaattgt atcaactttc      5160
tacaatctct ttcagaagac agaagcagag ggaatacttc ctaaatcatt caactaggcc      5220
agcattacct taataccgga actagaaaat gacattacaa gaaaagaaaa caacagacca      5280
atatctctca tgaacaaaga tacaaacatt ttcaacaaaa tattagcaaa agaatccaa       5340 gaatgtatca aaaatatac accacaacca agtagaattt attccagata tgtaagggtg      5400
gttcaacgtt tgaaaatcaa ttaacgtaat ttgtcccatc aacaggttaa agaagaaaat      5460
cacatggtca tattgataga cacagaaaaa gcatttgaca aaatttaaca cccattcatg      5520
atgcaatctc tcagtaaact aggaatagag gaaaacttcc tcagcttgaa tgtaccttcc     5580
tctcaatttt gctatgaacc tgaaactcct cttaaaaaat aaagttttc atttaaaaag       5640 aaaacaaaaa acatggagga gcgttgatgt atctcatttt agaccaatca gctatggata      5700
gttaggcgac agcacagata gctgctgtac ttctgtttct ggcaatgttc cagactacat      5760
ttaaaaaatt tttaattata gacttgtact taatgttcaa gaaaaatatg aaaatggctt      5820
tgccgtgtta atgctactct tttttaaaaa aaactaaagt tcaaacttta tttatatttc      5880
attagttttt tagctactgt tctttttctg ttctgggatc tcattcagaa tgccacatta      5940
catataattc tcatgtctcc ttgggttcct cttagttttg acagttcctc agacttttct      6000
tatttttgat gaccttgaca gttttgagga gtactggtta gatatagggt aatggttttt      6060
aaagtatatt tgtcatgatt tatactgggg taagggtttg gggaggaagc ccatggggta     6120
aagtactgtt ctcatcacat catatcaagg ttatatacca tcaatattgc cacagatgtt      6180
acttagcctt ttaatatttc tcaatttag tgtatatgca atgatagttc tctgatttct       6240
gagattgagt ttctcatgtg taatgattat ttagagtttc tctttcatct gttcaaattt      6300
ttgtctagtt ttattttta ctgatttgta agacttcttt ttataatctg catattacaa       6360
ttctctttac tggggtgttg caaatatttt ctgtcattct atggcctgac tttttcttaat     6420 ggtttttaa tttaaaaat aagtcttaat attcatgcaa tctaattaac aatcttttct        6480
ttgtggttag gactttgagt cataagaaat ttttctctac actgaagtca tgatggcatg      6540
cttctatatt attttctaaa agatttaaag ttttgccttc tccatttaga cttataattc      6600
actgaatttt ttttgtgtgt atggtatgac atatgggttc cctttattt tttacatata       6660 aatatatttc cctgtttttc taaaaagaa aaagatcatc attttcccat tgtaaaatgc       6720 catattttt tcataggtca cttacatata tcaatgggtc tgtttctgag ctctactcta       6780
ttttatcagc ctcactgtct atccccacac atctcatgct tgctctaaa tcttgatatt       6840 tagtggaaca ttctttccca ttttgttcta caagaatatt tttgttattg tcttttgggc      6900
ttctatatac attttagaat gaggttggca agttaacaaa cagctttttt ggggtgaaca      6960
tattgactac aaaatttatgt ggaaagaaag taccaagttg accagtgccg ttccggtgct     7020
caccgcgcgc gacgtcgccg gagcggtcga gttctggacc gaccggctcg ggttctcccg      7080
ggacttcgtg gaggacgact cgccggtgt ggtccgggac gacgtgaccc tgttcatcag       7140
cgcggtccag gaccaggtgg tgccggacaa caccctggcc tgggtgtggg tgcgcggcct      7200
ggacgagctg tacgccgagt ggtcggaggt cgtgtccacg aacttccggg acgcctccgg      7260
```

```
gccggccatg accgagatcg gcgagcagcc gtggggggcgg gagttcgccc tgcgcgaccc    7320
ggccggcaac tgcgtgcact tcgtggccga ggagcaggac tgacacgtgc tacgagattt    7380
cgattccacc gccgccttct atgaaaggtt gggcttcgga atcgttttcc gggacgccgg    7440
ctggatgatc ctccagcgcg gggatctcat gctggagttc ttcgcccacc ccaacttgtt    7500
tattgcagct tataatggtt acaaataaag caatagcatc acaaatttca caaataaagc    7560 attttttca ctgcattcta gttgtggttt gtccaaactc atcaatgtat cttatcatgt    7620
ctgtataccg tcgacctcta gctagagctt ggcgtaatca tggtcatagc tgtttcctgt    7680
gtgaaattgt tatccgctca caattccaca acatacga gccggaagca taaagtgtaa     7740
agcctggggt gcctaatgag tgagctaact cacattaatt gcgttgcgct cactgcccgc    7800
tttccagtcg gaaacctgt cgtgccagct gcattaatga atcggccaac gcgcggggag     7860
aggcggtttg cgtattgggc gctcttccgc ttcctcgctc actgactcgc tgcgctcggt    7920
cgttcggctg cggcgagcgg tatcagctca ctcaaaggcg gtaatacggt tatccacaga    7980
atcaggggat aacgcaggaa agaacatgtg agcaaaaggc cagcaaaagg ccaggaaccg    8040
taaaaaggcc gcgttgctgg cgttttccca taggctccgc cccctgacg agcatcacaa      8100 aaatcgacgc tcaagtcaga ggtggcgaaa cccgacagga ctataaagat accaggcgtt    8160
tccccctgga agctccctcg tgcgctctcc tgttccgacc ctgccgctta ccggatacct    8220
gtccgccttt ctcccttcgg gaagcgtggc gctttctcat agctcacgct gtaggtatct    8280
cagttcggtg taggtcgttc gctccaagct gggctgtgtg cacgaacccc ccgttcagcc    8340
cgaccgctgc gccttatccg gtaactatcg tcttgagtcc aacccggtaa gacacgactt    8400
atcgccactg gcagcagcca ctggtaacag gattagcaga gcgaggtatg taggcggtgc    8460
tacagagttc ttgaagtggt ggcctaacta cggctacact agaagaacag tatttggtat    8520
ctgcgctctg ctgaagccag ttaccttcgg aaaaagagtt ggtagctctt gatccggcaa    8580
acaaaccacc gctggtagcg gttttttgt ttgcaagcag cagattacgc gcagaaaaaa      8640
aggatctcaa gaagatcctt tgatcttttc tacggggtct gacgctcagt ggaacgaaaa    8700
ctcacgttaa gggattttgg tcatgagatt atcaaaaagg atcttcacct agatcctttt     8760
aaattaaaaa tgaagtttta atcaatcta agtatatat gagtaaactt ggtctgacag       8820
ttaccaatgc ttaatcagtg aggcaccta tctcagcgatc tgtctatttc gttcatccat    8880
agttgcctga ctccccgtcg tgtagataac tacgatacgg gagggcttac catctggccc    8940
cagtgctgca atgataccgc gagacccacg ctcaccggct ccagatttat cagcaataaa    9000
ccagccagcc ggaagggccg agcgcagaag tggtcctgca actttatccg cctccatcca    9060
gtctattaat tgttgccggg aagctagagt aagtagttcg ccagttaata gtttgcgcaa    9120
cgttgttgcc attgctacag gcatcgtggt gtcacgctcg tcgtttggta tggcttcatt    9180
cagctccggt tcccaacgat caaggcgagt tacatgatcc cccatgttgt gcaaaaaagc    9240
ggttagctcc ttcggtcctc cgatcgttgt cagaagtaag ttggccgcag tgttatcact    9300
catggttatg gcagcactgc ataattctct tactgtcatg ccatccgtaa gatgcttttc    9360
tgtgactggt gagtactcaa ccaagtcatt ctgagaatag tgtatgcggc gaccgagttg    9420
ctcttgcccg gcgtcaatac gggataatac cgcgccacat agcagaactt taaaagtgct    9480
catcattgga aaacgttctt cggggcgaaa actctcaagg atcttaccgc tgttgagatc    9540
cagttcgatg taacccactc gtgcacccaa ctgatcttca gcatctttta ctttcaccag    9600
cgtttctggg tgagcaaaaa caggaaggca aaatgccgca aaaaagggaa taagggcgac    9660
```

| | |
|---|---|
| acggaaatgt tgaatactca tactcttcct ttttcaatat tattgaagca tttatcaggg | 9720 |
| ttattgtctc atgagcggat acatatttga atgtatttag aaaaataaac aaatagggg | 9780 |
| tccgcgcaca tttccccgaa aagtgccacc tgacgtcgac ggatcgggag atctcccgat | 9840 |
| cccctatggt gcactctcag tacaatctgc tctgatgccg catagttaag ccagtatctg | 9900 |
| ctccctgctt gtgtgttgga ggtcgctgag tagtgcgcga gcaaaattta agctacaaca | 9960 |
| aggcaaggct tgaccgacaa ttgcatgaag aatctgctta gggttaggcg ttttgcgctg | 10020 |
| cttcgcgatg tacgggccag atatacgcgt tgacattgat tattgactag ttattaatag | 10080 |
| taatcaatta cggggtcatt agttcatagc ccatatatgg agttccgcgt tacataactt | 10140 |
| acggtaaatg gcccgcctgg ctgaccgccc aacgacccc gcccattgac gtcaataatg | 10200 |
| acgtatgttc ccatagtaac gccaataggg actttccatt gacgtcaatg ggtggagtat | 10260 |
| ttacggtaaa ctgcccactt ggcagtacat caagtgtatc atatgccaag tacgccccct | 10320 |
| attgacgtca atgacggtaa atggcccgcc tggcattatg cccagtacat gaccttatgg | 10380 |
| gactttccta cttggcagta catctacgta ttagtcatcg ctattaccat ggtgatgcgg | 10440 |
| ttttggcagt acatcaatgg gcgtggatag cggtttgact cacggggatt tccaagtctc | 10500 |
| caccccattg acgtcaatgg gagtttgttt tggaaccaaa atcaacggga ctttccaaaa | 10560 |
| tgtcgtaaca actccgcccc attgacgcaa atgggcggta ggcgtgtacg gtgggaggtc | 10620 |
| tatataagca gagctctccc tatcagtgat agagatctcc ctatcagtga tagagatcgt | 10680 |
| cgacgagctc gtttagtgaa ccgtcagatc gcctggagac gccatccacg ctgttttgac | 10740 |
| ctccatagaa gacaccggga ccgatccagc ctccggactc tagcgtttaa acttaaggct | 10800 |
| agagtactta atacgactca ctatagg | 10827 |

<210> SEQ ID NO 2
<211> LENGTH: 1516
<212> TYPE: DNA
<213> ORGANISM: Artificial Sequence
<220> FEATURE:
<223> OTHER INFORMATION: Synthetic Oligonucleotide

<400> SEQUENCE: 2

| | |
|---|---|
| atgagcctgt ggctgcccag cgaggccacc gtgtacctgc cccccgtgcc cgtgagcaag | 60 |
| gtggtgagca ccgacgagta cgtggccaga accaacatct actaccacgc ggcaccagc | 120 |
| agactgctgg ccgtgggcca cccctacttc cccatcaaga agcccaacaa caacaagatc | 180 |
| ctggtgccca aggtgagcgg cctgcagtac agagtgttca gaatccacct gcccgacccc | 240 |
| aacaagttcg gcttccccga caccagcttc tacaaccccg acacccagag actggtgtgg | 300 |
| gcctgcgtgg gcgtggaggt gggcagaggc cagcccctgg gcgtgggcat cagcggccac | 360 |
| cccctgctga caagctgga cgacaccgag aacgccagcg cctacgccgc caacgccggc | 420 |
| gtggacaaca gagagtgcat cagcatggac tacaagcaga cccagctgtg cctgatcggc | 480 |
| tgcaagcccc ccatcggcga gcactgggc aagggcagcc cctgcaccaa cgtggccgtg | 540 |
| aaccccggcg actgcccccc cctggagctg atcaacaccg tgatccagga cggcgacatg | 600 |
| gtggacaccg gcttcggcgc catggacttc accacccctgc aggccaacaa gagcgaggtg | 660 |
| cccctggaca tctgcaccag catctgcaag taccccgact acatcaagat ggtgagcgag | 720 |
| ccctacggcg acagcctgtt cttctacctg agaagagagc agatgttcgt gagacacctg | 780 |
| ttcaacagag ccggcgccgt gggcgagaac gtgcccaccg acctgtacat caagggcagc | 840 |

```
ggcagcaccg ccaccctggc caacagcaac tacttcccca cccccagcgg cagcatggtg      900
accagcgacg cccagatctt caacaagccc tactggctgc agagagccca gggccacaac      960
aacggcatct gctggggcaa ccagctgttc gtgaccgtgg tggacaccac cagaagcacc     1020
aacatgagcc tgtgcgccgc catcagcacc agcgagacca cctacaagaa caccaacttc     1080
aaggagtacc tgagacacgg cgaggagtac gacctgcagt tcatcttcca gctgtgcaag     1140
atcaccctga ccgccgacgt gatgacctac atccacagca tgaacagcac catcctggag     1200
gactggaact tcggcctgca gccccccccc ggcggcaccc tggaggacac ctacagattc     1260
gtgaccagcc aggccatcgc ctgccagaag cacacccccc ccgcccccaa ggaggacccc     1320
ctgaagaagt acaccttctg ggaggtgaac ctgaaggaga gttcagcgc cgacctggac      1380 cagttccccc tgggcagaaa gttcctgctg caggccggcc tgaaggccaa gcccaagttc     1440
accctgggca agagaaaggc caccccccacc accagcagca ccagcaccac cgccaagaga    1500
aagaagagaa agctga                                                     1516
```

<210> SEQ ID NO 3
<211> LENGTH: 6754
<212> TYPE: DNA
<213> ORGANISM: Artificial Sequence
<220> FEATURE:
<223> OTHER INFORMATION: Synthetic Oligonucleotide

<400> SEQUENCE: 3

```
atccggatat agttcctcct ttcagcaaaa aaccccctcaa gacccgttta gaggccccaa       60
ggggttatgc tagttattgc tcagcggtgg cagcagccaa ctcagcttcc tttcgggctt      120
tgttagcagc cggatctcag tggtggtggt ggtggtgctc gagtcattac agtttacgct      180
tcttacgctt cgcggtggtg ctagtgctgc tggtggtcgg cgtggccttg cgcttgccca      240
gggtaaactt cggttttgcc ttcagacccg cttgcagcag gaatttgcgg cccagcggaa      300
actggtccaa atcagccgag aatttctctt tcagattgac ctcccaaaag gtgtatttct      360
tcagcggatc ttctttcggt gccggtgggg tatgcttctg acacgcgatt gcctgggagg      420
taacaaaacg gtacgtatcc tccagcgtgc cgccaggcgg aggttgcaga ccgaagttcc      480
aatcctccag aatcgtgctg ttcatgctat gaatgtagct catcacgtcc gccgtcaggg      540
tgattttaca cagctgaaaa atgaattgca gatcatattc ttcgccgtga cgcagatatt      600
ctttaaagtt ggtattctta taggtcggct cgctggtcga gatcgctgca cacaggctca      660
tattcgtgct gcgcgtagtg tcaaccacgg taacaaacag ttgattaccc cagcaaatac      720
cattattgtg accctgtgca cgttgcagcc agtaaggctt attgaaaatc tgagcatcgc      780
tagtaaccat gctgccgctt ggcgtcggaa agtaattgct gttcgccaac gtcgcggtgc      840
taccgctacc tttgatgtac aggtcagtcg gcacgttctc acccacggca cctgcgcgat      900
tgaacaggtg acggacgaac atttgctcgc gacgcaggta aaagaacagg ctgtcaccat      960
acggttcgct gaccattttg atatagtccg ggtacttgca gatagaggtg caaatgtcca     1020
acggaacctc gctcttgttg gcctgcaagg tggtaaagtc catcgcacca agcccgtat      1080 ccaccatatc accatcttga atcaccgtat tgatcagttc cagcggtggg caatcacccg     1140
gattcaccgc cacgttattg cacgggctac ctttacccca gtgctcaccg atcggcggtt     1200
tacaaccgat caggcacagc tgggtttgct tatagtccat cgaaatgcat tcacgattat     1260
ccacgcctgc gttcgcggcg taggcagaag cgttctcggt atcgtccagt ttgttcagca     1320
gcggatggcc ggagatgccg acgcccagcg gctgaccacg accaacctca acgccgacac     1380
```

```
acgcccaaac cagacgctgc gtgtccgggt tatagaagct ggtgtccggg aaaccgaatt    1440
tgttcgggtc acgcagatga atgcggaaca cacgatattg caagccgctg accttcggta    1500
ccagaatttt gttgttgttc ggtttcttaa tcgggaaata cgggtgaccc acggccaaca    1560
ggcgggacgt acccgcgtgg tagtagatat tggtgcgcgc gacgtattcg tcggtagaga    1620
caaccttgct aactgggaca ggcggtaagt acacggtcgc ttcgctcggg agccacaggg    1680
acattttttt tatctccttt aaagttaaac aaaattattt ctagagggga attgttatcc    1740
gctcacaatt ccctatagt gagtcgtatt aatttcgcgg gatcgagatc tcgatcctct    1800
acgccggacg catcgtggcc ggcatcaccg gcgccacagg tgcggttgct ggcgcctata    1860
tcgccgacat caccgatggg gaagatcggg ctcgccactt cgggctcatg agcgcttgtt    1920
tcggcgtggg tatggtggca ggccccgtgg ccggggggact gttgggcgcc atctccttgc    1980
atgcaccatt ccttgcggcg gcggtgctca acggcctcaa cctactactg ggctgcttcc    2040
taatgcagga gtcgcataag ggagagcgtc gagatcccgg acaccatcga atggcgcaaa    2100
acctttcgcg gtatggcatg atagcgcccg gaagagagtc aattcagggt ggtgaatgtg    2160
aaaccagtaa cgttatacga tgtcgcagag tatgccggtg tctcttatca gaccgtttcc    2220
cgcgtggtga accaggccag ccacgtttct gcgaaaacgc gggaaaaagt ggaagcggcg    2280
atggcggagc tgaattacat tcccaaccgc gtggcacaac aactggcggg caaacagtcg    2340
ttgctgattg gcgttgccac ctccagtctg gccctgcacg cgccgtcgca aattgtcgcg    2400
gcgattaaat ctcgcgccga tcaactgggt gccagcgtgg tggtgtcgat ggtagaacga    2460
agcggcgtcg aagcctgtaa agcggcggtg cacaatcttc tcgcgcaacg cgtcagtggg    2520
ctgatcatta actatccgct ggatgaccag gatgccattg ctgtggaagc tgcctgcact    2580
aatgttccgg cgttatttct tgatgtctct gaccagacac ccatcaacag tattattttc    2640
tcccatgaag acggtacgcg actgggcgtg gagcatctgg tcgcattggg tcaccagcaa    2700
atcgcgctgt tagcgggccc attaagttct gtctcggcgc gtctgcgtct ggctggctgg    2760
cataaatatc tcactcgcaa tcaaattcag ccgatagcgg aacgggaagg cgactggagt    2820
gccatgtccg gttttcaaca aaccatgcaa atgctgaatg agggcatcgt tcccactgcg    2880
atgctggttg ccaacgatca gatggcgctg ggcgcaatgc gcgccattac cgagtccggg    2940
ctgcgcgttg tgcggatat ctcggtagtg ggatacgacg ataccgaaga cagctcatgt    3000
tatatcccgc cgttaaccac catcaaacag gattttcgcc tgctggggca aaccagcgtg    3060
gaccgcttgc tgcaactctc tcagggccag gcggtgaagg gcaatcagct gttgcccgtc    3120
tcactggtga aaagaaaaac caccctggcg cccaatacgc aaaccgcctc tccccgcgcg    3180
ttggccgatt cattaatgca gctggcacga caggtttccc gactgaaaag cgggcagtga    3240
gcgcaacgca attaatgtaa gttagctcac tcattaggca ccgggatctc gaccgatgcc    3300
cttgagagcc ttcaacccag tcagctcctt ccggtgggcg cggggcatga ctatcgtcgc    3360
cgcacttatg actgtcttct ttatcatgca actcgtagga caggtgccgg cagcgctctg    3420
ggtcattttc ggcgaggacc gctttcgctg gagcgcgacg atgatcggcc tgtcgcttgc    3480
ggtattcgga atcttgcacg ccctcgctca agccttcgtc actggtcccg ccaccaaacg    3540
tttcggcgag aagcaggcca ttatcgccgg catggcggcc ccacgggtgc gcatgatcgt    3600
gctcctgtcg ttgaggaccc ggctaggctg gcggggttgc cttactggtt agcagaatga    3660
atcaccgata cgcgagcgaa cgtgaagcga ctgctgctgc aaaacgtctg cgacctgagc    3720
```

```
aacaacatga atggtcttcg gtttccgtgt ttcgtaaagt ctggaaacgc ggaagtcagc    3780
gccctgcacc attatgttcc ggatctgcat cgcaggatgc tgctggctac cctgtggaac    3840
acctacatct gtattaacga agcgctggca ttgaccctga gtgattttc tctggtcccg     3900 ccgcatccat accgccagtt gtttacccc acaacgttcc agtaaccggg catgttcatc     3960
atcagtaacc cgtatcgtga gcatcctctc tcgtttcatc ggtatcatta ccccatgaa     4020 cagaaatccc ccttacacgg aggcatcagt gaccaaacag gaaaaaaccg cccttaacat    4080
ggcccgcttt atcagaagcc agacattaac gcttctggag aaactcaacg agctggacgc    4140
ggatgaacag gcagacatct gtgaatcgct tcacgaccac gctgatgagc tttaccgcag    4200
ctgcctcgcg cgtttcggtg atgacggtga aaacctctga cacatgcagc tcccggagac    4260
ggtcacagct tgtctgtaag cggatgccgg gagcagacaa gcccgtcagg gcgcgtcagc    4320
gggtgttggc gggtgtcggg gcgcagccat gacccagtca cgtagcgata gcggagtgta    4380
tactggctta actatgcggc atcagagcag attgtactga gagtgcacca tatatgcggt    4440
gtgaaatacc gcacagatgc gtaaggagaa ataccgcat caggcgctct ccgcttcct     4500 cgctcactga ctcgctgcgc tcggtcgttc ggctgcggcg agcggtatca gctcactcaa    4560
aggcggtaat acggttatcc acagaatcag gggataacgc aggaaagaac atgtgagcaa    4620
aaggccagca aaaggccagg aaccgtaaaa aggccgcgtt gctggcgttt ttccataggc    4680
tccgcccccc tgacgagcat cacaaaaatc gacgctcaag tcagaggtgg cgaaacccga    4740
caggactata agataccag gcgtttcccc ctggaagctc cctcgtgcgc tctcctgttc     4800
cgaccctgcc gcttaccgga tacctgtccg ccttttctccc ttcgggaagc gtggcgcttt    4860
ctcatagctc acgctgtagg tatctcagtt cggtgtaggt cgttcgctcc aagctgggct    4920
gtgtgcacga accccccgtt cagcccgacc gctgcgcctt atccggtaac tatcgtcttg    4980
agtccaaccc ggtaagacac gacttatcgc cactggcagc agccactggt aacaggatta    5040
gcagagcgag gtatgtaggc ggtgctacag agttcttgaa gtggtggcct aactacggct    5100
acactagaag gacagtattt ggtatctgcg ctctgctgaa gccagttacc ttcggaaaaa    5160
gagttggtag ctcttgatcc ggcaaacaaa ccaccgctgg tagcggtggt ttttttgttt    5220
gcaagcagca gattacgcgc agaaaaaaag gatctcaaga agatcctttg atcttttcta    5280
cggggtctga cgctcagtgg aacgaaaact cacgttaagg gattttggtc atgaacaata    5340
aaactgtctg cttacataaa cagtaataca agggggtgtta tgagccatat tcaacgggaa    5400
acgtcttgct ctaggccgcg attaaattcc aacatggatg ctgatttata tgggtataaa    5460
tgggctcgcg ataatgtcgg gcaatcaggt gcgacaatct atcgattgta tgggaagccc    5520
gatgcgccag agttgtttct gaaacatggc aaaggtagcg ttgccaatga tgttacagat    5580
gagatggtca gactaaactg gctgacggaa tttatgcctc ttccgaccat caagcatttt    5640
atccgtactc ctgatgatgc atggttactc accactgcga tccccgggaa aacagcattc    5700
caggtattag aagaatatcc tgattcaggt gaaaatattg ttgatgcgct ggcagtgttc    5760
ctgcgccggt tgcattcgat tcctgttttgt aattgtcctt ttaacagcga tcgcgtattt    5820
cgtctcgctc aggcgcaatc acgaatgaat aacggtttgg ttgatgcgag tgattttgat    5880
gacgagcgta atggctggcc tgttgaacaa gtctggaaag aaatgcataa acttttgcca    5940
ttctcaccgg attcagtcgt cactcatggt gatttctcac ttgataacct tattttttgac   6000 gaggggaaat taataggttg tattgatgtt ggacgagtcg gaatcgcaga ccgataccag    6060
gatcttgcca tcctatggaa ctgcctcggt gagttttctc cttcattaca gaaacggctt    6120
```

```
tttcaaaaat atggtattga taatcctgat atgaataaat tgcagtttca tttgatgctc     6180
gatgagtttt tctaagaatt aattcatgag cggatacata tttgaatgta tttagaaaaa     6240
taaacaaata ggggttccgc gcacatttcc ccgaaaagtg ccacctgaaa ttgtaaacgt     6300
taatattttg ttaaaattcg cgttaaattt ttgttaaatc agctcatttt ttaaccaata     6360
ggccgaaatc ggcaaaatcc cttataaatc aaagaatag accgagatag ggttgagtgt      6420
tgttccagtt tggaacaaga gtccactatt aagaacgtg gactccaacg tcaaagggcg      6480 aaaaccgtc tatcagggcg atggcccact acgtgaacca tcaccctaat caagtttttt      6540
ggggtcgagg tgccgtaaag cactaaatcg aaccctaaa gggagccccc gatttagagc      6600
ttgacgggga agccggcga acgtggcgag aaaggaaggg aagaaagcga aaggagcggg      6660
cgctagggcg ctggcaagtg tagcggtcac gctgcgcgta accaccacac ccgccgcgct     6720
taatgcgccg ctacagggcg cgtcccattc gcca                                 6754

<210> SEQ ID NO 4
<211> LENGTH: 5386
<212> TYPE: DNA
<213> ORGANISM: Artificial Sequence
<220> FEATURE:
<223> OTHER INFORMATION: Synthetic Oligonucleotide

<400> SEQUENCE: 4
aagaaaccaa ttgtccatat tgcatcagac attgccgtca ctgcgtcttt tactggctct       60
tctcgctaac caaaccggta accccgctta ttaaaagcat tctgtaacaa agcgggacca      120
aagccatgac aaaaacgcgt aacaaaagtg tctataatca cggcagaaaa gtccacattg      180
attatttgca cggcgtcaca ctttgctatg ccatagcatt tttatccata agattagcgg      240
atcctacctg acgcttttta tcgcaactct ctactgtttc tccatacccg ttttttgggc      300
taacaggagg aattaaccat gagacacaaa agatcagcca aacgtacgaa gagagcaagc      360
gcgacccaac tgtataagac ctgcaaacag gcgggtactt gtccgcctga catcatccct      420
aaggttgagg gtaagaccat cgcggatcaa attctgcaat acggcagcat gggcgttttc      480
tttggtggcc tgggtattgg tacgggtagc ggcaccggcg tcgtaccgg ctacatcccg      540 ctgggcaccc gcccaccgac cgccaccgat acgctggccc cagtgcgtcc gccgctgacc      600
gtcgatccgt tgcccgtc cgacccgagc attgttagcc tggtggaaga aaccagcttc       660
attgatgcgg gtgctcctac gagcgttccg tctatcccgc cagacgtgag cggttttagc      720
attacgacga gcaccgatac cacccggct attttggaca ttaacaacac ggtgactacc      780
gtgaccaccc acaacaatcc tacctttact gacccaagcg tgttgcaacc gccgacccg      840 gcagaaacg gtgccactt caccctgagc agctccacca tcagcacgca caattatgaa       900
gagattccga tggacacctt tatcgtatct acgaatccga atacggtcac gagcagcacc      960
ccgattccgg gctcccgtcc ggtcgcgcgt ctggtctgt actcccgtac cacccagcag     1020
gttaaagtcg ttgacccggc gtttgttacg accccgacga agctgattac ctatgacaat     1080
ccggcctacg agggcattga cgttgataac accctgtact tcagcagcaa cgataatagc     1140
atcaatattg caccggaccc tgatttttctg gacatcgtcg cactgcaccg tccggcgctg     1200
acgagccgtc gcacgggtat tcgttattcc cgcatcggca acaaacaaac cctgcgcacc     1260
cgttcgggta agtctatcgg cgcaaaaagtc cattactatt cgacctgtc taccatcgat     1320 ccggcggaag agattgagtt gcagacgatt actccgagca cctacaccac tacgtcccat     1380
```

```
gcagcgagcc cgaccagcat caacaatggt ctgtacgaca tctatgcgga tgactttatc    1440
actgatacga gcaccacgcc ggtcccgagc gtgccgagca ccagcctgtc gggctatatc    1500
ccggccaaca ccacgattcc gttcggtggt gcgtataaca tcccgttggt gagcggtcca    1560
gacatcccga tcaacattac ggatcaggca ccgagcctga ttccgatcgt cccgggtagc    1620
ccacagtaca ccatcattgc tgatgcaggt gacttctacc tgcatccgtc ttactatatg    1680
ttgcgtaaac gccgcaagcg tctgccgtac ttcttctcgg atgtgagcct ggcggcgtaa    1740
tgaattcgaa gcttggctgt tttggcggat gagagaagat tttcagcctg atacagatta    1800
aatcagaacg cagaagcggt ctgataaaac agaatttgcc tggcggcagt agcgcggtgg    1860
tcccacctga ccccatgccg aactcagaag tgaaacgccg tagcgccgat ggtagtgtgg    1920
ggtctcccca tgcgagagta gggaactgcc aggcatcaaa taaaacgaaa ggctcagtcg    1980
aaagactggg cctttcgttt tatctgttgt ttgtcggtga acgctctcct gagtaggaca    2040
aatccgccgg gagcggattt gaacgttgcg aagcaacggc ccggagggtg gcgggcagga    2100
cgcccgccat aaactgccag gcatcaaatt aagcagaagg ccatcctgac ggatggcctt    2160
tttgcgtttc tacaaactct tttgtttatt ttctaaata cattcaaata tgtatccgct    2220
catgagacaa taaccctgat aaatgcttca ataatattga aaaggaaga gtatgagtat    2280 tcaacatttc cgtgtcgccc ttattcccctt ttttgcggca ttttgccttc ctgttttttgc    2340 tcacccagaa acgctggtga agtaaaaga tgctgaagat cagttgggtg cacgagtggg    2400
ttacatcgaa ctggatctca acagcggtaa gatccttgag agttttcgcc ccgaagaacg    2460
ttttccaatg atgagcactt ttaaagttct gctatgtggc gcggtattat cccgtgttga    2520
cgccgggcaa gagcaactcg gtcgccgcat acactattct cagaatgact tggttgagta    2580
ctcaccagtc acagaaaagc atcttacgga tggcatgaca gtaagagaat tatgcagtgc    2640
tgccataacc atgagtgata acactgcggc caacttactt ctgacaacga tcggaggacc    2700
gaaggagcta accgcttttt tgcacaacat ggggatcat gtaactcgcc ttgatcgttg    2760
ggaaccggag ctgaatgaag ccataccaaa cgacgagcgt gacaccacga tgcctgtagc    2820
aatggcaaca acgttgcgca aactattaac tggcgaacta cttactctag cttcccggca    2880
acaattaata gactggatgg aggcggataa agttgcagga ccacttctgc gctcggccct    2940
tccggctggc tggtttattg ctgataaatc tggagccggt gagcgtgggt ctcgcggtat    3000
cattgcagca ctggggccag atggtaagcc ctcccgtatc gtagttatct acacgacggg    3060
gagtcaggca actatggatg aacgaaatag acagatcgct gagataggtg cctcactgat    3120
taagcattgg taactgtcag accaagttta ctcatatata ctttagattg atttaaaact    3180 tcattttaa tttaaaagga tctaggtgaa gatcctttt gataatctca tgaccaaaat    3240
cccttaacgt gagttttcgt tccactgagc gtcagacccc gtagaaaaga tcaaaggatc    3300
ttcttgagat cctttttttc tgcgcgtaat ctgctgcttg caaacaaaaa aaccaccgct    3360
accagcggtg gtttgtttgc cggatcaaga gctaccaact cttttccga aggtaactgg    3420 cttcagcaga gcgcagatac caaatactgt ccttctagtg tagccgtagt taggccacca    3480
cttcaagaac tctgtagcac cgcctacata cctcgctctg ctaatcctgt taccagtggc    3540
tgctgccagt ggcgataagt cgtgtcttac cgggttggac tcaagacgat agttaccgga    3600
taaggcgcag cggtcgggct gaacggggg ttcgtgcaca cagcccagct tggagcgaac    3660
gacctacacc gaactgagat acctacacgcg tgagctatga gaaagcgcca cgcttcccga    3720
agggagaaag gcggacaggt atccggtaag cggcagggtc ggaacaggag agcgcacgag    3780
```

-continued

```
ggagcttcca gggggaaacg cctggtatct ttatagtcct gtcgggtttc gccacctctg    3840
acttgagcgt cgattttgt gatgctcgtc aggggggcgg agcctatgga aaaacgccag     3900
caacgcggcc tttttacggt tcctggcctt ttgctggcct tttgctcaca tgttctttcc    3960
tgcgttatcc cctgattctg tggataaccg tattaccgcc tttgagtgag ctgataccgc    4020
tcgccgcagc cgaacgaccg agcgcagcga gtcagtgagc gaggaagcgg aagagcgcct    4080
gatgcggtat tttctcctta cgcatctgtg cggtatttca caccgcatat ggtgcactct    4140
cagtacaatc tgctctgatg ccgcatagtt aagccagtat acactccgct atcgctacgt    4200
gactgggtca tggctgcgcc ccgacacccg ccaacacccg ctgacgcgcc ctgacgggct    4260
tgtctgctcc cggcatccgc ttacagacaa gctgtgaccg tctccgggag ctgcatgtgt    4320
cagaggtttt caccgtcatc accgaaacgc gcgaggcagc agatcaattc gcgcgcgaag    4380
gcgaagcggc atgcataatg tgcctgtcaa atggacgaag cagggattct gcaaaccta     4440 tgctactccg tcaagccgtc aattgtctga ttcgttacca attatgacaa cttgacggct    4500
acatcattca cttttcttc acaaccggca cggaactcgc tcgggctggc cccggtgcat     4560
tttttaaata cccgcgagaa atagagttga tcgtcaaaac caacattgcg accgacggtg    4620
gcgataggca tccgggtggt gctcaaaagc agcttcgcct ggctgatacg ttggtcctcg    4680
cgccagctta agacgctaat ccctaactgc tggcggaaaa gatgtgacag acgcgacggc    4740
gacaagcaaa catgctgtgc gacgctggcg atatcaaaat tgctgtctgc caggtgatcg    4800
ctgatgtact gacaagcctc gcgtacccga ttatccatcg gtggatggag cgactcgtta    4860
atcgcttcca tgcgccgcag taacaattgc tcaagcagat ttatcgccag cagctccgaa    4920
tagcgccctt cccttgccc ggcgttaatg atttgcccaa acaggtcgct gaaatgcggc     4980
tggtgcgctt catccgggcg aaagaacccc gtattggcaa atattgacgg ccagttaagc    5040
cattcatgcc agtaggcgcg cggacgaaag taaacccact ggtgatacca ttcgcgagcc    5100
tccggatgac gaccgtagtg atgaatctct cctggcggga acagcaaaat atcacccggt    5160
cggcaaacaa attctcgtcc ctgattttc accacccct gaccgcgaat ggtgagattg      5220
agaatataac ctttcattcc cagcggtcgg tcgataaaaa aatcgagata accgttggcc    5280
tcaatcggcg ttaaacccgc caccagatgg gcattaaacg agtatcccgg cagcaggga    5340 tcattttgcg cttcagccat acttttcata ctcccgccat tcagag                   5386
```

US 10,300,150 B2

VIRION-DERIVED NANOSPHERES FOR SELECTIVE DELIVERY OF THERAPEUTIC AND DIAGNOSTIC AGENTS TO CANCER CELLS

RELATED APPLICATIONS

This application is a continuation of U.S. application Ser. No. 15/615,485, filed Jun. 6, 2017, which is a continuation of U.S. application Ser. No. 14/376,408, filed Aug. 1, 2014, now U.S. Pat. No. 9,700,639, which is a national stage filing under U.S.C. § 371 of International application number PCT/US2013/025230, filed Feb. 7, 2013, which was published under PCT Article 21(2) in English and claims the benefit under 35 U.S.C. § 119(e) of U.S. provisional application Ser. No. 61/596,042, filed Feb. 7, 2012, each of which is herein incorporated by reference in its entirety.

FIELD OF INVENTION

Embodiments described herein relate to the fields of molecular biology and medicine.

BACKGROUND OF THE INVENTION

Many therapeutic agents cannot be delivered effectively to treat cancerous cells by conventional means such as ingestion, injection, inhalation, and topical application because many of these agents are subject to rapid degradation. Further, direct systemic administration of many therapeutic agents often causes detrimental side-effects. For example, those agents that target actively dividing cells are not able to discriminate between actively dividing cancer cells and actively dividing healthy cells. Thus, in the process of destroying or inhibiting the rapidly dividing cancer cells, many of the healthy cells are also damaged.

Accordingly, there is an unmet need for targeting of solid tumor cells for the treatment of malignant diseases that will show an affinity for cancer cells, deliver therapeutic payloads that inhibit proliferation and/or destroy cancerous tumor cells without inhibiting and/or destroying normal cells.

SUMMARY OF INVENTION

In some embodiments, aspects of the invention relate to methods and compositions for delivering therapeutic and/or diagnostic agents to a target tissue in a subject (e.g., mammal such as human). In some embodiments, methods and compositions are provided for creating and using virion-derived protein nanosphere particles (NSPs) that exhibit surprising selectivity for delivering molecules to tumors without targeting healthy tissue and without producing a serotype-specific immunogenic response in the subject. Accordingly, NSPs described herein are useful for delivering toxic agents to tumors with reduced risk to healthy cells. However, NSPs described herein also may be used to selectively deliver other therapeutic and/or diagnostic agents as aspects of the invention are not limited in this respect.

In some embodiments, aspects of the invention are based on the selective tropism of NSPs described herein for tumor cells. The proliferation of tumor cells is characterized by inflammation of tumor sites, the ability of tumor cells to evolve HSPG (heparan sulphate proteoglycans) in a similar manner to basal membrane Keratinocytes, and the presence of various growth factor receptors known to congregate at the surface of tumor cells. In some embodiments, nanosphere particles described herein are attracted to one of more of these tumor specific properties.

Thus, in some aspects, provided herein are methods of selectively delivering an agent to at least one tumor (e.g., one or more) in a subject, the method comprising administering a tumor tropic nanosphere particle to a subject, wherein the tumor tropic nanosphere particle comprises mutated or modified human papillomavirus (HPV) L1 capsid protein without a heterologous targeting agent, is associated with an agent, and is free of host cell nucleic acid and viral nucleic acid. In some embodiments, the nanosphere particle comprises wild-type HPV L2 capsid proteins. In some embodiments, the mutated HPV L1 capsid protein has an amino acid sequence alteration that modifies in the subject HPV serotype-specific immunogenicity of the capsid protein relative to a naturally-occurring capsid protein. In some embodiments, the mutated HPV L1 capsid protein has an amino acid sequence alteration that prevents in the subject HPV serotype-specific immunogenicity of the capsid protein relative to a naturally-occurring capsid protein. In some embodiments, the mutated HPV L1 capsid protein is a mutated HPV-16 or HPV-31 L1 capsid protein. In some embodiments, the mutated HPV L1 capsid protein comprises the amino acid sequence of SEQ ID NO:2.

In some embodiments, the modified HPV L1 capsid protein has an amino acid that is PEGylated.

In some embodiments, the at least one tumor is pre-malignant or malignant. In some embodiments, the at least one tumor is metastatic. In some embodiments, the at least one tumor is a non-mucosal tumor. In some embodiments, the at least one tumor is a solid tumor. In some embodiments, the at least one tumor contains cancer stem cells. In some embodiments, the at least one tumor is an astrocytoma, an atypical teratoid rhaboid tumor, a bone or connective tissue tumor, a brain cyst, a choroid plexus tumor, a craniopharyngioma, an ependymoma, a germ cell tumor, a glioblastoma, a glioma, a hemangioma, a juvenile pilocytic astrocytoma, a lipoma, a lymphoma, a medulloblastoma, a meningioma, a neurofibroma, a neuronal tumor, a mixed neuronal-glial tumor, an oligoastrocytoma, and oligodendroglioma, a pineal tumor, a pituitary tumor, a primitive neuroectodermal tumor or a schwannoma. In some embodiments, the at least one tumor is located in the breast, cervix, ovary, testis, prostate, lung, lymph node, stomach, intestine, colon, brain, or a combination thereof.

In some embodiments, the agent is a therapeutic agent. In some embodiments, the agent is an anti-cancer agent. In some embodiments, the anti-cancer agent is delivered to the subject in a therapeutically effective amount to treat (e.g., shrink or irradicate) the tumor.

In some embodiments, the therapeutic agent is an inorganic molecule, an organic molecule or a biologically active molecule. In some embodiments, the therapeutic agent comprises a small molecule, a protein, a peptide, an antibody, a toxin, a nucleic acid, a radioisotope, a radiolabeled molecule, a metal, an inducer of DNA methylation, a modulator of gene expression, an immune modulator, an enzyme inhibitor, a kinase inhibitor, an apoptosis inducer, a metabolism inhibitor, or any combination thereof. In some embodiments, the therapeutic agent is a radioisotope or a radiolabeled molecule. In some embodiments, the nucleic acid is an siRNA molecule, an shRNA molecule, a microRNA, a long non coding RNA, a hybrid DNA-RNA, a DNA molecule, an antisense molecule, a viral gene cassette, or any combination thereof.

In some embodiments, the agent is a diagnostic agent. In some embodiments, the diagnostic agent is an imaging agent or a contrast agent. In some embodiments, the diagnostic agent is labeled with a detectable label. In some embodiments, the detectable label is a fluorescent or radioactive label.

In some embodiments, the agent is encapsulated with the nanosphere particle. In some embodiments, the agent is mixed with the capsid proteins in the nanosphere particle. In some embodiments, the agent is chemically linked to an amino acid of one or more capsid proteins in the nanosphere particle.

In some embodiments, the mutated HPV L1 capsid protein is expressed, isolated and purified as a monomer or as an oligomeric capsomere from a host cell expression system. In some embodiments, the mutated HPV L1 capsid protein and the L2 capsid protein are expressed from different nucleic acids in a host cell expression system. In some embodiments, the host cell expression system is a bacterial, a yeast, an insect, a plant or a mammalian host cell expression system. In some embodiments, the bacterial host cell expression system is an *Escherichia coli* host cell expression system. In some embodiments, the capsid proteins and/or capsomeres are assembled in vitro to form the nanosphere particle.

In some aspects, provided herein are methods of producing a nanosphere particle for selectively delivering a therapeutic or diagnostic agent to a tumor in a subject, the method comprising, providing mutated or modified human papillomavirus (HPV) L1 capsid protein that is free of (without detectable amounts or the detectable level is very low, e.g., less than 1%, less than 0.5%, less than 0.1%, less than 0.05%, or less than 0.01% relative to the capsid proteins) host cell nucleic acid and viral nucleic acid, and reassembling the capsid protein in the presence of a therapeutic agent or diagnostic agent.

In some aspects, provided herein are methods of producing a nanosphere particle loaded with a therapeutic or diagnostic agent, the method comprising, recombinantly expressing mutated human papillomavirus (HPV) L1 capsid protein mutant and wild-type HPV L2 capsid protein in bacterial cells; isolating mutated HPV L1 capsid protein, wild-type HPV L2 capsid protein, mutated HPV L1 capsomeres, mutated HPV L1/wild-type L2 capsomeres, or a combination thereof; combining the capsid proteins and/or capsomeres with the agent and reassembly buffer containing salt and HEPES buffer, or salt and Histidine-HCl buffer; and dialyzing the combination of protein and reassembly buffer to produce HPV nanosphere particles loaded with the agent. In some embodiments, the reassembly buffer contains 0.5M NaCl, 5 mM CaCl2, and 40 mM HEPES (pH 6.8), or (2) 0.5M NaCl, 5 mM CaCl2, and 40 mM Histidine-HCl (pH 5.2).

In some aspects provided herein are methods of delivering and evaluating a cancer therapy comprising: (a) identifying a subject with cancer; (b) labeling tumor tropic nanosphere particles; (c) loading the tumor tropic nanosphere particles with a therapeutic agent; (d) administering a detectable amount of the nanosphere particles to the subject; and (e) determining the presence or amount of the nanosphere particles in the subject during and after a period of a treatment. In some embodiments, the label is selected from the group consisting of a fluorescent label, a radioactive label and a chemiluminescent label.

For some viruses and other pathogens, tropism is recognized as a natural phenomenon which may be referred to as "host tropism" or "cell tropism" in which tropism refers to the way in which different viruses/pathogens have evolved to preferentially target specific host species. For example, HIV has a glycoprotein (gp120) which recognizes and binds specifically to the CD4 surface receptor cells of macrophages and T cells. In this example, the CD4 receptor cells and other necessary cofactors act as a stimulus in attracting human immunodeficiency virus to the surface of an immune cell. Recombinant Adeno Associated Virus (AAV) virions have been shown to exhibit tropism for respiratory epithelial cells (Flotte et al. 1992 *Am. J. Respir. Cell Mol. Biol.* 7:349-356).

According to aspects of the invention, NSPs derived from proteins of certain viruses described herein exhibit broad tumor tropism also referred to herein as universal tumor tropism. Accordingly, NSPs described herein can be used for targeting one or more tumors with a therapeutic agent, for example in a subject diagnosed as having cancer. In some embodiments, the term "subject" includes animals, such as warm-blooded mammals, for example, humans and primates; avians; domestic household or farm animals such as cats, dogs, sheep, goats, cattle, horses and pigs; laboratory animals such as mice, rats and guinea pigs; fish; reptiles; zoo and wild animals; and the like. Also, in some embodiments, NSPs described herein can be used to detect cancer in a subject by selectively delivering a diagnostic agent (for example a detectable agent, a contrast agent, or other diagnostic agent) to cancer tissue. In some embodiments, this can increase the detectability of cancer tissue or cells and/or enhance the contrast between cancer tissue or cells and surrounding healthy tissue, thereby assisting in the detection or diagnosis of cancer. It should be appreciated that diagnostic reagents described herein can be used alone or in combination with other diagnostic procedures to help detect or diagnose cancer.

In some embodiments, NSPs described herein can be used to target any tumor, because the NSPs do not discriminate between different tumor cells (e.g., relative to their preference of tumor cells over non-tumor cells). Contrary to expectations, NSPs described herein (e.g., NSPs containing mutated HPV L2 capsid proteins) display a strong universal tumor tropism for all types of tumor cells lines tested. In addition, in some embodiments NSPs described herein that are not taken up by solid tumor cells will be innocuously eliminated through normal biological routes. For example, NSPs that lack any viral genetic material or host cell genetic material will not replicate and will be eliminated without damaging healthy cells.

NSPs of the present invention provide a novel combination of viral proteins that can be assembled with drugs or diagnostic agents, and that have been shown to display a universal tumor tropism. Surprisingly, in some embodiments, modified NSPs having reduced or altered immunogenicity retain their ability to identify tumors with the same mechanism previously described by universal tumor tropism. Accordingly, modified NSPs (e.g., modified to reduce or prevent cross-reactivity with host antibodies, for example HPV antibodies) can be modified to deliver reagents (e.g., as surface modifications, as fusion proteins, and/or encapsulated or mixed within the structure of the NSP) selectively to tumor tissue or cells (e.g., to solid tumors). In some embodiments, radioisotopes are chemically attached to the surface of an NSP. In some embodiments, small molecule drugs are chemically attached to the surface or interior structure of an NSP. In some embodiments the charge of the interior or exterior of the NSP is modified with electrolytes to enhance the electrostatic interaction with the NSP and small molecule drugs. In some embodiments, siRNA, DNA, or drugs are mixed within the structure of the NSP.

NSPs described herein display a significant and surprising tumor tropism for primary tumors as well as to metastases derived from these tumors, even when metastases are distant from the primary tumor (e.g. brain, bone or lung metastases).

In some embodiments, it has been found surprisingly that an assembled NSP containing Papillomavirus L1 structural proteins but no Papillomavirus L2 structural proteins also displays universal tumor tropism. Accordingly, NSPs described herein that are derived from combinations of L1 structural proteins with therapeutics (but with no L2 protein) can also be used to target tumors.

In some embodiments, provided herein are methods and compositions for producing virion derived protein nanoparticles containing one or more therapeutic or diagnostic agents. The nanospheres particles of the present invention may be derived based on proteins found naturally in the Herpes Simplex Virus (HSV), the Respiratory Syncytial Virus (RSV), the Polyoma Virus, the beta papilloma virus ($\beta$-HPV), alpha-papilloma virus ($\alpha$-HPV), non-human Papillomavirus (Bovine Papillomaviurs, Macaque Papillomavirus, Cotton Rabbit Papillomavirus, Murine papillomavirus), Epstein Barr Virus, Parvovirus or the Rotavirus. In some embodiments, methods and compositions for encapsulating an agent within a NSP may require an initial isolation and purification of capsid proteins produced in a host cell system (e.g., yeast, mammalian cell, insect cell, *E. coli*) and subsequent reassembly in vitro. In some embodiments, methods and compositions for encapsulating an agent within a NSP may require an isolation and purification of capsid proteins produced in a cell free in vitro expression system such as *E. coli* lysate.

In some embodiments, methods for preparing an NSP to combine a therapeutic or diagnostic agent with papillomavirus proteins include: 1) total disruption and disassembly followed by loading of therapeutics and reassembly; 2) modifications to open pores with no disassembly followed by drug and closing of the pores; 3) chemical binding of radioisotopes to L1 amino acids; and/or 4) chemical binding of radioisotopes to L1 and L2 amino acids.

In some embodiments, provided herein are in vitro methods of encapsidating an agent within a virus-like nanosphere particle comprising: isolating viral capsid proteins directly from a host cell; incubating the capsid proteins with an agent in a reaction volume; and assembling the capsid proteins and agent to form a nanosphere particle, thereby encapsidating the agent within the nanosphere particle. In some embodiments, the capsid proteins comprise mutations that modify the serotype-specific immunogenicity in a subject.

In some embodiments, provided herein are intracellular methods of encapsidating a nucleic acid within a virus-like nanosphere particle comprising: providing a host cell that expresses a viral capsid protein; and incubating the host cell with a nucleic acid encoding a nucleic acid under conditions that promote intracellular nanosphere particle formation, thereby encapsidating the nucleic acid within the nanosphere particle intracellularly. In some embodiments, the capsid proteins comprise mutations or modifications that provide a modified serotype-specific immunogenicity in a subject that prevents cross-reactivity with pre-existing antibodies.

In some embodiments, provided herein are methods of isolating a viral capsid protein comprising: isolating nuclei or obtaining isolated nuclei from a preparation of host cells that express the viral capsid protein; sonicating the nuclei; and isolating the capsid proteins from the sonicated nuclei in the form of a monomer, capsomere or oligomer. In some embodiments, the methods of isolating a viral capsid protein comprise isolating the soluble fraction from the host cell where the monomer, capsomere or oligomer proteins are present. In some embodiments, the capsid proteins comprise mutations or modifications that provide a modified serotype-specific immunogenicity in a subject that prevents cross-reactivity with pre-existing antibodies.

In any one of the embodiments described herein, the viral capsid protein may be a papillomavirus capsid protein. In some embodiments, the papillomavirus capsid protein is L1. In some embodiments, the papillomavirus capsid protein is L2. In some embodiments, isolation of capsid proteins may include isolation of only L1 capsid proteins, only L2 capsid proteins, or a combination thereof. In some embodiments, the capsid protein is a new non-naturally found serotype derived from the human papillomavirus (HPV) serotype 16/serotype 31 L1 protein (HPV16/31 L1*) having mutations that reduces a subject's immunogenicity and antibody cross-reactivity to the protein.

In some embodiments, human papillomavirus capsid proteins are isolated from sonicated nuclei of host cells that express both L1 and L2 capsid proteins (wild-type and/or mutant). In some embodiments, the L1 and L2 capsid protein and/or capsomeres are obtained from the soluble fraction of the host cell (e.g. *E. coli*). In some embodiments, the L1 and L2 capsid proteins are independently expressed. That is, for example, L1 may be expressed by a first nucleic acid (e.g., plasmid DNA), while L2 may be expressed by a second nucleic acid, different from the first nucleic acid.

In some embodiments, an agent is a therapeutic agent or a diagnostic agent. In some embodiments, the agent is a nucleic acid, such as an expression modulatory nucleic acid (e.g., long non-coding RNA (lncRNA). In some embodiments the nucleic acid is a microRNA. In some embodiments the nucleic acid is a hybrid siRNA. In some embodiments the nucleic acid is an antisense oligonucleotide. In some embodiments, the nucleic acid is a small-interfering RNA (siRNA), short-hairpin RNA (shRNA), or a vector encoding an siRNA or shRNA. In certain other embodiments, the agent is a nucleic acid (e.g., DNA) encoding for a biologically active protein. In some embodiments, the agent is a small molecule (e.g. taxane, 5FU, Gemcitabine).

In some embodiments, provided herein are intracellular methods of encapsidating an agent within a human papillomavirus-derived nanosphere particle comprising: providing a host cell that expresses an L1 capsid protein encoding by a first nucleic acid and an L2 capsid protein encoded by a second nucleic acid different from the first nucleic acid; and incubating the host cell in the presence of an agent within the cell under conditions that promote intracellular nanosphere particle formation, thereby encapsidating the agent within the NSP intracellularly. In some embodiments, the L1 capsid protein comprises a mutation that reduces a subject's immune response and antibody cross-reactivity to the protein.

Any one of the embodiments described herein may further comprise purifying an assembled, loaded NSP.

In some embodiments, provided herein are methods of producing a virus-like nanosphere particle in a host cell comprising: expressing an L1 capsid protein from a first nucleic acid in a host cell; expressing L2 capsid protein from a second nucleic acid in the host cell, wherein the first nucleic acid is separate from the second nucleic acid; and isolating an assembled nanosphere particle from the host cell. In some embodiments, the ratio of L1 protein to L2 protein differs from a normal L1 protein to L2 protein ratio (e.g., different from ratio found in nature). In some embodiments, L1 capsid proteins are used without L2 capsid proteins.

In some embodiments, provided herein are methods for selectively delivering an agent to a tumor in a subject, the method comprising administering a tumor tropic nanosphere particle to a subject, wherein the tumor tropic nanosphere particle is associated with an agent, and is free of host cell and viral nucleic acid, and wherein the tumor tropic nanosphere particle comprises one or more viral capsid proteins without a heterologous targeting agent (e.g., without being associated with or attached to an antibody, peptide, ligands, receptor-binding moieties, or other targeting molecule that a capsid protein would otherwise naturally be associated of attached).

In some embodiments, provided herein are methods for preparing a nanosphere particle for selectively delivering a therapeutic or diagnostic agent to a cancer in a subject, the method comprising, obtain viral capsid proteins without any host or viral nucleic acid, and reassembling the capsid proteins in the presence of a therapeutic or diagnostic agent.

In some embodiments, provided herein are methods of producing human papillomavirus (PV) nanosphere particles loaded with an agent comprising: recombinantly expressing mutant PV L1 and wild-type PV L2 capsid proteins, or mutant PV L1 without any PV L2 capsid proteins in vitro in E. coli cells, wherein the mutant PV L1 capsid protein has mutations that differs from the wt HPV; isolating the L1 and L2 capsomeres, or L1 capsomeres; combining the capsid protein capsomeres with the agent and reassembly buffer containing salt and HEPES buffer, or salt and Histidine-HCl; and dialyzing the combination of protein and buffer to produce HPV nanosphere particles loaded with the agent.

In some embodiments, provided herein are methods for delivering and evaluating a cancer therapy comprising: identifying a subject with cancer; labeling tumor tropic nanosphere particles; loading the tumor tropic nanosphere particles with a therapeutic agent; administering a detectable amount of the nanosphere particles to the subject; and determining the presence or amount of the nanosphere particles in the subject during and after a period of a treatment.

In some embodiments, provided herein are compositions for the treatment or diagnosis of cancer cells, the composition comprising a therapeutic or diagnostic agent formulated with a nanosphere particle, wherein the nanosphere particle comprises structural proteins from HSV, RSV, Polyoma, PV, Epstein Barr or Rotavirus.

In some embodiments, provided herein are compositions for the treatment or diagnosis of cancer cells, the composition comprising a therapeutic or diagnostic agent formulated with a nanosphere particle, wherein the nanosphere particle comprises a mutated or modified PV L1 protein, wherein the mutation or modification reduces or modifies the PV serotype specific immunogenicity of the nanosphere particle.

These and other embodiments are described in more detail in the following detailed description and examples.

BRIEF DESCRIPTION OF THE DRAWINGS

FIG. 1 shows production of Pseudovirions (PsV) in 293TT cells

FIG. 2A shows capsomere particle production and purification method in *E. coli* and further loading and reassembly of Nanosphere Particles (NSPs) in vitro. FIG. 2B shows capsomere particle production and purification method in *E. coli*, in vitro reassembly into NSPs and further labeling with radioisotopes.

FIG. 3A shows western blot with L1 and L2 expression after isolation of soluble fraction from *E. coli*. FIG. 3B shows electron microscopic images displaying spontaneously reassembled particles after reducing agent (DTT) concentration was lowered and salt (sodium chloride) concentration was increased. L1/L2 capsomeres from *E. coli* homogenate were purified by affinity chromatography on a heparin column.

FIG. 4A shows NSPs production method in 293TT cell line. FIG. 4B shows NSPs production method in 293TT cell line and further labeling with radioisotopes.

FIGS. 5A-5B shows treatment of mice bearing a metastatic orthotopic ovarian tumor derived from SKOV-3 cells with NSPs and biodistribution comparison between tumor bearing and non-bearing animals. FIG. 5A shows results show in vivo bioluminescent signals as taken 48 hours after dosing. A single injection was administered with NSPs-luc (0.65 ml) when tumor size reached medium to large by palpitation on day 77 post tumor implantation.

FIG. 5B shows results of ex vivo tissue bioluminescent imaging of the primary tumor and tumors metastasized to the lung, the liver, the spleen GI-LN at 48 hours post dosing. Primary tumors and distant metastatic sites including lung, spleen, liver, mesenteric lymph nodes, femur and brain were dissected and imaged ex vivo for bioluminescence.

FIGS. 6A-6E show the treatment of mice bearing a metastatic orthotopic ovarian tumor derived from SKOV-3 cells with NSPs and PsV to compare the tumor tropism of the two types of particles. Graphs show a comparison between the biodistribution of NSPs and PSV particles delivering a luciferase reporter gene in an SKOV-3 ovarian orthotopic model. FIG. 6A shows a comparison of NSPs and PsV biodistribution found in the lungs in an ovarian orthotopic SKOV-3 model as determined by a luminescent reporter gene. FIG. 6B shows a comparison of NSPs and PsV biodistribution found in the liver in an ovarian orthotopic SKOV-3 model as determined by a luminescent reporter gene. Results show that both types of particles have a similar tropism both to the primary tumor (FIG. 6A) and to the distant metastases (FIG. 6E). This result demonstrate that NSPs containing mutant L1/L2 particles retain the tumor tropism observed with wild type PsV.

FIG. 7 shows plasmid pL1*L2 DNA sequence encoding mutant L1 (L1*) and L2 human codon-optimized (SEQ ID NO:1).

FIGS. 8A-8B show a HPVL1*-mutant DNA sequence (human codon optimized) (SEQ ID NO:2).

FIG. 9 shows HPVL1*-mutant DNA sequence (*E. coli* optimized) (SEQ ID NO:3).

FIG. 10 shows HPV6L2 DNA sequence (*E. coli* optimized) (SEQ ID NO:4).

DETAILED DESCRIPTION OF SOME EMBODIMENTS OF THE INVENTION

In some embodiments, aspects of the invention relate to methods and compositions for producing virion-derived protein nanosphere particles (NSPs) that contain therapeutic agents or diagnostic agents for delivery selectively to cancerous cells of a subject without eliciting a serotype-specific immune response in the subject. Surprisingly, human papillomavirus (HPV) variants that have reduced immunogenicity retain broad tumor tropism. Accordingly, in some embodiments, methods and compositions have been developed for effectively encapsidating a therapeutic or diagnostic agent within NSPs (e.g., papillomavirus-derived nanosphere particles) that can be used to deliver the agent selectively, in some instances without a targeting molecule, to cancerous cells of a subject (e.g., a human subject), without harming healthy, noncancerous cells.

A "nanosphere particle" herein refers to an organized capsid-like structure comprising self-assembling ordered arrays of one or more viral capsid proteins that do not include a viral genome. Nanosphere particles are morphologically and antigenically similar to authentic virions, but they lack viral genetic material (e.g., viral nucleic acid), rendering the nanosphere particle non-infectious. Nanosphere particles may be produced in vivo, in a suitable host cell, such as mammalian, yeast, bacterial, or insect host cell. Nanosphere particles may also be produced in vitro in a cell free expression system (e.g. *E. coli* lysate).

In some embodiments, nanospheres may be assembled from proteins found naturally in herpes simplex virus (HSV), Rous sarcoma virus (RSV), alpha-papilloma virus ($\alpha$-HPV), beta-papilloma virus ($\beta$-HPV), Non-Human Papillomavirus (Bovine Papillomavirus, Murine Papillomavirus, Cottontail Rabbit Papillomavirus, Macaque Papillomavirus), Epstein Barr virus, Hepatitis virus, Rotavirus, or other virus or virus-like particles. In some embodiments, a nanoparticle may be derived from the following: Adenoviridae, Papillomaviridae, Parvoviridae, Herpesviridae, Poxviridae, Hepadnaviridae, Polyomaviridae, Anelloviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, or Arteriviridae.

In some embodiments, other virus proteins which may be used as delivery agents within the scope of the present invention are not limited to but may include: retroviruses, adenoviruses, adeno-associated viruses, lentiviruses, poxivurses, baculoviruses, and bacteriophages. Other viruses that are not tumor tropic can be modified by adding a target molecule to its structure.

In some embodiments, nanospheres are prepared using a variant capsid protein having one or more mutations that modify the viral serotype-specific immunogenicity that prevent antibody cross-reactivity. In some embodiments, the term "serotype-specific immunogenicity" includes the ability of a serotype-specific viral antigen or epitope to elicit an immune response (humoral and/or cell-mediated) in a subject. A serotype refers to a distinct variation within a species of virus (e.g., human papillomavirus serotype 16 (HPV16) and 31 (HPV31) are different serotypes based on their cell-surface antigens)

Infection by one or more human papillomavirus high-risk serotypes (e.g. HPV16) is causally associated with cervical cancer (zur Hausen H., Cancer Res., 1989, 49, 4677-4681). Native virions of HPV are nonenveloped 50- to 60-nm-diameter icosahedral structures composed of 72 capsomeres, and each capsomere is composed of five L1 capsid proteins (Baker, T. S., et al., *Biophys J.,* 1991, 60, 1445-56; Trus, B. L., et al., *Nat Struct Biol.* 1997, 4, 413-20). Native virions of HPV also include L2 capsid proteins. A "capsid protein" refers to individual capsid proteins that assemble to form a viral capsid structure. A capsid protein can be in the form of a single protein monomer, or several capsid proteins can form an oligomer (e.g., pentamers, trimers). A "capsomere" refers to an oligomeric configuration of capsid protein. For example, capsomeres may comprise at least one L1 capsid protein (e.g., a pentamer of L1).

In some embodiments, capsid proteins are expressed intracellularly (in a host cell) in the presence of an agent to produce a nanosphere particle encapsidating the agent. A nanosphere particle encapsidating an agent is herein referred to as a "loaded" nanosphere particle. In some embodiments, a nucleic acid encoding a capsid protein (e.g., L1 or L2) is introduced into a host cell together with a nucleic acid encoding an agent, for example, a biologically active protein or peptide. In some embodiments, the nucleic acid encoding a capsid protein may encode more than one capsid protein, e.g., L1 and L2 capsid proteins. In some embodiments, two different capsid proteins are expressed intracellularly by introducing a first nucleic acid encoding a first capsid protein and a second nucleic acid encoding a second capsid protein such that each capsid protein is independently expressed by the cell. Expression of capsid protein in the presence of an agent results in intracellular formation (assembly) of nanosphere particles containing (encapsidating) the agent. Loaded nanosphere particles can be isolated directly from the host cell.

In some embodiments, one or more different capsid proteins are expressed intracellularly in the absence of an agent. In such embodiments, the assembled nanosphere particles are first isolated from the host cell, and then dissociated into individual capsid protein monomers and/or protein oligomers. These isolated capsid proteins may then be reassembled in the presence of an agent to produce a loaded nanosphere particle. Direct isolation of individual capsid proteins (rather than isolation of assembled NSPs) may, in some embodiments, reduce the risk of host cell contamination of the loaded nanosphere particle (e.g., with host cell nucleic acid, antigens, other exogenous material).

The terms "dissociated" and "disassembled" (used interchangeably) herein refers to the deconstruction of viral particles, capsids, or capsomeres into individual capsid proteins, for example, L1 and/or L2 capsid proteins. L1 and/or L2 capsomeres and/or capsid proteins that are isolated directly from cells can then be used in vitro to encapsidate a therapeutic or diagnostic agent, resulting in a "clean" preparation of L1 and/or L2 proteins, free of contaminating material (e.g., nucleic acid, antigens, or other material) from the host cell. The term "encapsidate" is also referred to herein as "loading" or "encapsulating," and refers to the process of surrounding an agent ("payload") with capsid proteins. The term "encapsulating" and "assembling" may also be used interchangeably herein when referring to a method of producing a nanosphere particle loaded with an agent. The term "assembling" refers to the process by which capsid proteins associate to form a capsomere, capsid, or nanosphere particle. The term "payload" and "agent" are used interchangeably and refer to any substance encapsidated within or attached to a nanosphere particle, for example, a therapeutic agent or a diagnostic agent.

In some embodiments, L1 and L2 capsid proteins are produced independently from independent nucleic acids (e.g., different vectors). In some embodiments, they can be produced in the same cell (e.g., using two different vectors within the same cell), or in a different cell (e.g., different host cells of the same type or different types of host cell). This approach allows the ratio of L1 and L2 proteins to be varied for either in vitro or intracellular assembly. The term "assembly" refers to the process by which capsid proteins come together to form a nanosphere particle. Independent production of L1 and L2 capsid proteins permits nanosphere particle assembly (e.g., in vitro or intracellularly) with varied ratios of L1 and L2, which may be advantageous during the delivery process. For example, a higher ratio of L2 to L1 in the assembled structure may result in a nanosphere particle having a higher nucleic acid binding affinity and more efficient intracellular delivery.

In some embodiments, L1 capsid proteins are isolated (e.g., from cells that express L1 alone, or from cells that express L1 and L2) and used independently of L2 capsid proteins. For example, L1 proteins may be assembled to form capsomeres or nanospheres that do not contain L2 proteins. In some embodiments, L1 proteins may be assembled (e.g., in vivo or in vitro) along with a payload to form a capsomere or nanosphere that encapsulates the payload (e.g., therapeutic or diagnostic agent). In some embodiments, an L1 capsid protein having one or more amino acid changes (e.g., a sequence alteration or a chemical amino acid modification such as a PEGylation or other modification) that reduce immunogenicity is used.

In some embodiments, nanospheres formed by L1 capsid proteins alone (with or without amino acid sequence modifications), for example HPV L1 capsid proteins, exhibit universal tropism as described herein and can be used for cell or tissue-specific delivery of one or more diagnostic or therapeutic agents.

In some embodiments, nanosphere particles or proteins are produced in insect cells, yeast, bacterial cells, or mammalian cells. In some embodiments, nanosphere particles or proteins are produced in cell-free expression systems.

In some embodiments, a nanosphere particle comprises a variant capsid protein having one or more mutations that reduce or modify HPV serotype specific immunogenicity. For example, a nanosphere particle may comprise a non-natural variant HPV-16 L1 protein having one or more mutations that prevents HPV 16 antibodies to cross-react with its structure.

In some embodiments, methods include delivering a therapeutic or diagnostic agent to a cancerous cell without delivering the agent to a non-cancerous cell, wherein the delivery vehicle is a nanosphere particle having reduced or modified serotype-specific immunogenicity. In some embodiments, methods include delivering a therapeutic agent to cancerous cells present at a single anatomical location or present at multiple, different anatomical locations, for example, cancerous cells (metastases) present in bone, lung and/or brain. In other embodiments, methods include inhibiting the proliferation of cancerous cells, without inhibiting proliferation of non-cancerous cells, wherein the cancerous cells are inhibited by delivery of an inhibitory agent, and wherein the delivery vehicle used to deliver the inhibitory agent to the cancerous cells is a nanosphere particle having reduced or modified serotype-specific immunogenicity. In still other embodiments, methods include detecting the presence of a cancerous cell at a single anatomical location or at multiple, different anatomical locations (e.g. metastases). In yet other embodiments, methods include monitoring the efficacy of a cancer therapy.

Variant Capsid Proteins Having Reduced or Modified Immunogenicity

In some embodiments, human papillomavirus (HPV) nanosphere particles comprise L1 capsid proteins, L2 capsid proteins, or both. The proteins may be wild-type or modified. In some embodiments, nanosphere particles comprise a naturally occurring HPV capsid protein and/or a variant HPV capsid protein having reduced or modified serotype-specific immunogenicity (e.g., in a subject). For example, in some instance, nanosphere particles comprises L1 and/or L2 proteins that have been modified (e.g., mutated, substituted, inserted, or deleted) to reduce immunogenicity against serotype-specific HPV antibodies. In some embodiments, nanosphere particles comprise L1 and/or L2 variant sequences that are not recognized by existing antibodies against HPV (e.g., HPV16L1), which may be present in subjects who have an HPV infection or who have received an HPV vaccine. Examples of variant capsid proteins are described in WO 2010/120266, incorporated herein by reference in its entirety. A capsid protein may have an amino acid variation that results in reduction or avoidance of neutralization by the immune system of the subject. In some embodiments, a nanosphere particle contains a recombinant capsid protein (e.g., a recombinant HPV L1 and/or L2 protein) having an amino acid variation that results in altered protein immunogenicity in a subject. In some instances, a nanosphere particle having such reduced or modified immunogenicity may also retain its capability of packaging (loading) and delivering molecules/agents to a subject.

In some embodiments, an amino acid of a capsid protein is modified to enhance the positive charge of the nanosphere particle interior. In some embodiments, modifications are introduced to permit a stronger electrostatic interaction of nucleic acid molecules with an amino acid that faces the interior of the nanosphere particle, or to promote retention of the nucleic acid within the nanosphere particle (e.g., avoid leakage of nucleic acid molecules out of the nanosphere particle). As referenced above, examples of such modifications are described in WO 2010/120266. Any "modified" nanosphere particle (that is, any nanosphere particle containing a modified capsid protein) may be loaded with an agent for selective delivery to a diseased/cancerous cell, sparing normal cells.

In some embodiments, HPV L1 and/or L2 capsid proteins may be chemically modified such that the resulting protein comprises linkers that enable the binding of small molecules to its internal structure or to its external structure. In some embodiments, HPV L1 and/or L2 proteins may be fused to other molecules (e.g., lipids, polymers) that contain hydrophobic drugs (e.g., taxanes), which may provide additional functionality. In some embodiments, HPV L1 and/or L2 proteins may be fused to other proteins, which may provide tissue specific tropism. Examples of such modifications are described, for example, in U.S. Pat. No. 6,991,795, incorporated herein by reference in its entirety. These other proteins may be viral or non-viral and may, in some embodiments, be host-specific or cell type-specific. Nanosphere particles may comprise a recombinant protein or fragment thereof (e.g., an HPV capsid and/or surface protein or fragment thereof). In some embodiments, nanosphere particles may be based on naturally-occurring particles that are processed to incorporate an agent as described herein. In some embodiments, one or more sequence variants may be used as described herein.

According to some aspects of the invention, nanosphere particles described herein exhibit tropism for specific cell types. In some embodiments, cancer cells and cancer metastases are targeted naturally by the particles without requiring any additional targeting agents. In some embodiments, cancer stem cells are targeted. Accordingly, nanosphere particles described herein can be administered to a subject without a targeting agent and the nanospheres will preferentially accumulate in tissues that contain tumor cells, tumor metastases, cancer stem cells, or a combination thereof. Accordingly, nanosphere particles described herein can be used to preferentially deliver therapeutic and/or diagnostic agents to these specific cells sparing other types of cells. In some embodiments, the tumors are non-mucosal (e.g., in non-mucosal tissue(s)). In some embodiments, the tumors are solid tumors.

According to aspects of the invention, nanosphere particles that contain modified capsid proteins (for example to reduce the immunogenicity of the capsid proteins, for example by altering the immunogenicity of the L1 capsid protein) also can retain tumor tropism properties that are useful for targeted delivery. These particles also have the benefit of evading detection by the host immune system, thereby increasing the amount or efficiency of targeting and delivery to the target cells of interest. According to aspects of the invention, nanosphere particles that contain L1 capsid proteins (for example modified L1 capsid proteins), but not L2 capsid proteins also can retain tissue tropism properties that are useful for targeted delivery.

However, it should be appreciated that other combinations of HPV proteins (e.g., capsid proteins) or peptides may be used herein. In some embodiments, one or more targeting agents (e.g., a targeting peptide fused to a capsid protein) may be used to enhance or alter the tissue tropism of the particles described herein.

In some embodiments, nanospheres that include capsid proteins with one or more amino acid alterations in a hypervariable or surface exposed loop retain the property of cell-specific or disease-specific targeting. These variant nanospheres can be used for targeted delivery according to aspects of the invention without using any other targeting agents. Examples of conformation-dependent type-specific epitopes that can be modified to alter immunogenicity are found on the surface of HPV nanosphere particles within hyper-variable loops, where the amino acid sequence is highly divergent between HPV serotypes. These loops are designated BC, DE, EF, FG and HI. Many neutralizing antibodies are generated against epitopes in these variable loops and are type-specific, with limited cross-reactivity, cross-neutralization and cross-protection. Different HPV serotypes induce antibodies directed to different type-specific epitopes and/or to different loops. In some embodiments, HPV L1 and/or L2 may be mutated at an amino acid position located in a hyper-variable, surface-exposed loop. The mutation may be made at an amino acid position within a loop that is not conserved between HPV serotypes. This position may be completely non-conserved (any amino acid may be at this position), or the position can be conserved.

Independent Expression Vectors

In some embodiments, an expression vector is used to express an HPV capsid protein, a variant HPV capsid protein, or a combination thereof. For example, in some embodiments, a mutant HPV16L1 protein having reduced immunogenicity (referred to herein as "L1*") is co-expressed with L2 in a host cell system (e.g., Sf9 or 293TT cells). In some embodiments, each protein is expressed by an independent vector (e.g., L1* is expressed by vector A, while L2 is expressed by vector B).

In some embodiments, L1 and L2 proteins are expressed in a host cell system from independent expression vectors (e.g., plasmids) as opposed to both being expressed from the same vector. The expression of L1 and L2 proteins from independent plasmids permits the relative levels of L1 and L2 comprised within a nanosphere particle to be optimized for particular applications. This control of L1 to L2 protein ratio also permits optimization of molecular structure for delivery of particular agents. In some embodiments, a variety of nanosphere particle structures can be produced to conform to the need of the different classes of agents (e.g., DNA, RNA, small molecule, and large molecule), both in terms of electrostatic charge and other functions (e.g., DNA binding domains, nanosphere particle inner volume, and/or endosomal release function). For example, nanosphere particles with a higher content of L2 protein will be better to bind nucleic acids (L2 contains a DNA binding domain), whereas nanosphere particles with a smaller content of L2 protein will be better for other small molecules. Nanospheres with different ratios of L1:L2 protein will have different interior volumes, which will permit a higher concentration of drug to be encapsidated. In some embodiments, the release of agent into the cell may also be modulated. In some embodiments, structures containing more L2 protein may have an increased ability to transfer nucleic acids intracellularly. Different ratios of L1:L2 may be used in any of the embodiments described herein. In some embodiments, a nanosphere contains L1 protein, but not L2 protein.

In some embodiments, each separate expression nucleic acid encodes an L1 protein (but not an L2 protein) or an L2 protein (but not an L1 protein) sequence operably linked to a promoter. In some embodiments, other suitable regulatory sequences also may be present. The separate expression nucleic acids may use the same or different promoters and/or other regulatory sequences and/or replication origins, and/or selectable markers. In some embodiments, the separate nucleic acids may be vectors (e.g., plasmids, or other independently replicating nucleic acids). In some embodiments, separate nucleic acids may be independently integrated into the genome of a host cell (e.g., a first nucleic acid integrated and a second nucleic acid on a vector, or two different nucleic acids integrated at different positions). In some embodiments, the relative expression levels of L1 and L2 proteins may be different in different cells, differ using different expression sequences, be independently regulated, or a combination thereof.

Host Cell Expression Systems

In some embodiments, a capsid protein (e.g., L1 and/or L2) is expressed in a host cell system. In some embodiments, more than one type of protein (e.g., L1 and L2) are expressed in a host cell system. In some embodiments, L1 and L2 are expressed in the same host cell (or system). In some embodiments, L1 and L2, or variations thereof, are expressed in different host cells (or systems). Any one of the proteins or nanoparticles described herein may be produced in an insect cell system, a yeast cell system, a bacterial cell system, a mammalian cell system, plant cell system or in a cell free expression system. Examples of host cell systems to be used herein include, but are not limited to, *Spodoptera frugiperda* (sf) cells, *Escherichia coli* cells, and 293T or 293TT mammalian cells. In particular embodiments, L1 and/or L2 and/or variants thereof are expressed intracellularly, where they may form capsomeric (e.g., oligomeric) structures during cellular growth (e.g., fermentation). Subsequent to structure formation, in some embodiments, the capsid proteins and/or structures may be isolated from host cell nuclei or from the host soluble fraction. Any suitable method may be used to isolate the nuclei, for example, sonication, or other isolation method. After isolation, capsid proteins and/or structures may be purified by any suitable means, for example, column chromatography, or other purification method. In some embodiments, rather than isolating the capsid proteins from cell nuclei, the proteins are permitted to assemble intracellularly in the presence of a payload to form loaded nanoparticles.

Directly isolating capsid proteins from nuclei of cells (rather than isolating assembled nanoparticles) provides several benefits. For example, in some embodiments, there is a reduced risk of encapsidating and transferring genetic information (e.g., DNA, RNA) from the host cell to a subject receiving the loaded nanoparticle. In some embodiments, isolated capsid proteins are assembled in a cell-free system with payload to produce a nanoparticle loaded with that payload (e.g. DNA coding for a biologically active protein, small molecule, RNA). In certain embodiments, de novo assembly of nanoparticles as described herein (as opposed to using pre-formed nanoparticles) results in a larger percentage of loaded nanoparticles.

In some embodiments, a capsid protein may be expressed recombinantly in any one of the host cell systems described herein.

Non-limiting examples of insect cell systems: in some embodiments, any one of the capsid proteins described herein may be expressed in *Spodoptera frugiperda* (Sf) cells, for example, Sf21 cells. In some embodiments, baculoviruses are used to express a gene encoding a capsid protein, for example, a gene encoding L1 and/or L2 and/or a variant thereof (including recombinant versions). In some embodiments, the capsid protein is an L1 or L2 protein from a designated serotype of human papillomavirus, for example, HPV16, HPV18, HPV31, HPV33, HPV34, HPV35, HPV52, HPV58, HPV73, and HPV91, and/or as described (Touze et al., *FEMS Microbiol. Lett.*, 2000, 189, 121-7; Touze et al., *J. Clin. Microbiol.*, 1998, 36, 2046-51; and Combita et al., *FEMS Microbiol. Lett.* 2001, 204(1), 183-88). In some embodiments, a gene encoding a capsid protein is cloned into a plasmid, such as pFastBac1 (Invitrogen). In some embodiments, insect cells may be maintained in Grace's insect medium (Invitrogen), or other suitable medium, supplemented with, for example, 10% fetal calf serum (FCS, Invitrogen), infected with recombinant baculoviruses, and incubated at 37° C. In some embodiments, cells may be harvest three days post infection, and the nanoparticle purified. In some embodiments, cells may be re-suspended in phosphate-buffered saline (PBS) containing Nonidet P40 (0.5%), pepstatin A, and leupeptin (1 µg/ml each, Sigma Aldrich), and incubated for 30 min at 4° C. Nuclear lysates may be formed into pellets by centrifugation, re-suspended in ice-cold PBS containing pepstatin A and leupeptin, and then sonicated. Samples may then be loaded on a cesium-chloride (CsCl) gradient and centrifuged to equilibrium (e.g., 22 h, 27,000 rpm in a SW28 rotor, 4° C.). Cesium-chloride gradient fractions may be investigated for density by refractometry and for the presence of L1/L2 protein by electrophoresis in 10% sodium dodecyl sulfate-polyacrylamide gel (SDS-PAGE) and Coomassie blue staining. Positive fractions may be pooled, diluted in PBS and pelleted (e.g., in a Beckman SW 28 rotor (3 h, 28,000 rpm, 4° C.)). After centrifugation, nanoparticles may be re-suspended in 0.15 mol/L NaCl and sonicated, for example, by one 5-second burst at 60% maximum power. Total protein content may be determined. Other techniques may be used, as embodiments of the invention are not limited by these examples.

Non-limiting examples of yeast cell systems: in some embodiments, any one of the capsid proteins described herein may be expressed in yeast cells. In some embodiments, capsid proteins may be expressed using a galactose-inducible *Saccharomyces cerevisiae* expression system. For example, leucine-free selective culture medium may be used for the propagation of yeast cultures, and yeast may be induced with medium containing glucose and galactose. Cells may be harvested using any filtration means. After resuspension, in some embodiments, cells may be treated with Benzonase and mechanically disrupted (e.g., using a homogenizer). Cell lysate may then be clarified using any filtration means. An exemplary protocol can be found in Cook et al. Protein Expression and Purification, 1999, 17, 477-84. Other techniques may be used, as embodiments of the invention are not limited by these examples.

Non-limiting examples of mammalian cell system: in some embodiments, any one of the capsid proteins described herein may be expressed in mammalian cell systems. Buck et al. (J. Virol. 2004, 78, 751-757) reported the production of papilloma virus-like particles and cell differentiation-independent encapsidation of genes into bovine papillomavirus (BPV) L1 and L2 capsid proteins expressed in transiently transfected 293TT human embryonic kidney cells, which stably express SV40 large T antigen to enhance replication of SV40 origin-containing plasmids. Pyeon et al. reported a transient transfection method that achieved the successful and efficient packaging of full-length HPV genomes into HPV16 capsids to generate virus particles (*PNAS*, 2005, 102, 9311-16). Transiently transfected cells (e.g., 293 cells, for example 293T or 293TT cells) may be lysed by adding Brij58 or similar nonionic polyoxyethylene surfactant detergent, followed by benzonase and exonuclease V, and incubating at 37° C. for 24 h to remove unpackaged cellular and viral DNA and to allow nanoparticle maturation. The lysate may then be incubated on ice with 5 M NaCl (to a final concentration of 0.8M NaCl) and clarified by centrifugation, or other clearing means. Nanoparticles may be collected by high-speed centrifugation, or other collection means. Other techniques may be used, as embodiments of the invention are not limited by these examples.

Non-limiting examples of bacterial cell system: in some embodiments, any one of the capsid proteins described herein may be expressed in *Escherichia coli* (*E. coli*) cells. In *E. coli*, in some embodiments, a potential contaminant of protein is endotoxin, a lipopolysaccharide (LPS) that is a major component of the outer membrane of Gram-negative bacteria (Schädlich, et al. *Vaccine*, 2009, 27, 1511-22). In some embodiments, transformed BL21 bacteria may be grown in lysogeny broth (LB) medium containing, for example, 1 mM ampicillin and incubated with shaking at 200 rpm at 37° C. In some embodiments, at an optical density (OD600) of 0.3-0.5 nm, bacteria may be cooled, and Isopropyl β-D-1-thiogalactopyranoside (IPTG) may be added to induce protein expression. In some embodiments, after 16-18 hours, bacteria may be harvested by centrifugation, or other harvesting means. Bacteria may be lysed by homogenizing, lysates may be cleared, capsid proteins purified, and LPS contamination removed using, for example, chromatographic methods, such as affinity chromatography or size exclusion chromatography, or other purification methods. Lipopolysaccharide contamination may also be removed using, for example, 1% Triton X-114. Other techniques may be used, as embodiments of the invention are not limited by these examples.

With reference now to FIG. 1A, a particle production method for nanospheres with will now be discussed. Prepare plasmid DNA expressing the capsid proteins of HPV16 L1 and L2 together or on separate vectors 121 and transform into bacteria 123. Over 24 hours the L1 and L2 proteins will be produced in the cell and will assemble into capsomeres 125. Next, harvest, lyse, nuclease digest; purifying using sucrose gradient and Heparin column 127 (or size-exclusion chromatography, ion exchange chromatography, di-filtration, or affinity chromatography). Collect purified capsomeres 129. Reassemble purified particles with "payload" 131. A "payload" may include at least one or a combination of the following: DNA, siRNA, micro RNA, antisense oligonucleotide, small molecule drug, dye or radioisotope. Column purify to remove free payload 133.

With reference now to FIG. 2B, a particle production method for nanospheres will now be discussed. A recombinant DNA molecule containing a sequence encoding a papillomavirus L1 protein or a papillomavirus L2 protein or a combination of L1 and L2 proteins is manufactured 221 and then transfected into a 293TT cell line 223. Preferably, the NSP may express papillomavirus L1 protein or L2 protein or a combination of L1 and L2 proteins in the host cell. Over 48 hours the L1 and L2 proteins will be produced in the cell and will assemble into capsomeres and then fully assembled VLPs 225. Next, harvest, lyse, nuclease digest; purifying using sucrose gradient and Heparin column 227 (or size-exclusion chromatography, ion exchange chromatography, di-filtration, or affinity chromatography). Collect purified empty virus-like particles 229. Disassembly into capsomeres 231. Reassemble purified particles with "payload" 233. A "payload" may include at least one or a combination of the following: DNA, siRNA, drug, dye or radioisotope. Column purify to remove free payload 235.

With reference now to FIG. 3A, a particle production method for radio labeled nanospheres will now be discussed. Prepare plasmid DNA expressing the capsid proteins of HPV16 L1 and L2 together or on separate vectors 321 and transform into bacteria 323. Over 24 hours the L1 and L2 proteins will be expressed in the cell and will assemble into capsomeres 325. Next, harvest, lyse, nuclease digest; purify using sucrose gradient and Heparin column 327 or size-exclusion chromatography, ion exchange chromatography, di-filtration, or affinity chromatography. Collect purified capsomeres 329. Reassemble into empty nanosphere particles 331. Label particles with radioactive isotope 333. Column purify to remove free isotopes and enrich for radiolabeled nanosphere particles 335.

With reference now to FIG. 3B, a particle production method for nanospheres will now be discussed. A plasmid expressing the capsid proteins of HPV-L1 and L2 421 and transfect into a 293TT cell line 423. Over 48 hours the L1 and L2 proteins will be produced in the cell and will self-assemble into empty virus-like particles 425. Next, harvest, detergent lyse, nuclease digest, and gradient purify and Heparin column 427 (or size-exclusion chromatography, ion exchange chromatography, di-filtration, or affinity chromatography). Collect purified empty virus-like particles 429. Label particles with radioactive isotope 431. Column purify to remove free isotopes and enrich for radiolabeled nanosphere particles 433.

A single potency curve on the basis of internalized immunotoxin has shown a sharp reduction in viability once cells internalized >5×106 molecules (Pirie et al. (2011) The Journal Of Biological Chemistry, Vol. 286, No. 6, pp 4165-4172). Accordingly, according to one aspect of the present invention, the production of the immunotoxins to a level of fifty percent cytotoxicity is a function of the time for proliferating tumor cell to uptake plasmid DNA, replicate, transcribe and translate and produce enough immunotoxin to reach levels of at least 50% cytotoxicity as a function of time.

Loading with Therapeutic Agents and/or Diagnostic Agents

Some embodiments described herein relate to methods for producing nanosphere particles having (encapsidating) a medical, a therapeutic, or a diagnostic agent, or a combination thereof.

In some embodiments, a nanosphere particle loaded with an agent may be delivered to a diseased cell/tissue (e.g., cancerous cell). In some embodiments, a tissue may have pre-malignant disease (e.g., cervical dysplasia, bronchopulmonary dysplasia, prostate intraepithelial neoplasia). In some embodiments the pre-malignant diseased tissue may be infected with a virus, such as HPV or HSV. In some embodiments, nanosphere particles may be used to deliver therapeutic agents to treat pre-malignant disease or condition, and/or may be used to deliver diagnostic agents to diagnose pre-malignant diseases or conditions. For example, fluorophores, quantum dots, metals, radioisotopes and/or other imaging agents may be loaded into nanosphere particles and delivered to the pre-malignant cells of a subject. In some embodiments, agents may be used to track early stage diseases (e.g., early stage lung cancer, early stage prostate cancer). Any suitable therapeutic, diagnostic and/or other medical agent may be loaded into the nanosphere particle according to the methods described herein and subsequently delivered to a subject. Examples of methods for the administration of nanosphere particles to subjects are described for example in U.S. Pat. No. 7,205,126, incorporated herein by reference in its entirety.

After isolation of L1 and L2 capsid proteins which may be in the form of monomers or oligomers (e.g., pentamers), nanosphere particles may be assembled and loaded, as described herein.

Loading of a nanosphere particle with an agent utilizing a 'disassembly/reassembly' method has been described, for example, in U.S. Pat. No. 6,416,945 and International Publication No. WO 2010/120266, each incorporated herein by reference. Any one of the previously described loading methods or methods described herein may be used to encapsidate a therapeutic agent, for example a gene encoding a therapeutic protein, or a diagnostic agent. However, it should be appreciated that any suitable method may be used as aspects of the invention are not limited in this respect.

In some embodiments, a loading method comprises incubating a nanosphere particle in a buffer of ethylene glycol tetraacetic acid (EGTA) and dithiothreitol (DTT). Under this condition, a nanosphere particle completely disaggregated into monomeric and/or olgomeric capsid protein structures. A diagnostic or therapeutic agent as described herein may then be combined with the disaggregated capsid protein structures, and then diluted in a buffer of dimethyl sulfoxide (DMSO) and calcium chloride (CaCl2) with or without zinc chloride (ZnCl2) in order to reassemble the capsid proteins into a nanosphere particle, thereby encapsidating the agent. In some embodiments, the presence of ZnCl2 increases the reassembly of capsid proteins into a nanosphere particle. Other salts useful in aiding disassembly/reassembly of viral capsid proteins into nanosphere particles are those that include, for example, zinc (Zn), copper (Cu), nickel (Ni), ruthenium (Ru), and iron (Fe). Other salts may also be used in the embodiments described herein.

In some embodiments, loading of a nanosphere particle does not require an initial nanosphere particle disassembly step.

In some embodiments, the efficacy of nanosphere particle loading and delivery to a cell may depend, at least in part, on the particular ratio of (a) capsid protein to reaction volume, (b) therapeutic or diagnostic agent (e.g., therapeutic protein) to capsid protein, (c) therapeutic or diagnostic agent to reaction volume, or other ratio of components. A nanosphere particle loaded with an agent, using a method described herein, in some embodiments, effectively delivers the agent to at least 65%, at least 70%, at least 75%, at least 80%, at least 85%, at least 90%, at least 95%, 96%, 97%, 98%, 99%, or 99.9% of target cells (for example, when measured in a cell-based assay).

In some embodiments, a nanosphere particle may be loaded with an agent using a method comprising: (a) contacting a preparation of capsid proteins with the agent in a reaction volume, wherein (i) the ratio of capsid protein to reaction volume may range from 0.01 µg capsid protein per 1 µl reaction volume to 0.1 µg capsid protein per 1 µl reaction volume, or from 0.1 µg capsid protein per 1 µl reaction volume to 1 µg capsid protein per 1 µl reaction volume; (ii) the ratio of agent to capsid protein may range from 0.01 µg agent per 1 µg capsid protein to 0.1 µg agent per 1 µg capsid protein, or from 0.1 µg agent per 1 µg capsid protein to 10 µg agent per 1 µg capsid protein, and/or (iii) the ratio of agent to reaction volume may range from 0.001 µg agent per 1 µl reaction volume to 1 µg agent per 1 µl reaction volume, or from 0.01 µg agent per 1 µl reaction volume to 10 µg agent per 1 µl reaction volume; and (b) reassembling the capsid proteins to form a nanosphere particle, thereby encapsidating the agent within the nanosphere particle. In some embodiments, the ratio of capsid protein to reaction volume ranges from 0.2 µg capsid protein per 1 µl reaction volume to 0.6 µg capsid protein per 1 µl reaction volume; the ratio of nucleic acid to capsid protein ranges from 0.5 μg agent per 1 μg capsid protein to 3.5 μg agent per 1 μg capsid protein; and the ratio of agent to reaction volume ranges from 0.2 μg agent per 1 μl reaction volume to 3 μg agent per 1 μl reaction volume.

In some embodiments, dissociating a nanosphere particle or capsid protein oligomers can be performed in a solution comprising ethylenediaminetetraacetic acid (EDTA) and/or ethylene glycol tetraacetic acid (EGTA) and dithiothreitol (DTT), wherein the concentration of EDTA and/or EGTA ranges from 0.3 mM to 30 mM and the concentration of DTT ranges from 2 mM to 200 mM. In certain embodiments, the concentration of EDTA and/or EGTA ranges from 1 mM to 5 mM. In certain embodiments, the concentration of DTT ranges from 5 mM to 50 mM. Other reagents, volumes, and concentrations may be used, as embodiments of the invention are not limited by these examples.

The step of reassembling capsid proteins into a nanosphere particle may be carried out in a solution comprising dimethyl sulfoxide (DMSO), CaCl2 and ZnCl2, wherein the concentration of DMSO ranges from 0.03% to 3% volume/volume, the concentration of CaCl2 ranges from 0.2 mM to 20 mM, and the concentration of ZnCl2 ranges from 0.5 μM to 50 μM. In some embodiments, the concentration of DMSO ranges from 0.1% to 1% volume/volume. In some embodiments, the concentration of ZnCl2 ranges from 1 μM to 20 μM. In some embodiments, the concentration of CaCl2 ranges from 1 mM to 10 mM.

In some embodiments, the loading method is further modified to stabilize the nanosphere particle, in that the loading reaction is dialyzed against hypertonic NaCl solution (e.g., using a NaCl concentration of about 500 mM) instead of phosphate-buffered saline (PBS), as was previously described. Surprisingly, this reduces the tendency of the loaded nanosphere particle to form larger agglomerates and precipitate. In some embodiments, the concentration of NaCl ranges between 5 mM and 5 M. In some embodiments, the concentration of NaCl ranges between 20 mM and 1 M.

In some embodiments, the methods described herein may be used to encapsulate nucleic acids, for example, RNA interference (RNAi) nucleic acids. In some embodiments, short interfering RNA (siRNA), a short hairpin RNA (shRNA), microRNA, long non coding RNA (lncRNA), hybrid DNA-RNA or an antisense nucleic acid (DNA or RNA) is transfected into host cells (e.g., 293 cells or other mammalian or insect host cells) during the production of the nanosphere particles. Accordingly, loaded nanosphere particles may be produced intracellularly to later provide efficient gene silencing effects when delivered to a cell of a subject. In some embodiments, a plasmid is used to express the nucleic acid molecule. In some embodiments, the plasmid may be ~2 kilobases (kb) to ~6 kb in size, or larger. In some embodiments, smaller plasmids may be used. In some embodiments, a nanosphere particle encapsidates a plasmid that is designed to be expressed (and ultimately functional) within a target cell, for example, a cancerous cell of a subject to which the nanosphere particle is selectively delivered. Consequently, the silencing nucleic acid encoded by the plasmid will be active within the target cell, resulting in knockdown of the targeted gene.

In some embodiments, the therapeutic agent is an inducer of RNA interference or other inducer of gene silencing. An inducer of RNA interference may be a siRNA, a shRNA, a hybrid nucleic acid molecule comprising a first part that comprises a duplex ribonucleic acid (RNA) molecule and a second part that comprises a single stranded deoxyribonucleic acid (DNA) molecule, a longer double-stranded RNA or a DNA construct for expression of siRNA or longer RNA sequences. Other inducers or modulators of gene expression include inducers of DNA methylation, or ribozymes, or aptamers. In other embodiments, the therapeutic agent can be a modulator of gene expression such as a PNA (Peptide Nucleic Acid).

RNA interference (RNAi) is a process whereby the introduction of double-stranded RNA (dsRNA) into a cell inhibits gene expression post-transcriptionally, in a sequence dependent fashion. RNAi can be mediated by short (for example 19-25 nucleotides) dsRNAs or small interfering RNAs (siRNA). Double-stranded RNA is cleaved in the cell to create siRNAs that are incorporated into an RNA-induced silencing complex (RISC), guiding the complex to a homologous endogenous mRNA, cleaving the mRNA transcript, and resulting in the destruction of the mRNA.

To induce RNA interference in a cell, dsRNA may be introduced into the cell as an isolated nucleic acid fragment or via a transgene, plasmid, or virus. In some embodiments, nanosphere particles are used to deliver dsRNA to the target cells.

In some embodiments, a short hairpin RNA molecule (shRNA) is expressed in the cell. A shRNA comprises short inverted repeats separated by a small loop sequence. One inverted repeat is complimentary to the gene target. The shRNA is then processed into an siRNA which degrades the target gene mRNA. shRNAs can be produced within a cell with a DNA construct encoding the shRNA sequence under control of a RNA polymerase III promoter, such as the human H1, U6 or 7SK promoter. Alternatively, the shRNA may be synthesized exogenously and introduced directly into the cell, for example through nanosphere particle delivery. In some embodiments, the shRNA sequence is between 40 and 100 bases in length or between 40 and 70 bases in length. The stem of the hairpin are, for example, between 19 and 30 base pairs in length. The stem may contain G-U pairings to stabilize the hairpin structure.

Short-interfering RNA (siRNA) sequences are selected on the basis of their homology to the target gene. Homology between two nucleotide sequences may be determined using a variety of programs including the BLAST program (Altschul et al. J. Mol. Biol., 1990, 215, 403-10), or BestFit (Genetics Computer Group, 575 Science Drive, Madison, Wis., USA, Wisconsin 53711). Sequence comparisons may be made using FASTA and FASTP (see Pearson & Lipman, 1988. Methods in Enzymology 183: 63-98). Tools for design and quality of siRNAs, shRNAs and/or miRNAs are known in the art. Web-based online software system for designing siRNA sequences and scrambled siRNA sequences are for example siDirect, siSearch, SEQ2SVM, Deqor, siRNA Wizard (InvivoGen). The specificity can be predicted using for example SpecificityServer, miRacle. Target sequences can be researched for example at HuSiDa (Human siRNA Database), and siRNAdb (a database of siRNA sequences). Sequence comparison may be made over the full length of the relevant sequence, or may more preferably be over a contiguous sequence of about or 10, 15, 20, 25 or 30 bases. In some embodiments, the degree of homology between the siRNA and the target gene is at least 75%, at least 80%, at least 85%, at least 90%, at least 95%, at least 97%, or at least 99%, or 100%. The siRNA may be between 10 bp and 30 bp in length, or between 20 bp and 25 bp, or the siRNA is 20, 21 or 22 bp in length.

Short-interfering RNA molecules may be synthesized using standard solid or solution phase synthesis techniques which are known in the art.

In some embodiments, the siRNA has an overhang at one or both ends of one or more deoxythymidine bases to increase the stability of the siRNA within cells by reducing its susceptibility to degradation by nucleases.

In some embodiments, the siRNA is a hybrid nucleic acid molecule comprising a first part that comprises a duplex ribonucleic acid (RNA) molecule and a second part that comprises a single stranded deoxyribonucleic acid (DNA) molecule. Targets for the RNA interference would include disease causing genes e.g. oncogenes, inflammatory genes, regulatory genes, metabolic genes, viral genes. In one embodiments of the invention the target genes would be E6, E7, p53, Sirt-1, survivin, EGFR, VEGFR, VEGF, CTNNB1 or other oncogenes.

Linkages between nucleotides may be phosphodiester bonds or alternatives, for example, linking groups of the formula P (O) S, (thioate); P (S) S, (dithioate); P (O) NR'2; P (O) R'; P (O) OR6; CO; or CONR'2 wherein R is H (or a salt) or alkyl (1-12C) and R6 is alkyl (1-9C) is joined to adjacent nucleotides through —O— or —S—.

Modified nucleotide bases can be used in addition to the naturally occurring bases. For example, modified bases may increase the stability of the siRNA molecule, thereby reducing the amount required for silencing. The term modified nucleotide base encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5'position. Thus modified nucleotides may also include 2'substituted sugars such as 2'-0-methyl-; 2-0-alkyl; 2-0-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4, N4-ethanocytosine, 8-hydroxy-N6-methyladenine, 4-acetylcytosine, 5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5methoxyuracil, 2 methyl-thio-N6-isopentenyladenine, uracil-5-oxyacetic acid methyl ester, psueouracil, 2-thiocytosine, 5-methyl-2 thiouracil, 2-thiouracil, 4-thiouracil, 5methyluracil, N-uracil-5-oxyacetic acid methylester, uracil 5-oxyacetic acid, queosine, 2-thiocytosine, 5-propyluracil, 5-propylcytosine, 5-ethyluracil, 5ethylcytosine, 5-butyluracil, 5-pentyluracil, 5-pentylcytosine, and 2,6, diaminopurine, methylpsuedouracil, 1-methylguanine, 1-methylcytosine.

In some embodiments, siRNA molecules or longer dsRNA molecules may be made recombinantly by transcription of a nucleic acid sequence, for example contained within a vector as described herein. The vector may be any RNA or DNA vector.

In some embodiments, the vector can be an expression vector, wherein the nucleotide sequence is operably linked to a promoter compatible with the cell. Promoters suitable for use in various vertebrate systems are well known in the art. For example, suitable promoters include viral promoters such as mammalian retrovirus or DNA virus promoters, e.g., MLV, CMV, RSV, SV40 IEP (immediate early promoter) and adenovirus promoters and metallothionein promoter. Strong mammalian promoters may also be used. It will be appreciated that variants of such promoters retaining substantially similar transcriptional activities may also be used.

In some embodiments, the vector may have at least two promoters, one to direct expression of the sense strand and one to direct expression of the antisense strand of the dsRNA. In other embodiments, two vectors may be used, one for the sense strand and one for the antisense strand. Alternatively the vector may encode RNAs which form stem-loop structures which are subsequently cleaved by the cell to produce dsRNA.

The nucleic acid construct may contain a specific cellular, viral or other promoter or repressor of gene expression. The promoter or repressor may be designed to reflect the context of the cell into which the construct is introduced. For example, the construct may contain a viral promoter so expression from the construct is dependent upon the presence of a viral protein, so that the construct is expressed only in viral-infected cells. Similarly, the construct may have a promoter or repressor specific to certain cell types or to certain developmental stages. For example, where the vector is for use in virally infected cell such as cells infected with HPV, a viral promoter which matches the disease-causing virus should be used, e.g., a HPV promoter (such as the promoter causing expression of HPV E6/E7) for HPV-infected cells. In such embodiments, the vector will only be expressed in the virally-infected cells.

Nucleic acids are highly charged and do not cross cell membranes by free diffusion. The hydrophilic character and anionic backbone of nucleic acids such as, for example, siRNAs reduces their uptake by the cells. In some embodiments, nucleic acids (e.g., siRNA) may be loaded into nanosphere particle (e.g., HPV-nanosphere particle) to efficiently deliver them to a subject through administration of nanosphere particle. In some embodiments, encapsulating the nucleic acid into a nanosphere particle increases cellular uptake, allows traversal of biological membrane barriers in vivo, and/or increases the bioavailability of the nucleic acid (e.g., siRNA).

In some embodiments, the agent loaded into the nanosphere particle is an anti-viral agent. In some embodiments, the agent is an anticancer agent. In some embodiments, the anticancer agent is a taxane and/or a platinum (e.g., cisplatinum, carboplatinum, oxaliplatinum).

In some embodiments, the methods described herein may be used to encapsidate radioisotopes or radionuclides. In some embodiments, NSPs encapsidating such radioisotopes or radionuclides may be used to treat cancerous cells. Examples of radioisotopes that may be used with the methods described herein include, but are not limited to, lutetium-177 (prepared from ytterbium-176, which is irradiated to become Yb-177, which decays rapidly to Lu-177), yttrium-90, iodine-131, phosphorus-32, boron-10, actinium-225, ismuth-213, lead-212, bismuth-212, polonium-212, thallium-208, Pb-208.

In some embodiments, the methods described herein may be used to encapsidate small molecules or large molecules such as, for example, biologics, oncolytic viral proteins, or a toxic agent, inducers of DNA methylation, recombinant DNA, ribosomes, aptamers, modulators of gene expression, proteins, antibodies, siRNA or antisense molecules, biological therapies, viral gene cassettes such as the myc-gene, viral proteins such as the P30 retrovirus protein, or oncolytic viral proteins. Other small or large molecules may be encapsidated. In some embodiments, two or more therapeutic agents may be encapsidated.

In some embodiments, radioisotopes are useful to treat cancer by killing cancer cells (for example by inducing apoptosis). In some embodiments, compositions and methods of the invention can be used for selectively targeting radioisotopes to cancer cells. Nanospheres described herein can be loaded with one or more radioisotopes and administered systemically to a subject (for example a subject having one or more indicia of cancer). Due to the tropism of the nanosphere the radioisotope(s) will be delivered selectively to the cancer cells, and will be taken up and directed to the cell nuclei, where the effect of apoptosis will be maximized.

In some embodiments, the therapeutic agent that may be loaded into a nanosphere particle using the methods described herein is a chemotherapeutic agent, for instance, methotrexate, vincristine, adriamycin, cisplatin, carboplatin, oxaliplatin, non-sugar containing chloroethylnitrosoureas, 5-fluorouracil, mitomycin C, bleomycin, doxorubicin, dacarbazine, paclitaxel, docetaxel, fragyline, Meglamine GLA, valrubicin, carmustaine and poliferposan, MMI270, BAY 12-9566, RAS famesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, Alimta/Pemetrexed, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) or Vindesine sulfate, but it is not so limited.

In some embodiments, the therapeutic agent that may be loaded into a nanosphere particle using the methods described herein is an immunotherapeutic agent, for instance, Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab or ImmuRAIT-CEA, but it is not so limited.

In some embodiments, the therapeutic agent that may be loaded into a nanosphere particle using the methods described herein is an antiviral agent. Examples of anti-viral agents are: Polysulfates (PVAS), Polysulfonates (PVS), Polycarboxylates, Polyoxometalates, Chicoric acid, zintevir, cosalane derivatives, Bicyclams (i.e., AMD3100), T-22, T-134, ALX-40-4C, CGP-64222, TAK-779, AZT (azidothymidine), ddI, ddC, d4T (didehydrodideoxythymidine), 3TC (3'-thiadideoxycytidine), ABC, and other ddN (2',3'-dideoxynucleoside) analogs, Nevirapine, delavirdine, efavirenz, emivirine (MKC-442), capravirine, thiocarboxanilide UC-781, acyclovir, valaciclovir, penciclovir, famciclovir, bromovinyldeoxyuridine (BVDU, brivudin), Cidofovir, Adefovir dipivoxil, Tenofovir disoproxil, Ribavirin, valacyclovir, gancyclovir, formivirsen, foscarnet, EICAR (5-ethynyl-1-β-D-ribofuranosylimidazole-4-carboxamide), Mycophenolic acid, Neplanocin A, 3-deazaneplanocin A, 6'-C-methylneplanocin A, DHCeA (9-(trans-2',trans-3'-dihydroxycyclopent-4'-enyl)adenine), or c3DHCeA (9-(trans-2',trans-3'-dihydroxycyclopent-4'-enyl)-3-deazaadenine), as described, for example, in De Clercq, J. Pharmacol. Exp. Ther., 2001, 297, 1-10, incorporated by reference herein, but it is not so limited.

In some embodiments, a diagnostic agent may be loaded into a nanosphere using methods described herein. A diagnostic agent may be a detectable moiety (e.g., a radioisotope, a fluorescent marker, a radio-opaque moiety, or other detectable moiety) or a molecule attached to a detectable moiety (e.g., a molecule attached to a radioisotope, referred to herein as a radiolabeled molecule). In some embodiments, a diagnostic agent may be a labeled antibody, for example an antibody that binds specifically to a disease antigen (for example a cancer antigen). In some embodiments, a diagnostic agent may be a labeled receptor binding molecule, a labeled ligand or other labeled binding molecule. In some embodiments, a diagnostic agent may be a labeled enzyme or an enzyme substrate. In some embodiments, a diagnostic agent may be a label nucleic acid, protein, lipid, carbohydrate or other molecule.

In some embodiments, one or more therapeutic or diagnostic agents are encapsulated within a nanosphere. However, in some embodiments, one or more therapeutic or diagnostic agents may be attached to the surface of a nanosphere (for example using a covalent linkage, reversible linkage or an electrolyte solution). In some embodiments, a nanosphere may include both one or more encapsulated and one or more surface bound agents.

Universal Tumor Tropism

In some embodiments, nanosphere particles of the present invention exhibit universal tumor tropism. Tropism refers to the specificity of a pathogen (e.g., virus) for a host tissue and is a natural phenomenon. Typically, pathogens confer tropism for a particular tissue or cell type, for example, human immunodeficiency virus confers tropism for particular macrophage cells and T cells, while recombinant adeno-associated virus confers tropism for respiratory epithelial cells (Flotte, et al. Am. J. Respir. Cell Mol. Biol., 1992, 7, 349-356). Virion-derived nanosphere particles described herein can confer tropism for more than one, and in some instances many, different types of cancer cells. The term "universal tropism" refers to the nanosphere particle's specificity for multiple types of cancer cells, for example, breast, ovarian, lung, and bone cancer cells. Other examples of primary tumors that may be targeted or treated using the nanospheres described herein include, but are not limited to, prostate tumors, colon tumors, colo-rectal tumors, ovarian tumors, head and neck tumors, liver tumors, pancreatic tumors, renal, and brain tumors. In some embodiments, the tumor is a solid tumor. In some embodiments the tumor is a hematopoietic tumor. In some embodiments, the tumor is a primary tumor. In some embodiments, the tumor has metastasized and the nanoparticles can detect the distant metastases. In some embodiments the nanoparticles may detect the cancer stem cells within the primary tumor and the metastases.

As used herein, the term "tumor" refers to a tissue comprising transformed cells that grow uncontrollably. A tumor may be benign (benign tumor) or malignant (malignant tumor or cancer). Tumors include leukemias, lymphomas, myelomas, plasmacytomas, and the like; and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, rhabdomyosarcoma, myosarcoma, colon carcinoma, pancreatic cancer, breast cancer, ovarian cancer, prostate cancer, squamous cell carcinoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medullablastoma, craniopharyngioma, ependymoma, pinealoma, hemangioblastoma, acoustic neuroma, ogliodendroglioma, meningioma, melanoma, neuroblastoma, neuroglioma, and retinoblastoma.

In some embodiments, the cancer tropism of the nanospheres described herein can be used to target therapeutic agents to cancer tissue without requiring specific targeting agents. In some embodiments, the cancer tropism of the nanospheres described herein can be used to target diagnostic agents to cancer tissue without requiring cancer specific targeting agents.

In some embodiments, nanosphere particles are delivered to particular organs or tissues (e.g., lung) or cells or sub-cellular locations. However, in some embodiments, nanosphere particles described herein can be administered systemically and their natural tropism results in their selective accumulation in cancer tissue.

Accordingly, in some embodiments, a therapeutically effective dose of a nanosphere is one that is sufficient to result in a therapeutic level of the agent being delivered to the target tissue of interest (e.g., the cancerous tissue). In some embodiments, the amount of agent that is delivered can be evaluated using one or more detectable agents (e.g., a detectable therapeutic agent, for example labeled with a detectable moiety, or a detectable diagnostic agent) to determine the efficiency of delivery to the target tissue. In some embodiments, the nanosphere is administered to a subject in an amount effective to treat a disease or condition.

In some embodiments, the term "therapeutically effective amount" or "amount effective" in the context of a NSP or a NSP composition for administration to a subject refers to an amount of the NSP or composition that ameliorates or treats the disease or condition.

Amounts effective will depend, in some embodiments, on the subject being treated; the severity of a condition, disease or disorder; the subject's parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. In some embodiments, maximum dose, that is, the highest safe dose may be used according to sound medical judgment. It will be understood by those of ordinary skill in the art, however, that a subject may insist upon a lower dose or tolerable dose for medical reasons, psychological reasons or for virtually any other reasons.

In some embodiments, the term "treat," "treating," or "therapeutic," do not necessarily mean total cure or abolition of the disease or condition. In some embodiments, any alleviation of any undesired signs or symptoms of a disease or condition, to any extent, can be considered treatment or therapy. In some embodiments, treatment may include acts that may worsen the patient's overall feeling of well-being or appearance.

In some embodiments, the nanospheres are administered intravenously, intramuscular, subdermally, orally, nasally or topically. Other modes of administration may be used.

In some embodiments, provided herein are methods for selectively delivering an agent to a tumor in a subject, the method comprising administering a tumor tropic nanosphere particle to a subject, wherein the tumor tropic nanosphere particle is associated with an agent, and is free of host cell and viral nucleic acid, and wherein the tumor tropic nanosphere particle comprises one or more viral capsid proteins without a heterologous targeting agent. In some embodiments, the agent is a therapeutic agent. In some embodiments, the therapeutic agent is an inorganic molecule, an organic molecule, or a biologic active molecule. In some embodiments, the therapeutic agent includes a small molecule, a protein, a peptide, an antibody, a toxin, a nucleic acid, a radioisotope, a metal, an inducer of DNA methylation, a modulator of gene expression, an immune modulator, an enzyme inhibitor, a kinase inhibitor, an apoptosis inducer, a metabolism inhibitor, or any combination thereof. In some embodiments, the nucleic acid is an siRNA molecule, an shRNA molecule, a microRNA, a long non coding RNA, a hybrid DNA-RNA, a DNA molecule, an antisense molecule, a viral gene cassette, or any combination thereof. In some embodiments, the therapeutic agent is a radioisotope or a radiolabeled molecule. In some embodiments, the agent is a diagnostic agent. In some embodiments, the diagnostic agent is an imaging or contrast agent. In some embodiments, the diagnostic agent is labeled with a detectable label. In some embodiments, the detectable label is a fluorescent or radioactive label.

In some embodiments, the agent is encapsulated with the nanosphere particle. In some embodiments, the agent is mixed with the viral capsid proteins in the nanosphere particle. In some embodiments, the agent is chemically linked to an amino acid of one or more capsid proteins in the nanosphere particle.

In some embodiments, the nanosphere particle is assembled from one or more viral capsid proteins or capsomeres that are isolated and purified from a host cell expression system. In some embodiments, two different viral capsid protein types are expressed from different nucleic acid constructs in the host cell expression system. In some embodiments, the one or more viral capsid proteins and capsomeres are reassembled in vitro to form virus like particles. In some embodiments, the host cell expression system is bacterial, yeast, insect, plant or mammalian host cell expression system. In some embodiments, the host cell expression system is E. coli. In some embodiments, the nanosphere particle is assembled from one or more viral capsid proteins isolated from a cell free expression system.

In some embodiments, the nanosphere particle comprises one or more capsid proteins from Herpes Simplex Virus, Polyomavirus, Papilloma Virus, Epstein Barr Virus, Rous Sarcoma Virus or Rotavirus. In some embodiments, the nanosphere particle comprises one or more Papilloma Virus capsid proteins.

In some embodiments, the nanosphere particle comprises one or more capsid proteins having an amino acid sequence alteration that modifies the immunogenicity of the capsid protein relative to a naturally-occurring capsid protein in the subject. In some embodiments, the capsid protein is a PV capsid protein having mutations that reduce or modify an PV serotype-specific immunogenicity in the subject. In some embodiments, the PV capsid protein is an L1 and/or L2 capsid protein. In some embodiments, the nanosphere particle comprises a PV L1 capsid protein without any L2 capsid protein. In some embodiments, at least one viral capsid protein is modified to prevent an immunogenicity response in the host. In some embodiments, the modification is a PEGylation.

In some embodiments, the subject has cancer, the agent is an anti-cancer agent, and the nanosphere particle is administered in an amount sufficient to deliver a therapeutically effective dose of the agent to the cancer. In some embodiments, the cancer is a solid-tumor with or without metastases and with or without cancer stem cells. In some embodiments, the disease is a pre-malignant tumor. In some embodiments, the agent is a diagnostic agent and the subject is being screened for one or more indicia of cancer. In some embodiments, the cancer is selected from the group consisting of leukemias, lymphomas, myelomas, plasmacytomas, sarcomas, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, rhabdomyosarcoma, myosarcoma, colon carcinoma, pancreatic cancer, breast cancer, ovarian cancer, prostate cancer, squamous cell carcinoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medullablastoma, craniopharyngioma, ependymoma, pinealoma, hemangioblastoma, acoustic neuroma, ogliodendroglioma, meningioma, melanoma, neuroblastoma, neuroglioma, and retinoblastoma.

In some embodiments, the cancer is present at two or more separate locations in the subject.

In some embodiments, provided herein are methods for preparing a nanosphere particle for selectively delivering a therapeutic or diagnostic agent to a cancer in a subject, the method comprising, obtain viral capsid proteins without any host or viral nucleic acid, and reassembling the capsid proteins in the presence of a therapeutic or diagnostic agent. In some embodiments, the capsomere is obtained from a host cell expression system and purified. In some embodiments, the capsid proteins are from a tumor tropic virus. In some embodiments, the tumor tropic virus is PV. In some embodiments, the capsid protein contains an amino acid sequence alteration or amino acid modification that changes the immunogenicity of the nanosphere particle in the subject.

In some embodiments, PV L1 and L2 capsid proteins are used. In some embodiments, PV L1 capsid protein is used, but no L2 capsid protein is used.

In some embodiments, provided herein are methods of producing human papillomavirus (PV) nanosphere particles loaded with an agent comprising: recombinantly expressing mutant PV L1 and wild-type PV L2 capsid proteins, or mutant PV L1 without any PV L2 capsid proteins in vitro in *E. coli* cells, wherein the mutant PV L1 capsid protein has mutations that differs from the wt HPV; isolating the L1 and L2 capsomeres, or L1 capsomeres; combining the capsid protein capsomeres with the agent and reassembly buffer containing salt and HEPES buffer, or salt and Histidine-HCl; and dialyzing the combination of protein and buffer to produce HPV nanosphere particles loaded with the agent. In some embodiments, the reassembly buffer contains 0.5M NaCl, 5 mM CaCl2, and 40 mM HEPES (pH 6.8), or (2) 0.5M NaCl, 5 mM CaCl2, and 40 mM Histidine-HCl (pH 5.2).

In some embodiments, provided herein are methods of delivering and evaluating a cancer therapy comprising: a) identifying a subject with cancer; b) labeling tumor tropic nanosphere particles; c) loading the tumor tropic nanosphere particles with a therapeutic agent; d) administering a detectable amount of the nanosphere particles to the subject; and e) determining the presence or amount of the nanosphere particles in the subject during and after a period of a treatment. In some embodiments, the label is selected from the group consisting of fluorescent, radioactive, and chemiluminescent. In some embodiments, the nanosphere particle comprises a variant PV-L1 protein having a mutation(s) that makes it immunogenically different from the wt HPV-16 serotype.

Provided herein are compositions for the treatment or diagnosis of cancer cells, the composition comprising a therapeutic or diagnostic agent formulated with a nanosphere particle, wherein the nanosphere particle comprises structural proteins from HSV, RSV, Polyoma, PV, Epstein Barr or Rotavirus.

Also provided herein are compositions for the treatment or diagnosis of cancer cells, the composition comprising a therapeutic or diagnostic agent formulated with a nanosphere particle, wherein the nanosphere particle comprises a mutated or modified PV L1 protein, wherein the mutation or modification reduces or modifies the PV serotype specific immunogenicity of the nanosphere particle. In some embodiments, the mutation or modification reduces or modifies HPV-16 serotype specific immunogenicity.

EXAMPLES

Example 1

Production of Mutant L1* and L2 Capsid Proteins in E. coli Cell System (FIG. 2A)

Purification of VLPs by sucrose gradient centrifugation

Make a stock solution of 65% sucrose by dissolving 32.5 g of crystalline sucrose (Fisher cat. #57-50-1) to a final volume of 50 ml sample buffer. Sample buffer used for VLP purification is 0.5M NaCl (American Bioanalytical cat. # AB01915) in sterile 1×PBS (Boston BioProducts cat. # BM 220S).

Make different concentrations of sucrose solution as described in Table 1 by mixing appropriate volumes of 65% sucrose stock solution (Step 1) in sample buffer.

TABLE 1

| Final sucrose % | ml 65% stock | ml buffer |
| --- | --- | --- |
| 50 | 7.69 | 2.31 |
| 40 | 6.15 | 3.85 |
| 30 | 4.62 | 5.38 |
| 20 | 3.08 | 6.92 |
| 10 | 1.54 | 8.46 |

Gently overlay decreasing concentrations of sucrose (highest concentration at the bottom) in a Beckman Polyallomer centrifuge tube (Cat. #326819). The volumes of different sucrose concentrations in the tube are as follows:

| 65% | 0.5 ml |
| --- | --- |
| 50% | 0.5 ml |
| 40% | 0.75 ml |
| 30% | 0.75 ml |
| 20% | 0.75 ml |
| 10% | 0.75 ml-1 ml |

Keep the gradient undisturbed at room temperature for 45 min. Gently load clarified lysate supernatant on top of the sucrose gradient without disturbing the layers below.

Centrifuge the tubes at 45,000 rpm at 4° C. for 2 hrs in a SW55Ti rotor (Beckman Coulter, Inc.).

Gently remove the tubes from the rotor and collect 0.2 ml fractions from bottom of the centrifuge tube. Analyze fractions by SDS-PAGE and BCA assay for total protein.

Purification of NSPs Using Heparin HiTrap Column

After first centrifugation, if the homogenate is still turbid—re-centrifuged at 15,000 g for 30 min.

Recover clarified homogenate and store at −80° C. until use.

Add 0.01% Tween 80 to clarified homogenate.

Dialyze into PBS supplemented to 0.25 M NaCl, 2 mM DTT, 0.01% Tween 80, pH 7.4—overnight at 4° C. with three changes of buffer.

Equilibrate 1-mL HiTrap Heparin HP with 10 column volumes (CV) of dialysis buffer.

Load entire volume of dialyzed homogenate onto Heparin column at ~0.1 mL/min.

After loading, chase sample with ~2 CV of dialysis buffer.

Elute column with step gradient of increasing NaCl concentration—all steps contain PBS plus 1 mM DTT, 0.01% Tween 80-2.5 CV of each step: 0.4, 0.6, 0.8, 1.0 & 1.5 M NaCl.

Collect 1.0 mL fractions of flow-through from loading and 0.5-mL fractions during elution.

Determined absorbance of fractions at 260, 280 & 340 nm.

Analyze load flow-through and NaCl gradient elution fractions by reducing SDS-PAGE on Bio-Rad TGX Any kD gels—stained with Coomassie R-250.

Purification of NSPs by Size-Exclusion Chromatography

Preparation of an agarose gel filtration column.

De-gas the DPBS-BSA solution by exposure to vacuum.

Clamp the column to a ring stand. Put the bottom cap on and add 5 ml of DPBS/0.5 M NaCl.

Remove the bottom cap to eject any bubbles. Recap and add more DPBS/0.5 M NaCl. Fill to near the top of the column.

Float a frit on the surface. Gently tap the frit to dislodge any air bubbles. Tap frit down to the bottom of the column using a 1- or 5-ml pipet (or the serum separator).

Remove the bottom cap and drain out most of the fluid.

Suspend the agarose beads by gently swirling and inverting the bottle. Pour bead slurry into the column. Fill the column to the rim.

Remove the bottom cap. Partially exchange the beads into room-temperature DPBS-BSA by repeatedly allowing the column to drip to near dryness then pouring on more DPBS-BSA.

Replace the bottom cap. Cover the top of the column with Parafilm. Suspend beads by repeated gentle inversion of the column. Return the column to the clamp and allow blocking and settling overnight at room temperature.

Remove Parafilm. Float a frit on the fluid surface and gently tap down to within a few mm of the bed surface.

Remove the cap from the bottom of the column. Wash the column with at least 10 column volumes of DPBS/0.5 M NaCl.

Optional: If capsids are being purified out of crude cell lysate add 1 μl of Benzonase nuclease and incubate 10 to 30 min at 37° C. to digest any residual unencapsidated DNA.

Add 0.5 ml or less (i.e., less than 1/10 of the agarose bed volume) of clarified lysate (or capsids in Optiprep) to the washed agarose gel filtration column.

Apply 0.25 ml of DPBS/0.5 M NaCl to the top of the column. Collect column eluate in a siliconized 1.5-ml tube. Repeat this for a total of 12 0.25-ml fractions.

Screen fractions for encapsidated DNA and protein.

Regenerate columns for re-use by washing the column with 10 column volumes of DPBS/0.5 M NaCl, then exchanging into DPBS-BSA supplemented with 0.05% (w/v) NaN3 or other preservative. Store the column at room temperature for several days.

Figure 3A:
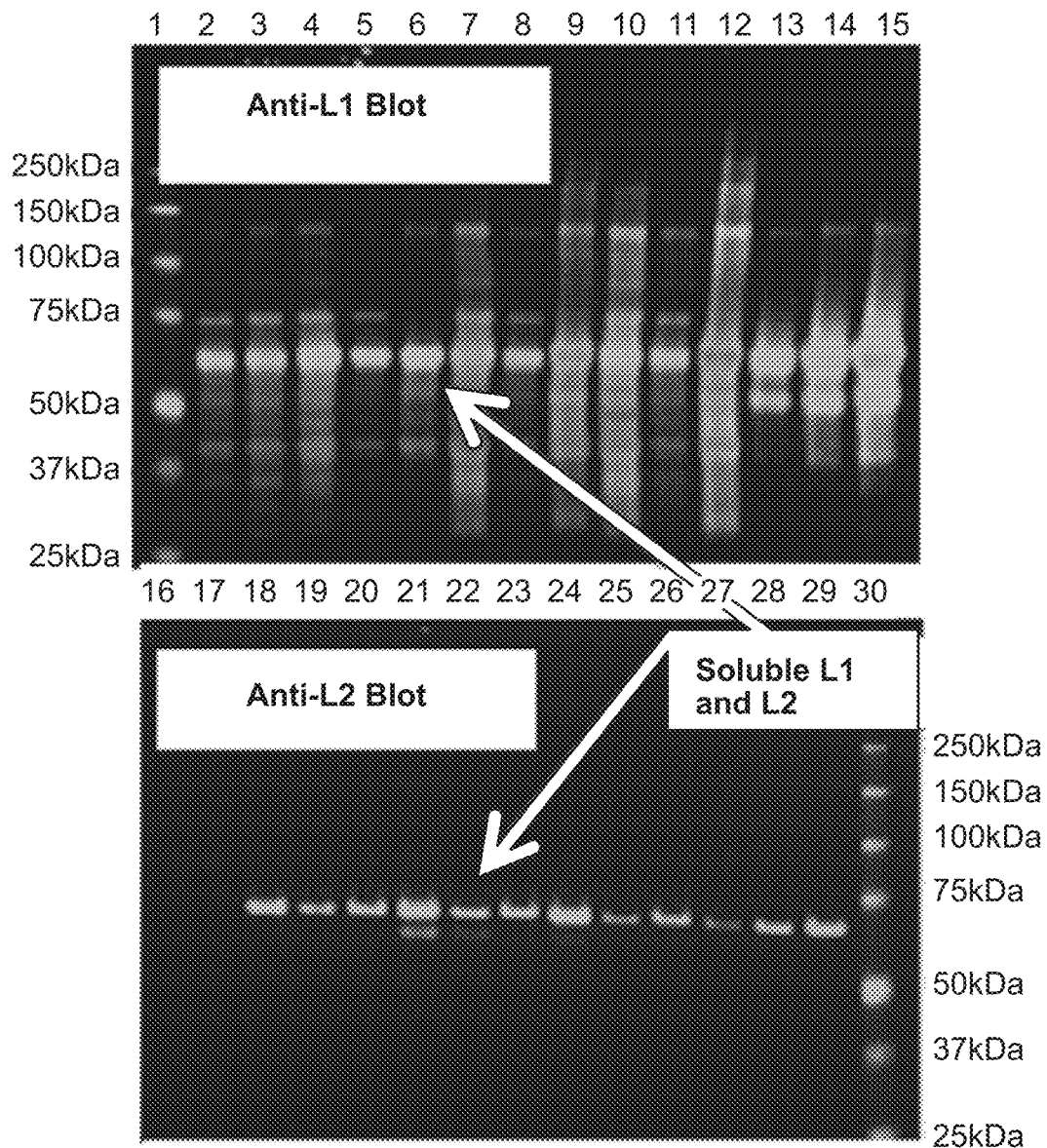
Figure 3B:
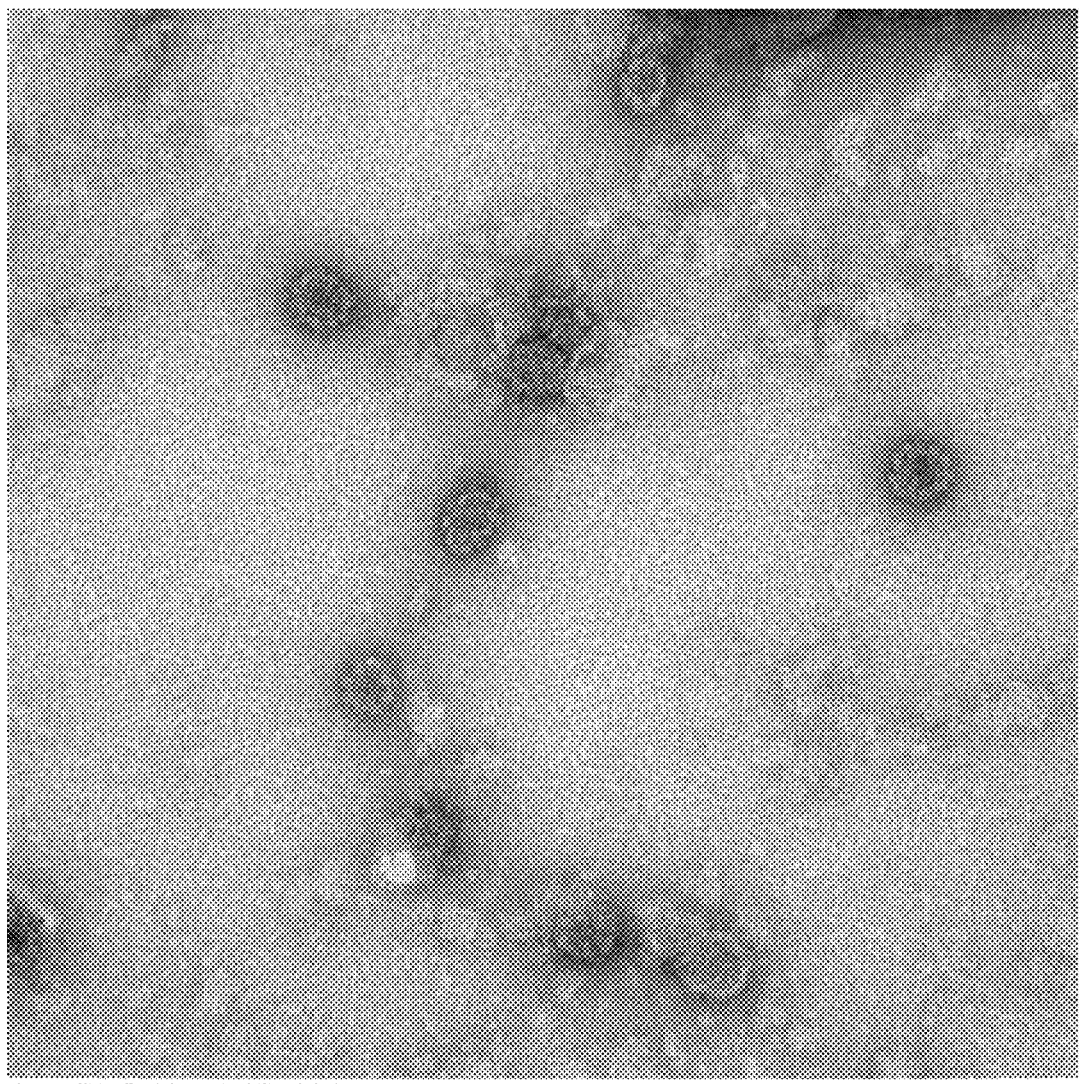

After column purification samples were analyzed by Electron Microscopy showing assembled particles (FIG. 3B).

Example 2

Figure 4A:
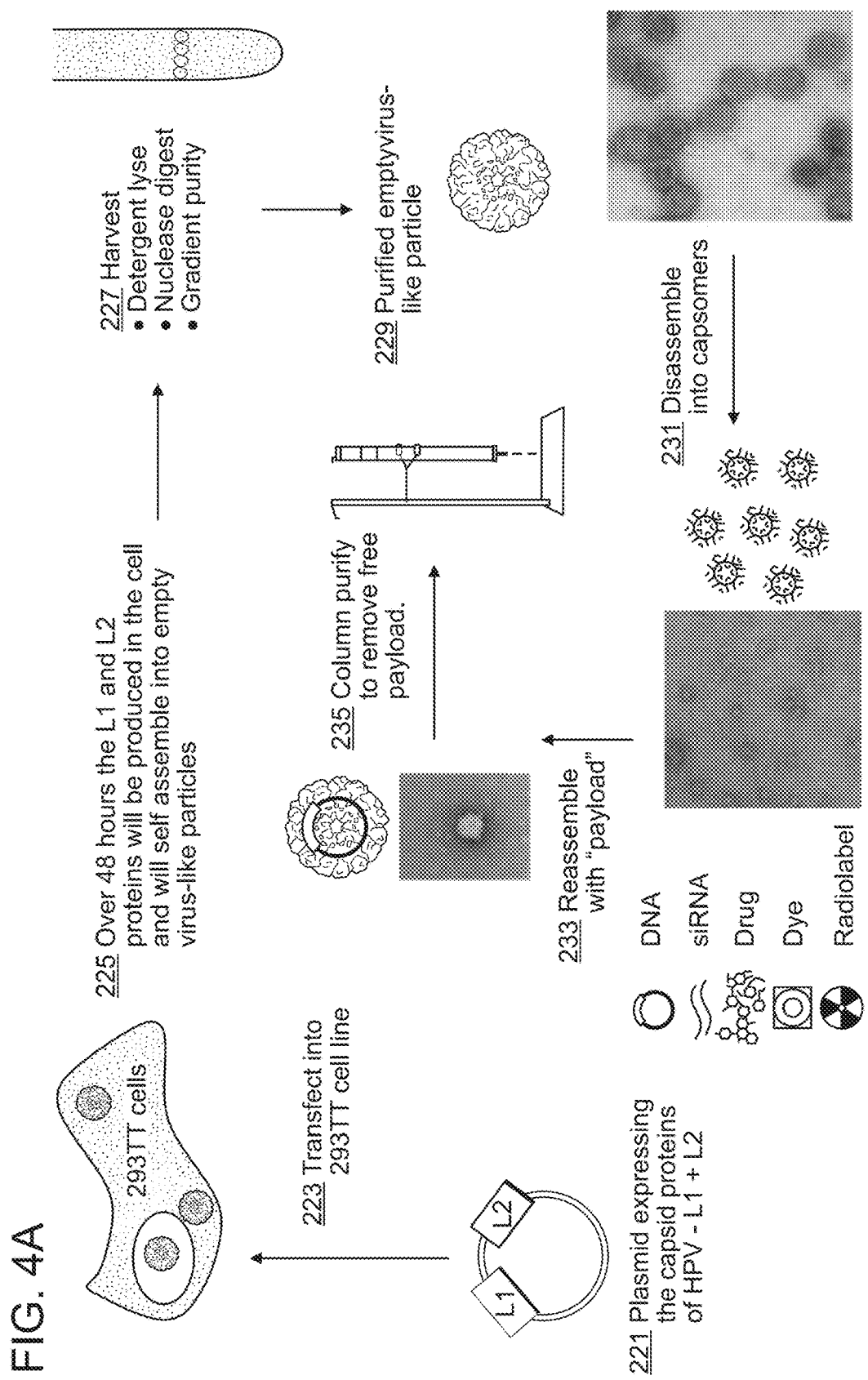

Production of Mutant L1* and L2 Capsid Proteins in Mammalian Cell System (FIGS. 4A & B)

Plasmids containing human-optimized codon sequences were used to produce HPV16/31L1 mutant (L1*) and a HPV16L2 capsid proteins using a mammalian cell culture system, as follows.

HPV L1/L2 nanosphere particles and L1 only nanosphere particles were added to disassembly buffer (0.5 M NaCl, 10 mM DTT (Dithiothreitol), 20 mM EDTA (Ethylenediaminetetraacetic acid), 50 mM Tris-HCl (pH 8.0)) to reach a final concentration of 0.05 mg/ml. The solution was incubated overnight at 37° C.

The HPV nanosphere particles were then concentrated to between 0.1-0.2 mg/ml using 100 kD spin columns. DNA or siRNA was added at a ratio of 1 µg of nucleic acid for every 5 µg of nanosphere particle. The resultant mixture was dialyzed using 100 kD cut-off dialysis tubing against one of two reassembly buffers: (1) 0.5M NaCl, 5 mM CaCl2, 40 mM HEPES (pH 6.8); or (2) 0.5M NaCl, 5 mM CaCl2, 40 mM Histidine-HCl (pH 5.2). The reassembly buffer was changed three times overnight (~12-16 hours) during the dialysis.

To remove free (unencapsidated) DNA, the reassembled nanosphere particles were treated with Benzonase endonuclease (1 U/µg of input DNA) for 10 minutes at room temperature. The Benzonase endonuclease was removed by one of three ways: (1) chemical inactivation using 0.5 M NaCl+80 mM EDTA for 1 hour at room temperature; (2) column removal using a 100 kD spin column to remove the endonuclease and replace the volume with an appropriate reassembly buffer; or (3) purification over an Optiprep (Iodixanol) gradient, following methods described (Buck and Thompson, Current Protocols in Cell Biology, December 2007, 26.1.1-26.1.19).

Removal of free DNA was achieved in one of two ways: (1) column removal using a 100 kD spin column to remove the free DNA and replace the volume with appropriate reassembly buffer; or (2) purification over an Iodixanol gradient, following methods described (Buck and Thompson (2007)).

Quantitation of encapsidated or nanosphere particle-associated nucleic acid was achieved by: (1) digesting the particles in buffer containing 0.01 U Proteinase K, 0.25% SDS, and 25 mM EDTA to liberate the nucleic acid from the protein (Buck and Thompson (2007)); (2) running DNA samples on a 1% agarose gel (TAE buffer+GelRed dye), or running siRNA samples on a 3% agarose gel (TAE Buffer+GelRed dye) with a molecular weight (MW) marker and a standard of the same encapsidated material ranging from 1 µg to 1 ng; and (3) quantitating the liberated nucleic acid using Image J software (Buck and Thompson (2007)).

Loading Protocol of negatively charged drugs by passive diffusion inside particles: Disassembly protocol for modifying open pores with no disassembly, followed by drug and closing of the pores is the same disassembly protocol described above except that the incubation period is lessened to 2 hours at room temperature instead of overnight at 37° C.

Figure 4B:
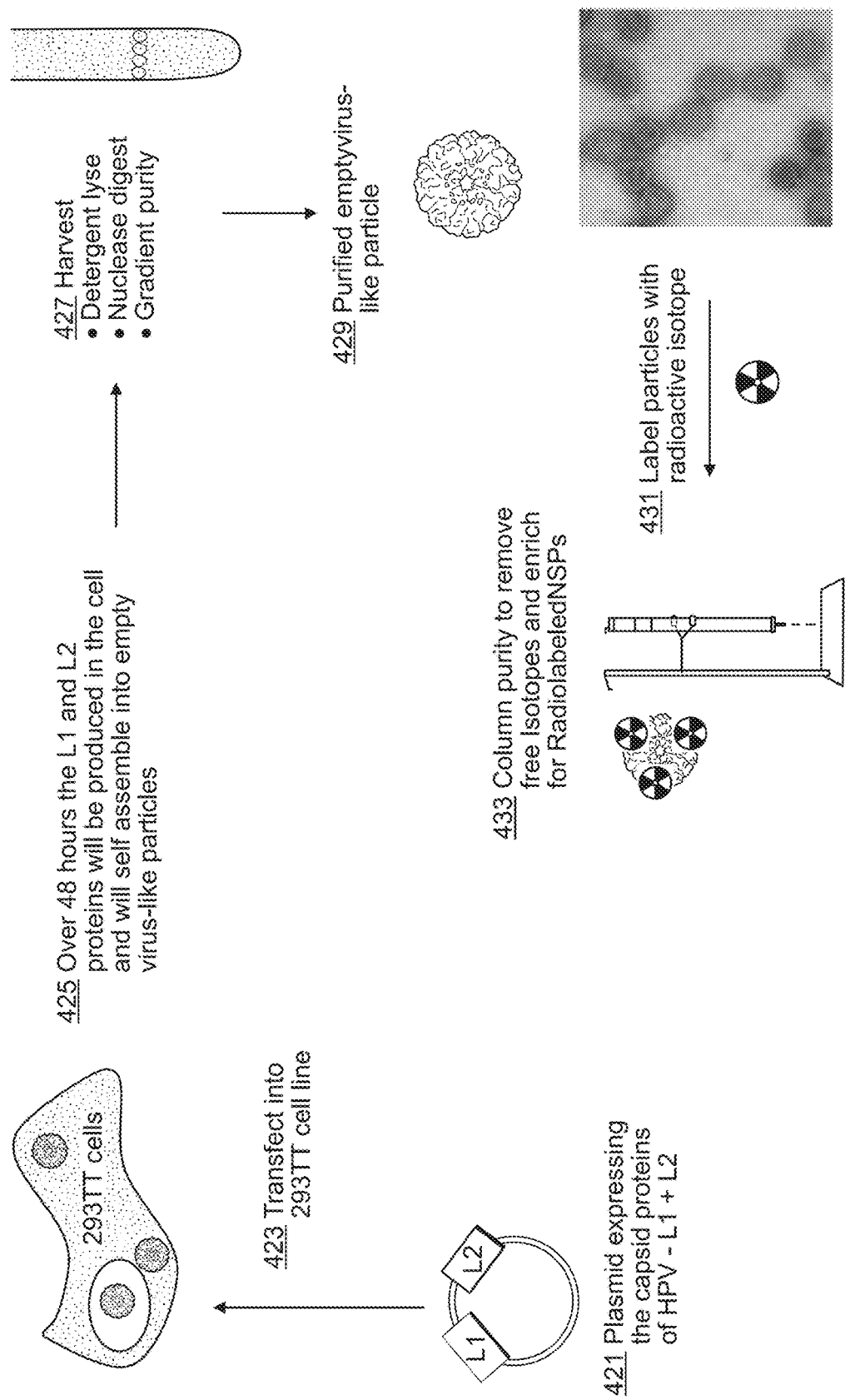

Loading of drugs by chemical conjugation (iodine): Iodixanol is eliminated to enable appropriate binding of Iodine, followed by purification methods. Particles can be purified using a Cesium Chloride gradient, a sucrose gradient, or agarose gel filtration in lieu of Iodixanol. Binding of iodine is done to the exposed histidines in the structure of the protein (FIG. 4B).

Example 3

Biodistribution Study in Parental SKOV3 Orthotopic Tumor Model with Spontaneous Metastasis (FIGS. 5A &B)

An orthotopic murine model for ovarian cancer with spontaneous metastases was used to compare the specificity and efficiency of the nanosphere particle of the present invention with a human papilloma virus (HPV) virus-like particle (VLP) (also referred to herein as PsV particles) for measuring biodistribution. Three groups of severe combined immunodeficiency (SCID) female mice received implantation of SKOV3 (ATCC) parental tumor cell line by unilateral ovarian graft. The experiment was designed to compare HPV pseudovirus (PsV) particles to the nanosphere particles of the present invention. Subjects in group 3 received a single intraperitoneal injection of nanosphere particles (0.65 ml) when tumor sizes reached medium to large by palpation on day 77 post-tumor implantation.

Figure 5B:
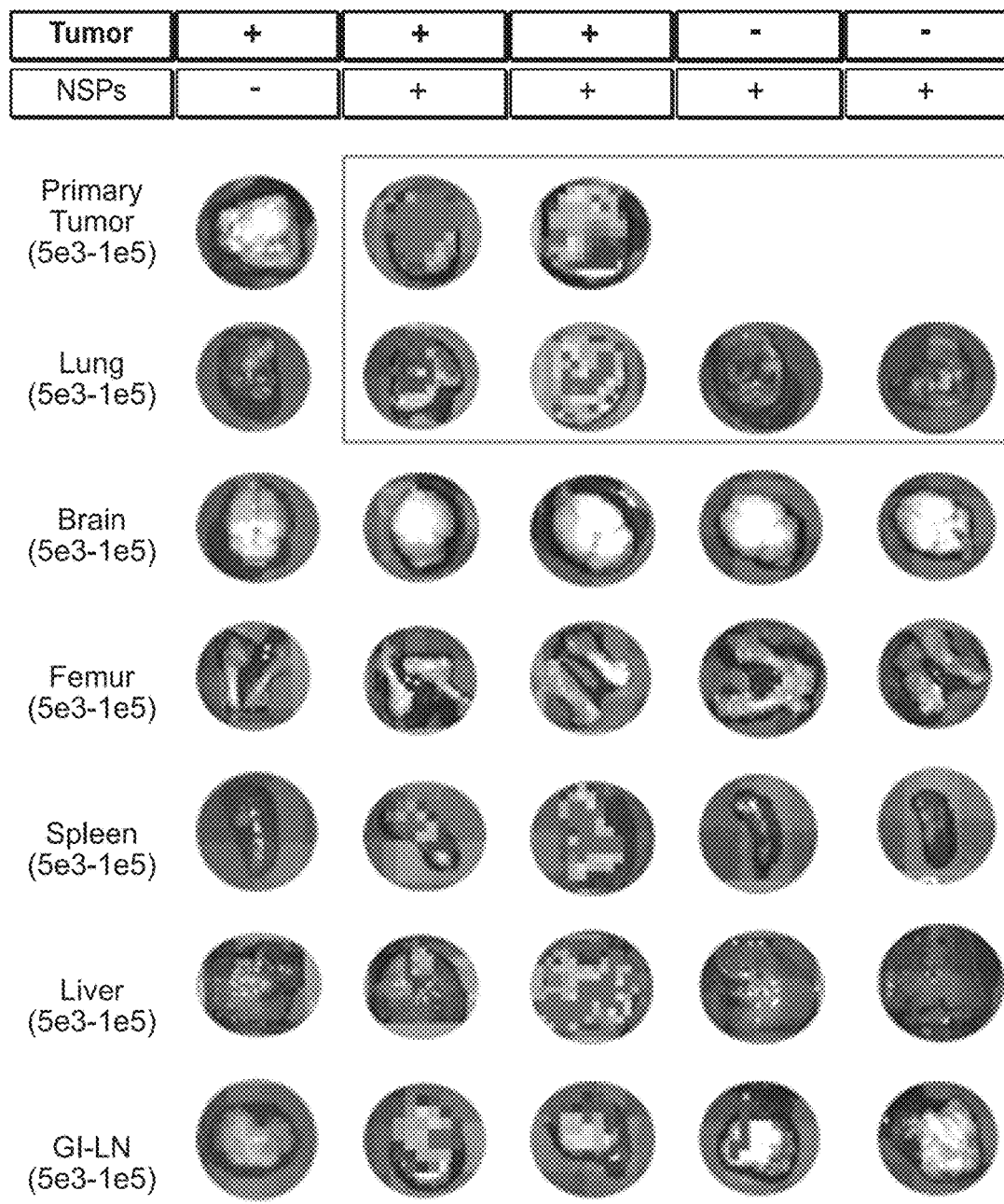

FIG. 5A shows the results of in vivo bioluminescent signals as 48 hours after dosing. FIG. 5B shows the results of ex vivo tissue bioluminescent imaging of the primary tumor and tumors metastasized to the lung, the liver, the spleen GI-LN, the femur and the brain at 48 hours post dosing.

Example 4

Figure 6A:
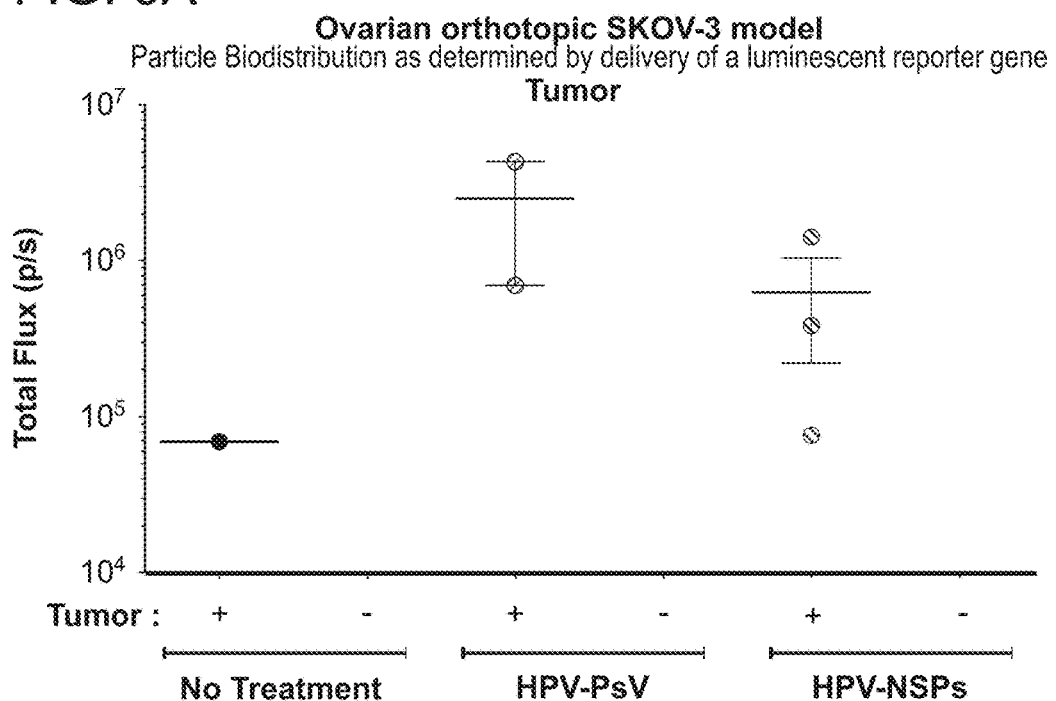
Figure 6B:
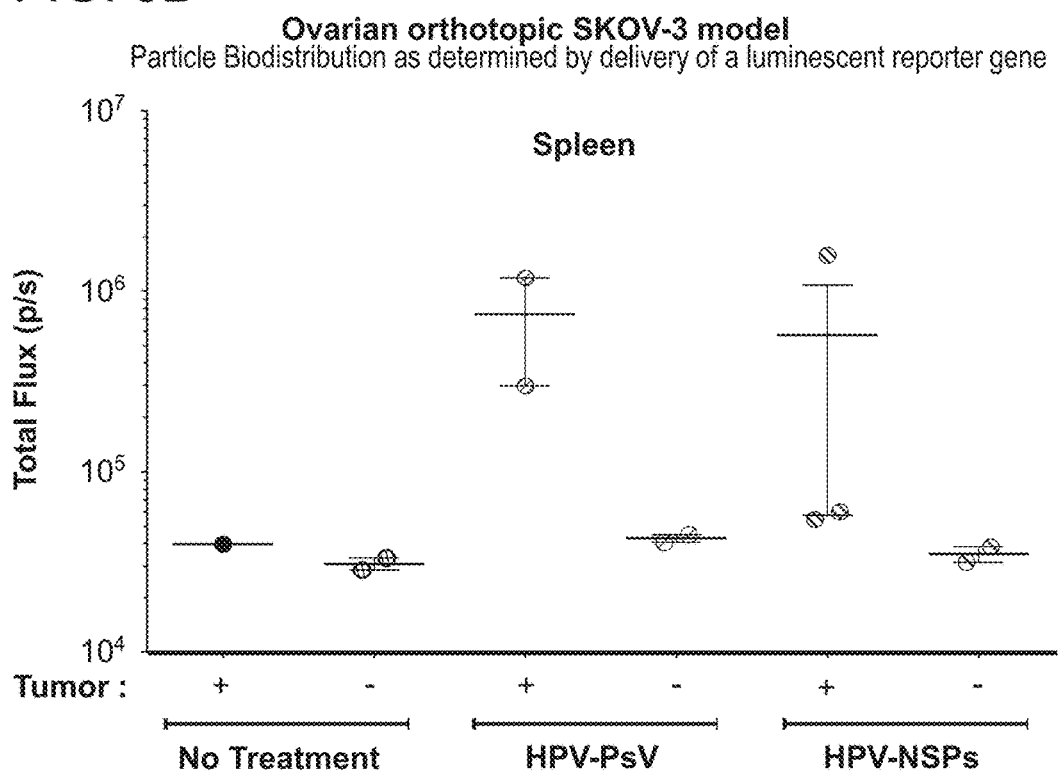
Figure 6C:
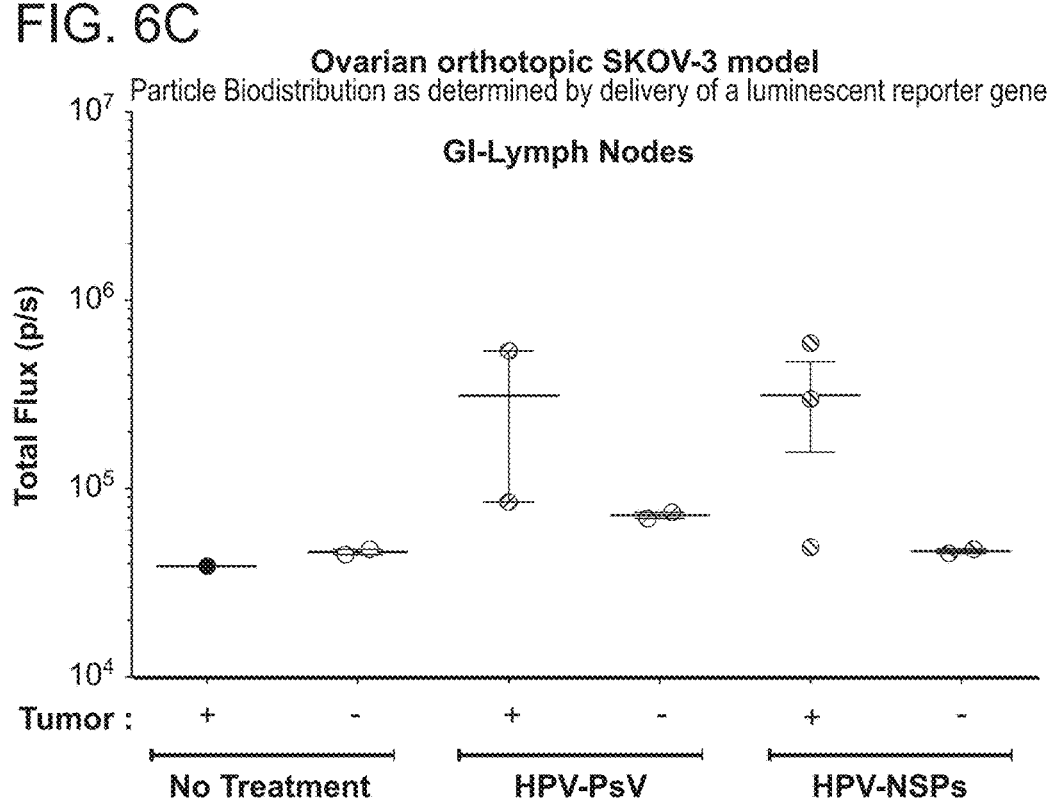
Figure 6D:
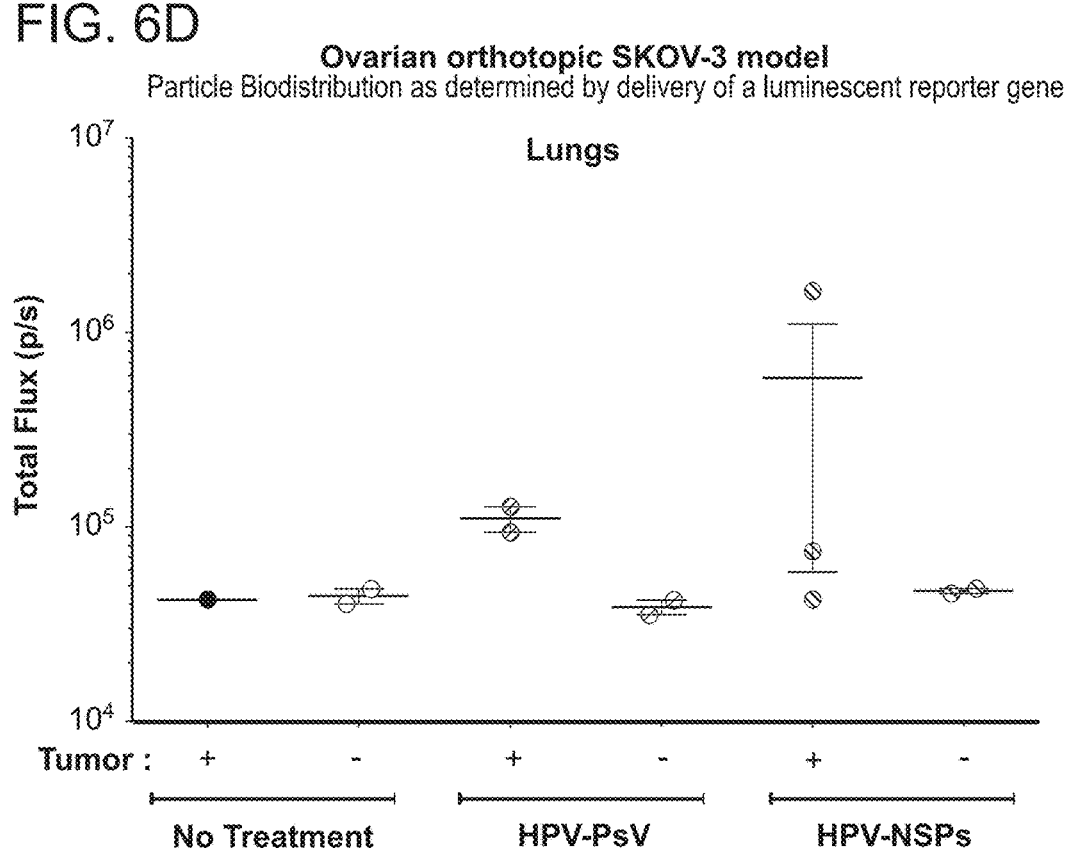

Biodistribution Study in SKOV-3 Mice Comparing Pseudovirions to Nanosphere Particles (FIGS. 6A & B)

In comparing the total luminescence shown between the negative control group, the PsV particles, and the nanosphere particles, the nanosphere particles according to the present invention were shown to produce better distinction which is evidence of a better treatment option. The method of producing forming nanosphere particles eliminates the possibility of introducing host cell DNA. Also, the nanosphere particles exhibit inherent tumor tropism. Thus, the nanosphere particle is a cleaner, more efficient vector for delivery of therapeutic and diagnostic agents, as compared to existing virion-derived particles.

Protocol (FIG. 4A)

For 12 mice receiving PsV particles, a 0.5 µg DNA equivalent is delivered for the following constructs:

16modLuc (Luciferase expression, 9.9.11RK)—0.43 ng DNA/10 µl→0.5 µg=11.6 µl/mouse (an amount sufficient for 16 mice should be made to account for loss: 185.6 µl PsV for 16 mice).

16modRwB (Red fluorescent protein (RFP) expression, 9.9.11RK)—0.41 ng DNA/10 µl→0.5 µg=12.2 µl/mouse (an amount sufficient for 16 mice should be made to account for loss: 195.2 µl PsV for 16 mice).

A preparation is made by combining 185.5 µl of Luc with 195.2 µl of RwB HPV=380.7 µl. This is diluted with 1.6193 mls of sterile DPBS for a VT=2.0 mls. This is mixed well immediately prior to injection, deliver 125 µl/mouse is delivered.

For 20 mice receiving nanosphere particles, a 1 µg DNA equivalent is delivered.

An amount sufficient for 25 mice should be made to account for loss (for 25 mice, the amount should be doubled just in case of loss, so an amount sufficient for 50 mice should be made). The current loading method appears to yield an approximate 50% recovery of loaded DNA, therefore to deliver 1 µg, sufficient "doses" should be made to provide 2 µg/mouse.

A ratio of 5 μg protein:1 μg DNA is used (for 50 mice, 500 μg protein:100 μg DNA is used). The following steps are performed:

Day one—Disassembly using HV16mod L1/L2 VLPs (RK 09.16.11@1.1 mg/ml).

VLPs are disassembled in 50 mM Tris (pH 8.0)/0.5 M NaCl/20 mM EDTA/10 mM DTT—Protein CF=0.05 mg/ml in 20 ml O/N @ 37° C.

Day two—DLS to ensure disassembly—notice some aggregates—60 seconds sonicate.

Using a 100 kD spin column, disassembled particles are concentrated down to 0.2 mg/ml (5 mls). The result is split into two reactions—2.5 mls each. The disassembled particles are combined with 100 μg of plasmid DNA and placed into a 5 ml float-a-lyzer (100 kD). For pCLucF plasmid stock at 0.9 mg/ml, a 111 μl volume is used for 100 μg. For pRwB plasmid stock at 1.3 mg/ml, a 77 μl volume is used for 100 μg. This is dialyzed against 40 mM HEPES (pH 6.8)/0.5 M NaCl/5 mM CaCl2—overnight at room temperature, with three buffer changes.

Day three—Samples are collected and analyzed for DNA and protein content.

16modLuc (10.18.11DD)—0.175 ng DNA/10 μl→1.0 μg=57 μl/mouse. Make enough for 25 mice to account for loss. 1.425 ml HPV Luc for 25 mice. 16modRwB (10.18.11DD)—0.197 ng DNA/10 μl→1.0 μg=50.8 μl/mouse. Make enough for 25 mice to account for loss. 1.27 ml HPV RFP for 25 mice. Combine 1.425 ml of Luc with 1.27 ml of RFP HPV=2.695 ml. Diluted with 0.43 μl of sterile HEPES buffer for a VT=3.125 mls. For the best results, it is imperative to mix well immediately prior to injection—deliver 125 μl/mouse.

Day four—Mice are injected.

EQUIVALENTS AND SCOPE

Those skilled in the art will recognize or be able to ascertain using no more than routine experimentation many equivalents to the specific embodiments described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., some embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

In addition, it is to be understood that any some embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any some embodiment of the methods of the invention can be excluded from any one or more claims, for any reason, whether or not related to the existence of prior art.

Each of the foregoing patents, patent applications and references is hereby incorporated by reference, particularly for the teaching referenced herein.

What is claimed is:

1. A nanosphere particle comprising:
papillomavirus L1 capsid proteins encoded by the nucleic acid sequence of SEQ ID NO: 2; and
a therapeutic agent attached to a surface of the nanosphere particle.

2. The nanosphere particle of claim 1, wherein the therapeutic agent is a dye.

3. The nanosphere particle of claim 1, wherein the therapeutic agent is an anticancer agent.

4. The nanosphere particle of claim 1, wherein the therapeutic agent is a toxic agent.

5. The nanosphere particle of claim 1 further comprising papillomavirus L2 capsid proteins.

6. The nanosphere particle of claim 1, wherein the modified papillomavirus L1 capsid proteins have at least one amino acid that is PEGylated.

7. The nanosphere particle of claim 1, wherein the nanosphere particle is assembled in vitro from a plurality of modified papillomavirus L1 capsid proteins encoded by the nucleic acid sequence of SEQ ID NO: 2.

8. The nanosphere particle of claim 1, wherein the therapeutic agent is covalently attached to a surface of the nanosphere particle.

9. The nanosphere particle of claim 1, wherein the L1 capsid is isolated from bacterial cells, yeast cells, insect cells, plant cells, or mammalian cells.

10. The nanosphere particle of claim 9, wherein the L1 capsid is isolated from mammalian cells.

11. The nanosphere particle of claim 10, wherein the mammalian cells are human embryonic kidney cells.

12. A method comprising delivering to a subject having a tumor the nanosphere particle of claim 1.

13. A method comprising injecting into a tumor of a subject the nanosphere particle of claim 1.

14. The nanosphere particle of claim 1 further comprising papillomavirus L2 capsid proteins, wherein the therapeutic agent is an anti-cancer agent.

15. The nanosphere particle of claim 14, wherein the anti-cancer agent is covalently attached to a surface of the nanosphere particle.

16. A method comprising delivering to a subject having a tumor the nanosphere particle of claim 14.

17. A method comprising injecting into a tumor of a subject the nanosphere particle of claim 14.

18. The nanosphere particle of claim 1 further comprising papillomavirus L2 capsid proteins, wherein the therapeutic agent is a toxic agent.

19. The nanosphere particle of claim 18, wherein the toxic agent is covalently attached to a surface of the nanosphere particle.

20. A method comprising delivering to a subject having a tumor the nanosphere particle of claim 18.

21. A method comprising injecting into a tumor of a subject the nanosphere particle of claim 18.

22. A nanosphere particle comprising:
a papillomavirus L1 capsid protein encoded by the nucleic acid sequence of SEQ ID NO: 2;
papillomavirus L2 capsid proteins; and
a dye attached to a surface of the nanosphere particle.

23. The nanosphere particle of claim 22, wherein the dye is covalently attached to a surface of the nanosphere particle.

24. A method comprising delivering to a subject having a tumor the nanosphere particle of claim 22.

25. A method comprising injecting into a tumor of a subject the nanosphere particle of claim 22.

26. A method comprising expressing in mammalian cells a nucleic acid comprising the sequence of SEQ ID NO: 2, and isolating from the mammalian cells L1 capsid protein encoded by the nucleic acid.

27. The method of claim 26, wherein the mammalian cells are human embryonic kidney (HEK) cells.

28. The method of claim 27, wherein the HEK cells are 293 cells.

29. A cultured mammalian cell comprising a nucleic acid comprising the sequence of SEQ ID NO: 2.

30. The cultured mammalian cell of claim 29, wherein the cultured mammalian cell is a cultured human embryonic kidney (HEK) cell.

31. The mammalian cell of claim 30, wherein the cultured HEK cell is a cultured 293 HEK cell.

* * * * *